US007638624B2

(12) United States Patent
Glick

(10) Patent No.: US 7,638,624 B2
(45) Date of Patent: Dec. 29, 2009

(54) COMPOSITIONS AND METHODS RELATING TO NOVEL BENZODIAZEPINE COMPOUNDS AND DERIVATIVES

(75) Inventor: Gary D. Glick, Ann Arbor, MI (US)

(73) Assignee: The Regents of the University of Michigan, Ann Arbor, MI (US)

(*) Notice: Subject to any disclaimer, the term of this patent is extended or adjusted under 35 U.S.C. 154(b) by 0 days.

(21) Appl. No.: 11/324,419

(22) Filed: Jan. 3, 2006

(65) Prior Publication Data

US 2006/0166975 A1 Jul. 27, 2006

Related U.S. Application Data

(60) Provisional application No. 60/641,040, filed on Jan. 3, 2005.

(51) Int. Cl.
C07D 243/12 (2006.01)
A61K 31/55 (2006.01)
A01N 43/62 (2006.01)
(52) U.S. Cl. ...................................... 540/217; 514/221
(58) Field of Classification Search ................. 540/517
See application file for complete search history.

(56) References Cited

U.S. PATENT DOCUMENTS

| 2,457,405 | A | | 12/1948 | Scott |
| 3,261,828 | A | | 7/1966 | Uskokovic |
| 3,384,635 | A | | 5/1968 | Calabateas |
| 3,415,814 | A | | 12/1968 | Calabeteas |
| 3,847,905 | A | | 11/1974 | Bub |
| 4,076,823 | A | | 2/1978 | Wade |
| 4,088,756 | A | | 5/1978 | Voorhees |
| 4,108,852 | A | | 8/1978 | Bub |
| 4,110,337 | A | | 8/1978 | Szarvasi |
| RE30,293 | E | * | 6/1980 | Bub ........................... 540/517 |
| 4,495,101 | A | | 1/1985 | Klaubert |
| 4,551,480 | A | | 11/1985 | Stiefel |
| 4,751,223 | A | | 6/1988 | Glamkowski |
| 4,820,834 | A | | 4/1989 | Evans |
| 4,894,366 | A | | 1/1990 | Okuhara |
| 4,898,861 | A | | 2/1990 | Morgan |
| 4,916,138 | A | | 4/1990 | Ueda |
| 4,929,611 | A | | 5/1990 | Okuhara |
| 4,946,778 | A | | 8/1990 | Ladner |
| 5,041,438 | A | | 8/1991 | Hsu |
| 5,141,930 | A | | 8/1992 | Nakao |
| 5,216,148 | A | | 6/1993 | Klaus |
| 5,288,514 | A | | 2/1994 | Ellman |
| 5,324,726 | A | | 6/1994 | Bock |
| 5,444,092 | A | | 8/1995 | Collins |
| 5,521,170 | A | * | 5/1996 | Setoi et al. .................. 514/183 |
| 5,545,568 | A | | 8/1996 | Ellman |
| 5,559,230 | A | | 9/1996 | Ogawa |
| 5,591,227 | A | | 1/1997 | Dihn |
| 5,597,915 | A | | 1/1997 | Chambers |
| 5,599,352 | A | | 2/1997 | Dihn |
| 5,633,251 | A | | 5/1997 | Claremon |
| 5,677,282 | A | * | 10/1997 | Oleksyszyn et al. ........... 514/18 |
| 5,697,967 | A | | 12/1997 | Dihn |
| 5,763,437 | A | | 6/1998 | Sato |
| 5,776,946 | A | | 7/1998 | McGeer |
| 5,861,380 | A | | 1/1999 | Gyorkos |
| 5,962,337 | A | | 10/1999 | Ohlmeyer |
| 6,004,942 | A | | 12/1999 | Firestein |
| 6,074,859 | A | | 6/2000 | Hirokawa |
| 6,080,568 | A | | 6/2000 | Glick |
| 6,100,254 | A | | 8/2000 | Budde |
| 6,239,131 | B1 | * | 5/2001 | Shinozaki et al. ........... 514/221 |
| 6,277,844 | B1 | | 8/2001 | Spector |
| 6,319,931 | B1 | | 11/2001 | Kroemer |
| 6,506,744 | B1 | | 1/2003 | Alig |
| 6,524,623 | B1 | | 2/2003 | Hodosh |
| 6,524,832 | B1 | | 2/2003 | Kufe |
| 6,579,854 | B1 | | 6/2003 | Mitchell |
| 6,605,593 | B1 | | 8/2003 | Naicker |
| 6,613,739 | B1 | | 9/2003 | Naicker |
| 6,767,533 | B1 | | 7/2004 | Casellas |
| 6,824,561 | B2 | | 11/2004 | Soykan |
| 6,916,813 | B2 | | 7/2005 | Atwal |

(Continued)

FOREIGN PATENT DOCUMENTS

DE 1810423 10/1969

(Continued)

OTHER PUBLICATIONS

Dorwald F. A. Side Reactions in Organic Synthesis, 2005, Wiley: VCH, Weinheim p. IX of Preface.*
Puodziunaite et al. Chemistry of Heterocyclic Compounds, vol. 36, No. 6, 2000, pp. 698-704.*
Lee et al. J. Org. Chem. 1999, 64, 3060-3065.*
Solomko et al. Chemistry of Heterocyclic Compounds, vol. 11, No. 11, Nov. 1975, pp. 1231-1248.*
Thompson, C.B., "Apoptosis in the Pathogenesis and Treatment of Disease," Science 267:1456-1462 (1995).
Ursini et al., "Synthesis and SAR of New 5-Phenyl-3-ureido-1,5-benzodiazepines as cholecystokinin-B receptor antagonists", J. Med. Chem. 43 (2000) 3596-3613.

(Continued)

Primary Examiner—Shaojia Anna Jiang
Assistant Examiner—Layla Bland
(74) Attorney, Agent, or Firm—Casimir Jones SC

(57) ABSTRACT

The present invention relates to novel chemical compounds, methods for their discovery, and their therapeutic use. In particular, the present invention provides benzodiazepine derivatives and related compounds and methods of using benzodiazepine derivatives and related compounds as therapeutic agents to treat a number of conditions associated with the faulty regulation of the processes of programmed cell death, autoimmunity, inflammation, hyperproliferation, and the like.

19 Claims, 2 Drawing Sheets

| U.S. PATENT DOCUMENTS | | | |
|---|---|---|---|
| 7,125,866 | B1 | 10/2006 | Glick |
| 7,144,880 | B2 | 12/2006 | Glick |
| 7,175,953 | B2 * | 2/2007 | Licha et al. .................. 430/56 |
| 7,220,739 | B2 | 5/2007 | Glick |
| 7,276,348 | B2 | 10/2007 | Glick |
| 2002/0025946 | A1 | 2/2002 | Buchanan |
| 2002/0048566 | A1 | 4/2002 | El-Deiry |
| 2002/0128208 | A1 | 9/2002 | Snyder |
| 2003/0044776 | A1 | 3/2003 | Dykens |
| 2003/0119029 | A1 | 6/2003 | Glick |
| 2004/0009972 | A1 | 1/2004 | Ding |
| 2004/0087489 | A1 | 5/2004 | Ruiz |
| 2004/0157833 | A1 | 8/2004 | Harris |
| 2004/0176358 | A1 | 9/2004 | Glick |
| 2005/0113460 | A1 | 5/2005 | Glick |
| 2005/0261176 | A1 | 11/2005 | Glick |
| 2005/0272723 | A1 | 12/2005 | Glick |
| 2006/0025388 | A1 | 2/2006 | Glick |
| 2006/0052369 | A1 | 3/2006 | Glick |
| 2006/0166975 | A1 | 7/2006 | Glick |
| 2007/0036854 | A1 | 2/2007 | Glick |
| 2007/0043033 | A1 | 2/2007 | Glick |
| 2007/0105844 | A1 | 5/2007 | Glick |
| 2007/0111994 | A1 | 5/2007 | Glick |
| 2007/0135418 | A1 | 6/2007 | Glick |
| 2007/0299059 | A1 | 12/2007 | Glick |
| 2008/0064686 | A1 | 3/2008 | Durrani |

FOREIGN PATENT DOCUMENTS

| | | |
|---|---|---|
| EP | 0349949 | 1/1990 |
| EP | 0227539 | 5/1990 |
| EP | 0349949 | 10/1990 |
| EP | 1143946 | 10/2001 |
| EP | 1423122 | 2/2003 |
| EP | 1398033 | 3/2004 |
| EP | 1398033 | 6/2004 |
| EP | 1622684 | 2/2006 |
| EP | 1742640 | 7/2006 |
| EP | 1778204 | 5/2007 |
| EP | 1786429 | 5/2007 |
| EP | 1845996 | 10/2007 |
| RU | 2096044 | 11/1997 |
| WO | 90/05305 | 5/1990 |
| WO | 90/13332 | 11/1990 |
| WO | 91/12779 | 9/1991 |
| WO | 92/01683 | 2/1992 |
| WO | 94/08234 | 4/1994 |
| WO | 98/57161 | 12/1998 |
| WO | 99/29347 | 6/1999 |
| WO | 99/58117 | 11/1999 |
| WO | 99/66958 | 12/1999 |
| WO | 99/67220 | 12/1999 |
| WO | 00/19200 | 6/2000 |
| WO | 00/66106 | 11/2000 |
| WO | 01/51922 | 7/2001 |
| WO | 02/67988 | 9/2002 |
| WO | 03/015703 | 2/2003 |
| WO | 03/041658 | 5/2003 |
| WO | 03/050261 | 6/2003 |
| WO | 03/106628 | 12/2003 |
| WO | 2005/004988 | 1/2005 |
| WO | 2006/014526 | 2/2006 |
| WO | 2006/029245 | 3/2006 |
| WO | 2006/073448 | 7/2006 |
| WO | 2006/074358 | 7/2006 |
| WO | 2007/050587 | 5/2007 |
| WO | 2007/053193 | 5/2007 |
| WO | 2007/053725 | 5/2007 |
| WO | 2007/146167 | 12/2007 |
| WO | 2008/012553 | 9/2008 |
| WO | 2008/116156 | 9/2008 |

OTHER PUBLICATIONS

Walser, et al., "Quinazolines and 1,4-benzodiazepines. LILX. Preparation of Pyrrolo[2,1-c]-1,4-benzodiazepin-2-ones", J. Org. Chem. 38:3502-3507 (1973).
Watanabe-Fukunaga, R., et al., "Lymphoproliferation Disorder in Mice Explained by Defects in Fas Antigen that Mediates Apoptosia,"Nature 356:314-317 (1992).
White, E., "Life, Death, and the Pursuit of Apoptosis," Genes & Development 10:1-15 (1996).
Williams, D. et al, "Identification of compounds the bind mitochondrial F1F0 ATPase by screening a triazine library . . . " Chemistry & Biol. 11:1251-1259, 9(2004).
Wu, G.Y., et al., "Receptor-Mediated in Vitro Gene Transformation by a Soluble DNA Carrier System," The Journal of Biological Chemistry 262(10):4429-4432 (1987).
Wyllie, A.H., "The Genetic Regulation of Apoptosis," Current Opinion in Genetics & Development 5:97-104 (1995).
Zamzami, N., et al., "Mitochondrial Control of Nuclear Apoptosis," J. Exp. Med. 183:1533-1544 1996.
Zoratti, M., et al., "The Mitochondrial Permeability Transition," Biochimica et Biophysica Acta 1241:139-176 (1995).
International Search Report, International Patent Application No. PCT/U505/24060, dated Dec. 13, 2006.
International Search Report, International Patent Application No. PCT/US02/26171 dated Aug. 8, 2003.
International Search Report, International Patent Application No. PCT/US01/11599 dated Mar. 6, 2001.
International Search Report, International Patent Application No. PCT/US005/031942 dated Sep. 21, 2006.
International Search Report, International Patent Application No. PCT/US04/013455 dated Jan. 6, 2006.
European Search Report, EP Patent Application No. 03 027 484.9-2117 dated May 3, 2004.
European Search Report, EP Patent Application No. 04 775 923.8-2123 dated Nov. 9, 2007.
European Search Report, EP Patent Application No. 00 928 586.7-2117 dated Apr. 23, 2002.
European Search Report, EP Patent Application No. 05 769 345.9 dated Oct. 22, 2007.
International Search Report, PCT/US2006/042753, dated May 6, 2008.
Witten Opinion of the International Searching Authority, PCT/US06/21561, dated Aug. 17, 2007.
International Preliminary Report on Patentability, PCT/US2006/041446, mailed May 8, 2008.
International Search Report and Written Opinion, PCT/US2006/00442, mailed May 12, 2006.
International Report on Patentability, PCT/US2006/000442 mailed Jul. 12, 2007.
Puodziunaite, B., et al., "Bromination of Aromatic Ring of Tetrahydro-1,5-Benzodiazepin-2-Ones", Chemistry of Heterocyclic Compounds, vol. 36, No. 6, 2000.
AU Examiners Report, AU Patent App. No. 2005323519 dated Nov. 27, 2007.
EP Search, EP Patent App. No. 03 027 484.9-2117, dated Jan. 31, 2005.
Canadian Patent Search, CA Patent Application No. 2,457,405, dated Feb. 6, 2007.
Wolvetang, et al., FEBS Letters (1994), 339, 40-44.
International Search Report and Written Opinion, PCT/US08/56231, mailed Jun. 24, 2008.
International Search Report and Written Opinion, PCT/US05/14463, mailed Dec. 4, 2006.
International Search Report and Written Opinion, PCT/US07/11422, mailed Nov. 15, 2007.
International Search Report and Written Opinion, PCT/US07/13576, mailed Nov. 23, 2007.
Godic, "New approaches to psoriasis treatment. A review." 2004, Acta Dermatoven APA, vol. 13, No. 2, pp. 50-57.

International Search Report, PCT/US06/042753, mailed Apr. 19, 2007.
Desjardins, P and Stephanie Ledoux, "The Role of Apoptosis in Neurodegenerative Disease," Metabolic Brian Disease, vol. 13, No. 2, pp. 79-96 (1998).
International Search Report, PCT/US06/41446, mailed Aug. 1, 2007.
AU Patent Application No. 2006203946 Examiner's Report dated Sep. 10, 2008.
Adachi, M., et al., "Aberrant Transcription Caused by the Insertion an Early Transposable Element . . . ," PNAS. USA-90:1756-1760 (1993).
Adelman, N. E., et al., Treatment of (NZB X NZW)F1 Disease with Anti-I-A Monoclonal Antibodies; J. Exp. Med.-158:1350.1355 (1983).
Atwal, K.S., et al., "N-(1-Aryl-2-(1-imidazolo)ethyl)-guanidine derivates as potent inhibitors of the bovine mitochondrial F140 ATP hydrolase" Bioorganic & Medicinal Chem. Ltr., vol. 14, pp. 1021-1030 (2004).
Atwal, K.S., et al., "Small Molecule Mitochondrial F1F0 ATPase Huydrolase Inhibitors as Cardioprotective Agents" J. Med. Chem. 47, pp. 1081-1084 (2004).
Baader, S.L., et al., Uptake and Cytotoxicity of Ascorbic Acid and Dehydroascorbic Acid . . . Anticancer Research-14:221-228 (1994).
Beale, P.J., et al., "BCL-2 Family Protein Expression and Platinum Drug Resistance in Ovarian Carcinoma," British Journal of Cancer-82 (2) :436-440 (2000).
Beurdeley-Thomas, et al., "The peripheral benzodiazepine receptors: a review," Journal of Neuro-Oncology 46 (2000) 45-56.
Blatt, Neal B., "Benzodiazepine-induced superoxide signals B cell apoptosis: mechanistic insight and potential therapeutic utility", The Journal of Clinical Investigation, Oct. 2002, vol. 110, No. 8., pp. 1123-1132.
Blum, P., et al., "Stiff-Person Syndrome: An Autoimmune Disease," Movement Disorders 6(1):12-20 (1991).
Boitano, Anthony, et al., "Structure activity studies of a novel cytotoxic benzodiazepine", Bioorganic & Medicinal Chemistry Letters, Oxford, GB, vol. 13, No. 19, 2003, pp. 3327-3330.
Bono et al., "Peripheral benzodiazepine receptor agonists exhibit potent antiapoptotic activities," Biochemical and Biophysical Research Communications, 1999, 265, pp. 457-461.
Boojamra, C.G., et al., "Solid-Phase Synthesis of 1,4. Benzodiazepine-2,5-Diones. Library Prep. and Demonstration of Synthesis Generality," J. Org. Chem.-62:1240-1256 (1997).
Bunin et al., "Synthesis and evaluation of 1,4-benzodiazepine libraries", Methods in Enzymology, 1996, 267, pp. 448-465.
Bunin, B.A., et al., "The Combinatorial Synthesis and Chemical and Biological Evaluation of a 1,4-Benzodiazepine Libra ," PNAS USA-91:4708-4712 (1994).
Bunin, BA., et al., "A General and Expedient Method for the Solid-Phase Synthesis of 1,4-Benzodlazepine Derivatives," J. Am. Chem. Soc.-114:10997-10998 (1992).
Chumakov,A.M., et al., "Analysis of p53 Transactivation Through High-Affinity Bindir•g Sites," Oncogene-8:3005o3011 (1993).
Churcher et al., "A new series of potent benzodiazepine y-Secretase inhibitors," Bioorganic & Medicinal Chemistry Letters 13 (2003) 179-.
Cohen, P.L., et al., "Lpr and gld: Single Gen• Models of Systemic Autoimmunity and Lymphoproliferative Disease,"Annu. Rev. Immunol. 9:243-269 (1991).
Colosi, et al,"Mutational analysis of the intracellular domain of the human growth hormone recetor", J. Biol. Chem., 268:12617 [1993].
Crabtree, R.H., "A New Type of Hydrogen Bond," Science 282:2000-2001 1998.
Darrow et al., "Structurally similar small molecule photoaffinity CCK-A Agonists and Antagonists as Novel Tools . . . ", Bioorganic & Medicinal Chemistry Letters 8 (1998) 3127-3132.
Desoize, B., "Anticancer Drug Resistance and Inhibition of Apoptosis," Anicancer Research-14:2291-2294 1994.
Dichek, David A., et al., "Seeding of intravascular stents with genetically engineered endothelial cells," Laboratory Investigation, 80:5 pp. 1347-1353 (1989).
Don, A. et al., Cancer Cell, vol. 3, May(2003) 497-509.

Donadio, J.V., et al., Immunosuppressive Drug Therapy in Lupus Nephritis, American Journal of Kidney Diseases 21 (3):239-250 1993.
Ermak, T.H., et al., "Treatment of Murine Lupus with Monoclonal Antibody to L3T4," Laboratory Investigation 61(4):447-456 1989.
Fuh et al, "Rational design of potent antagonists to the human growth hormone receptor", Science, 256:1677 [1992].
Gallant, J.E., et al.,"Incidence and Natural History of Cytomegalovirus Disease in Patients with Advanced Human . . . " The Journal of Infect. Disease, 166: 1223-122 (1992).
Garcia-Calvo, M., et al. "Inhibition of Human Caspases by Peptide-Based and Macromolecular Inhibitors," The Journal of Biological Chemistry 273(49):32608-32613 1998.
Gorczyca, W., et al., "Induction of DNA Slrand Breaks Associated with Apoptosis During Treatment of Leukemias," Leukemia 7(5):659-670 1993.
Gordon, C., et al.. "Chronic Therapy with Recombinant Tumor Necrosis Factor-or in Autoimmune NZB/NZW Fi Mice,"Clinical Immunology and Immunopatholoy- 52:421-434 (1989).
Gordon, E.M., et al., Applications of Combinatorial Technologies to Drug Discovery. 2. Combinatorial Organic 52 Synthesis, Library Screening . . . Journal of Med. Chem. 37(10): (1994).
Grasberger, Bruce L., "Discovery and cocrystal structure of benzodiazepinedione HDM2 antagonists that activate p53 in cells", J. Med. Chem., 48, (2005), 909-912.
Gupta et al., "Psychitripic drugs in dermatology . . . " Database:EMbase (AN:86111413), Journal of the American Academy of Dermatology, 1986, vol. 14, No. 4, pp. 633-645.
Hahn, B.H., et al.; "Influence of Cyclophosphamide and Other Immunosuppressive Drugs on Immune Disorders . . . ," Arthritis and Rheumatism-18(2):145-152 (1975).
Hamann, L.G., et al., "Benzodiazepine-based selective inhibitors of mitochondrial F1F0 ATP hydrolase" Bioorganic & Medicinal Chemistry Ltrs. 14 pp. 1031-1034 (2004).
Hang, L., et al., "A Spontaneous Rheumatoid Arthritis-Like Disease in MR/1 Mice," J. Exp. Mod.-155:1690-1701 1982.
Herranz, R., "Cholesystokinin Antagonists: Pharmacological and Therapeutic Potential", Medicinal Research Reviews 23 (2003) 559-603.
Hirsch, et al., "PK11195, a Ligand of the Mitochondrial Benzodiazepine Receptor, Facilitates the Induction of Apoptosis and Reverses Bcl-2-Mediated Cytoprotection," Experimental Cell Research 241, 426-434 (1998).
Horowitz, R.E., et al., "Cyclophosphamide Treatment of Mouse Systemic Lupus Erythematosus," Laboratory Investigation 21 (3): 199-206 1969.
Hulme, C. J. "Improved procedure for the solution phase preparation of 1,4-benzodiazepine-2,5-dione libraries . . . ", Org. Chem., 63,(1998), 8021-8023.
Huse et al., "Generation of a Large Combinatorial Library of the Immunoglobulin Repertoire in Phage Lambda", Science, 246:1275-1281 [1989].
International Search Report and Written Opinion of PCT/US2008/057827 dated Oct. 6, 2008.
IPER and ISR for PCT/us02/31942 mailed Feb. 2, 2007.
Itoh, N., et al., "The Polypeptide Encoded by the cDNA for Human Cell Surface Antigen Fas Can Mediate Apoptosis," Cell 66:233-243 (1991).
Jones, "The non-conalent interaction of pyrrolo[2,1-c][benzodiazepines-5, 11-diones with DNA, Anti-Cancer Drug Design, 5:249-264 (1990).
Kamal, A., "Synthesis of DNA-interactive Pyrrolo[2,1-c][1,4] benzodiazepines by employing polymer-supported reagents . . . ," Synlett, 14,(2004), 2533-35.
Karle Jesper et al., "Diazepam protects against rat hippocampal neuronal cell death induced by antisense oligodeoxynucleotide to GABA-A receptor gamma-2 subunit" Brain Research, vol. 765, No. 1, 1997, pp. 21-29.
Kerver et al, "In situ detection of spontaneous superoxide anion and singlet oxygen production by mitochondria in . . . ", Histochem. J., 29:229-237 [1997] (Abstract only).
Kim et al., "Synthesis of 3-substituted 1,4-benzodiazepin-2-ones," J. Braz. Chem. Soc. 9:375-379 (1998).

Kohler and Milstein, "Continuous cultures of fused cells . . . ", Nature, 256:495-497 [1975].

Koopman, W.J., et al., "The MRL-lpr/lpr Mouse. A Model for the Study of Rheumatoid Arthritis," Scan& J. Rheumatolo Suppl 75:284-o289 (1988).

Korsmeyer, S.J., "Bcl-2 Initiates a New Category of Oncogenes: Regulators of Cell Death," Blood 80(4):879-886 1992.

Kozbor, et al.• "The production of monoclonal antibodies from human lymphocytes", Immunol. Today, 4:72 [1983].

Lee, Sunwoo, et al., "Improved Catalysts for the Palladium-Catalyzed Synthesis of Oxindoles by . . . ", J. Org. Chem. 2001, 66, pp. 3402-3415.

Lewis et al., "Editors' view: Cancer pharmacotherapy: 21st century 'magic bullets' and changing paradigms", British Journal of Clinical Pharmacology, 2006, 62:1,pp. 1-4.

Liu, J.R., et al., "Bclox•. is Expressed in Ovarian Carcinoma and Modulates Chemotherapy-induced Apoptosis," Gynecologic Oncology 70:398-403 (1998).

Los, M., et al., The Role of Caspases in Development, Immunity, and Apoptotic Signal Transduction: Immunity-10:629-639 (1999).

Lowman, et al., "Mutational analysis and protein engineering of receptor-binding determinants in human placental lactogen", J. Biol. Chem. 266:10982 [1991].

Luria,et al., "Tumor Viruses", General Viology 3rd edition,. 436-446 (1978)-Eds. John Wile & Sons, New York.

Malgrange, B., et al., "I•—Carbolines Induce Apoptotic Death of Cerebellar Granule Neurones in Cultures," NeuroReport 7(18):3041-3045 (1996).

McDonnell'349:254-256T'J" et al., "Progression from Lymphoid Hyperplasia to High-Grade . . . Nature-349:254-256 (1991).

Miccoli, et al., "Potentiation of Lonidamine and Diazepam . . . ", Journal of the National Cancer Institute, vol. 90, No. 18, pp. 1400-1406, Sep. 1998.

Miernik et al., "The antimitotic activities of some benzodiazepines", Experientia, 1986, 42, pp. 956-958.

Miller, K.A., et al., "Benzodiazepines Prevent Neuronal Death by Apoptosis & Necrosis . . . ,"Society for Neuroscience Abstracts-24(1-2):979 (1998).

Monks, A., et., Feasibility of High-Flux Anticancer Drug Screen Using a Diverse Panel of Cultured Human Tumor Cell Lines, Journal of the National Cancer Institute, 83:757-766 (1991).

Nagata, S., "Human Autoimmune Lymphoproliferative Syndrome, a Defect in the Apoptosis-Inducing Fas Receptor: A 55 Lesson from the Mouse Model," J. Hum. Genet 43:2-8 (1998).

Okuyama, H., et al., "Analysis of Defective Delayed-Type Hypersensitivity in Autoimmune Mice Bearing Ipr Gene," Clln. Ex p. ImmunoL 63:87-94 1986.

Okuyama, H., et al., "Effect of Cyclophosphamide Pretreatment on Defective Delayed-Type Hypersensitivity . . . ," Int Arch. Allergy Appl. Immunol. 88:394-40 (1989).

Paola Costantini et al., "Mitochondrion as Novel Target of Anticancer Chemotherapy", JNCI Journal of the National Cancer Institute 2000 92(13): 1042-1053; doi:10. 1093ljnci/92. 13. 1042. (2000).

Parks, Daniel J. "1,4-benzodiazepine-2,5-diones as small molecule antagonists of the HDM2-p53 interaction. . . " Bioorg Med Chem. Ltrs,. 15,(2005), 765-770.

Paull, K.D., et al., "Display and analysis of patterns of differential activity of drugs against human tumor . . . ", J. Natl. Cancer Inst., 81:1088-1092 [1989] (Abstract only).

Pestell, K.E., et al., "Charactehsation of the P53 Status, BCL-2 Expression and Radiation and Platinum Drug Sensitivity of . . . ," Int J. Cancer-77:913-918 (1998).

Ramdas et al., "Benzodiazepine compounds as inhibitors of the Src protein tyrosine kinase . . . " Archives of Biochemistry and Biophysics 368 (1999) 394-400.

Raynaud, F.I., et al., "Intracellular Metabolism of the Orally Active Platinum Drug JM216: Influence of Glutathione Levels," Br. J. Cancer 74(3) :380-?386 (1996).

Russell, J.H., et al., "Mature T Cells of Autoimmune lpr/lpr Mice have a Defect in Antigen-Stimulated Suicide,"Proc. Nat. Acad. Sci. USA 90:4409-4413 (1993).

Sakata, K., et al., "Role of Fas/FasL Interaction in Physiology and Pathology: The Good and the Bad," Clinical Immunology and Immunopathology 87(1):1-7 (1998).

Sandstrom, P.A., et al., Autocrine Production of Extracellular Catalase Prevents Apoptosis.. Proc. Natl. Acad. Sci. USA-90:4708-4712 (1993).

Schlumpf, M., et al., "Delayed Developmental Immunotoxicity of Prenatal Benzodiazepines," Toxic. In Vitro-8 (5):1061-1065(1994).

Schoemaker, H., et al., "Specific High-Affinity Binding Sites for [3H]Ro5—4864 in Rat Brain and Kidney," The J. of Pharm and Experimental Therapeutics-225(1)61-69 (1983).

Schwab, M., et al., "Amplified DNA with Limited Homology to myc Cellular Oncogene is Shared by Human Neuroblastoma Cell Lines and . . . ," Nature-305:245-248 (1983).

Scott, C.F., et al., "Comparison of Antigen-Specific T Cell Responses in Autoimmune MRL/mp-Ipr/lpr and MRUMp-++ Mice," The Journal of Immunology-1322:633-639 (1994_.

Sentman, C.L., et al., "bcl-2 Inhibits Multiple Forms of Apoptosis but not Negative Selection in Thymocytes," Cell 67:879-886 (1991).

Shaughnessy, Kevin, H., et al., "Palladium-Catalyzed Inter- and Intramolecular . . . " J. Org. Chem. 1998, 63, pp. 6546-6553.

Sheppard, R.C., et al., "Acid-Labile Resin Linkage Agents for Use in Solid Phase Peptide Synthesis;" Int J. Peptide Protein Res. 20:451-454 (1982).

Snyder, Jane R., et al, "Dissection of melanogenesis with small molecules identifies prohibition as a regulator", Chemistry & Biol. 12:477-484, 4(2005).

Stevens, S.Y., et al., "Non Nucleic Acid Inhibitors of Protein-DNA Interactions Identified Through Combinatorial Chemistry," J. Am. Chem.Soc.-118:10650-10651 (1996).

Sugimoto, T., et al., Determination of Cell Surface Membrane Antigens . . . JNCI-73: (1):51-57 (1984).

Swanson et al, "Ligand recognition by anti-DNA Autoantibodies," Biochemistry, 35:1624-1633 [1996] (Abstract only).

Swanson, P.C., et al., "Ligand Recognition by Murine Anti-DNA Autoantibodies," J. Clin. Invest 97(7):1748-1760 (1996).

Swanson, P.C.,et al., "High Resolution Ephope Mapping of an Anti-DNA Autoantibody Using Model DNA Ligands," J. Immunology 71 152(5):2601-2612 (1994).

Takahashi, T., et al., "Generalized Lymphoproliferative Disease in Mice, Caused by a Point Mutation in the Fas Ligand;" Cell 76:969-976 (1994).

Tanimoto, Y., et al., Benzodiazepine Receptor Agonists Modulate Thymocyte Apoptosis Through Reduction of the Mitochondrial . . . Jpn. J. Pharmacol. 79:177-183 (1999).

Taupin, V., et al., Endogenous Anxiogenic peptide, ODN-Diazepam-Binding Inhibitor, and Benzodiazepines.. Lymphokine and Cytoklne Research 10(1):7-13 (1991).

EP Supplementary Search Report mailed Nov. 6, 2008, EP Patent Application No. 02794914.8.

Cole et al., "The EBV-Hybridoma Technique and its Application to Human Lung Cancer", Monoclonal Antibodies and Cancer Therapy, Alan R. Liss, Inc., pp. 77-96 [1985].

Doble, A., et al., "Labelling of Peripheral-Type Benzodiazepine B Human Brain with [aH]I 1195: Anatomical and Subcellular Distribution," Brain Research Bulletin,18:49-61 1987.

Marino, M., et al., "Prevention of Systemic Lupus Erythematosus in MRL/Ipr Mice by Administration of an Immunoglobulin . . . ," Nature Biotechnology-18:735-739 (2000).

Ozols, R.F., "Paclitaxel Plus Carboplatin in the Treatment of Ovarian Cancer," Seminars in Oncology 26(1) (Supp.2:84-89 (1999).

Raboisson, P. "Structure-based design, synthesis and biological evaluative of novel 1,4-diazepines as HDM2 antagonists," Bioorg Med Chem. Ltrs., 15,(2005), 1857-1861.

Theoffopoulous, AN, et al., "Murine Models of Systemic Lupus Erythematosus," Advances in Immunology 37:269-390 (1985).

Nawrocka, et al., Arch. Pharm. (Weinheim) Jan. 2001, 334(1), 3-10.

Otto, Michael W., Ph.D., et al., "Benzodiazepine Use, Cognitive Impairment, and Cognitive-Behavioral Therapy for Anxiety Disorders: Issues in the Treatment of a Patient in Need," J. Clin. Psychiatry, 2005, 66 (supp 2).

Yoshi, M., et al., (2005) Nippon Yakurigaku Zasshi 125(1):33-36 (English Abstract attached).

Yasuda, K., (2004) Nippon Rinsho. 62 Suppl. 12:360-363. Abstract not available.

Decaudin, Didier, "Peripheral benzodiazepine receptor and its clinical targeting," Anti-Cancer Drugs, 2004, vol. 15, No. 8.

Bonnot, O., et al., "Exposition in utero au lorazepam et atresie anale: signal epidemiologique," (2003) Encephale. 29 (6):553-559.

Lacapere, Jean-Jacques, Vassilios Papadopoulos, "Peripheral-type benzodiazepine receptor: structure and function of a cholesterol-binding protein in steroid and bile acid biosynthesis," Steroids, 68 (2003) 569-585.

Galiegue, S., et al., "The Peripheral Benzodiazepine Receptor: A Promising Therapeutic Drug Target," (2003) Curr. Med. Chem (10(16):1563-1572.

Papadopoulo, V. (2003), Lecture: Peripheral benzodiazepine receptor: structure and function in health and disease, Ann. Pharm. Fr. 61(1):30-50.

Goethals, Ingeborg, et al., "Is central benzodiazepine receptor imaging useful for the identification of epileptogenic foci in localization-related epilepsies?" European Journal of Nuclear Medicine and Molecular Imaging vol. 30, No. 2, Feb. 2003.

Castedo, Marian, et al., "Mitochondrial Apoptosis and the Peripheral Benzodiazepine Receptor: a Novel Target for Viral and Pharmacological Manipulation," The Journal of Experimental Medicine, vol. 196, No. 9, Nov. 4, 2002.

Buffett-Jerrott S.E. et al., "Cognitive and Sedative Effects of Benzodiazepine Use," Current Pharmaceutical Design, 2002, 8, 45-48.

Smyth, W.F., et al. (1998), "A critical evaluation of the application of capillary electrophoresis to the detection and determination of 1,4-benzodiazepine tranquilizers in formulations and body materials," Electrophoresis 19 (16-17):2870-2882.

Yoshii, M., et al. (1998) Nihon Shinkeo Seishin Yakurigaku Zasshi, 18(2):49-54.

Varani, et al., (1994), "All-trans Retinoic Acid (RA) Stimulates Events in Organ-cultured Human Skin that Underlie Repair," J. Clin. Invest., 94:1747-1753.

Griffith, C.E., "Editorial Comment: Ascomycin: an advance in the management of atopic dermatitis," Br. J. Dermatol., 2001, April; 144(4):679-81.

Stern, R.S. (1995), "Epidemiology of Psoriasis," Dermatologic Clinics, 13:717-722.

Fry, L (1988), "Psoriasis," Brit. J. Dermatol., 119:445-461.

Krueger GC, et al., (1984), "Psoriasis," J. Am. Acad. Dermatol., 11:937-947.

Varani, J., et al. (2001), "Heparin-Binding Epidermal-Growth-Factor-Like Growth Factor Activation of Keratinocyte ErbB . . . ", J. Invest. Dermatol., 117:1335-1341.

Varani, J., et al., "A Novel Benzodiazepine Selectively Inhibits Keratinocyte Proliferation . . . ", The Journal of Pharmacology and Experimental Therapeutics, 2005, vol. 313, No. 1, pp. 56-63.

International Search Report and Written Opinion, PCT/US2008/082629, mailed Jun. 1, 2009.

Bisaha, S.N., et al., A switch in enantiomer preference between mitochondrial F1F0-ATPase chemotypes, Bioorganic & Medicinal Chemistry Letters, 2005 15(11), pp. 2749-2751.

International Search Report and Written Opinion dated Mar. 27, 2009, PCT/US2008/076021.

EP Supplementary Search Report, EP Application No. 02794914.8 dated Nov. 6, 2008.

EP Patent Application No. 05 80 4417 Supplementary European Search Report dated Mar. 26, 2009.

Algarra, et al., "Application of the Photo-Fries Rearrangement of Aryl N-Chloroacetylanthranylates as Key Step in the . . . ", Heterocycles, vol. 36 1993, pp. 2335-2344.

EP Patent Application No. 06 717616 Supplementary Search Report dated Mar. 26, 2009.

Levitzki, Alexander, "Protein Tyrosine Kinase Inhibitors as Novel Therapeutic Agents," Pharmacol. Ther. vol. 82, Nos. 2-3, pp. 231-239 (1999).

Sanchez, et al., "Tumorigenic activity of the BCR-ABL oncogenes is mediated by BCL2" Proc Natl Acad Sci U S A (Jun. 6, 1995) 92(12) 5287-5291.

Ji Yang, et al., "Prevention of Apoptosis by BCL-2; Release of Cytochrome c from Mitochondria Blocked" Science vol. 275, No. 5303, pp. 1129.

Prindull, "Apoptosis in the embryo and tumorigenesis" European Journal of Cancer, vol. 31, Issue 1 (1995) pp. 116-123.

Chinese Office Action, CN Patent Application No. 200580029827.4, dated Apr. 17, 2009.

Lowe, "Systemic treatment of severe psoriasis," The New England Journal of Medicine, 324 (5), Feb. 7, 1991, pp. 333-334.

Laupacis, et al., "Cyclosporin A: a powerful immunosuppressant", CMA Journal, May 1, 1982, vol. 126, pp. 1041-1046.

\* cited by examiner

COMPOSITIONS AND METHODS RELATING TO NOVEL BENZODIAZEPINE COMPOUNDS AND DERIVATIVES

The present application claims priority to U.S. Provisional Patent Application Ser. No. 60/641,040, filed Jan. 3, 2005, which is herein incorporated by reference in its entirety.

This invention was supported in part with NIH grants GM46831 and AI47450. The United States government may have rights in this invention.

FIELD OF THE INVENTION

The present invention relates to novel chemical compounds, methods for their discovery, and their therapeutic use. In particular, the present invention provides benzodiazepine derivatives and related compounds and methods of using benzodiazepine derivatives and related compounds as therapeutic agents to treat a number of conditions associated with the faulty regulation of the processes of programmed cell death, autoimmunity, inflammation, hyperproliferation, and the like.

BACKGROUND OF THE INVENTION

Multicellular organisms exert precise control over cell number. A balance between cell proliferation and cell death achieves this homeostasis. Cell death occurs in nearly every type of vertebrate cell via necrosis or through a suicidal form of cell death, known as apoptosis. Apoptosis is triggered by a variety of extracellular and intracellular signals that engage a common, genetically programmed death mechanism.

Multicellular organisms use apoptosis to instruct damaged or unnecessary cells to destroy themselves for the good of the organism. Control of the apoptotic process therefore is very important to normal development, for example, fetal development of fingers and toes requires the controlled removal, by apoptosis, of excess interconnecting tissues, as does the formation of neural synapses within the brain. Similarly, controlled apoptosis is responsible for the sloughing off of the inner lining of the uterus (the endometrium) at the start of menstruation. While apoptosis plays an important role in tissue sculpting and normal cellular maintenance, it is also the primary defense against cells and invaders (e.g., viruses) which threaten the well being of the organism.

Not surprisingly many diseases are associated with dysregulation of the process of cell death. Experimental models have established a cause-effect relationship between aberrant apoptotic regulation and the pathenogenicity of various neoplastic, autoimmune and viral diseases. For instance, in the cell mediated immune response, effector cells (e.g., cytotoxic T lymphocytes "CTLs") destroy virus-infected cells by inducing the infected cells to undergo apoptosis. The organism subsequently relies on the apoptotic process to destroy the effector cells when they are no longer needed. Autoimmunity is normally prevented by the CTLs inducing apoptosis in each other and even in themselves. Defects in this process are associated with a variety of autoimmune diseases such as lupus erythematosus and rheumatoid arthritis.

Multicellular organisms also use apoptosis to instruct cells with damaged nucleic acids (e.g., DNA) to destroy themselves prior to becoming cancerous. Some cancer-causing viruses overcome this safeguard by reprogramming infected (transformed) cells to abort the normal apoptotic process. For example, several human papilloma viruses (HPVs) have been implicated in causing cervical cancer by suppressing the apoptotic removal of transformed cells by producing a protein (E6) which inactivates the p53 apoptosis promoter. Similarly, the Epstein-Barr virus (EBV), the causative agent of mononucleosis and Burkitt's lymphoma, reprograms infected cells to produce proteins that prevent normal apoptotic removal of the aberrant cells thus allowing the cancerous cells to proliferate and to spread throughout the organism.

Still other viruses destructively manipulate a cell's apoptotic machinery without directly resulting in the development of a cancer. For example, the destruction of the immune system in individuals infected with the human immunodeficiency virus (HIV) is thought to progress through infected CD4$^+$ T cells (about 1 in 100,000) instructing uninfected sister cells to undergo apoptosis.

Some cancers that arise by non-viral means have also developed mechanisms to escape destruction by apoptosis. Melanoma cells, for instance, avoid apoptosis by inhibiting the expression of the gene encoding Apaf-1. Other cancer cells, especially lung and colon cancer cells, secrete high levels of soluble decoy molecules that inhibit the initiation of CTL mediated clearance of aberrant cells. Faulty regulation of the apoptotic machinery has also been implicated in various degenerative conditions and vascular diseases.

It is apparent that the controlled regulation of the apoptotic process and its cellular machinery is vital to the survival of multicellular organisms. Typically, the biochemical changes that occur in a cell instructed to undergo apoptosis occur in an orderly procession. However, as shown above, flawed regulation of apoptosis can cause serious deleterious effects in the organism.

There have been various attempts to control and restore regulation of the apoptotic machinery in aberrant cells (e.g., cancer cells). For example, much work has been done to develop cytotoxic agents to destroy aberrant cells before they proliferate. As such, cytotoxic agents have widespread utility in both human and animal health and represent the first line of treatment for nearly all forms of cancer and hyperproliferative autoimmune disorders like lupus erythematosus and rheumatoid arthritis.

Many cytotoxic agents in clinical use exert their effect by damaging DNA (e.g., cis-diaminodichroplatanim(II) crosslinks DNA, whereas bleomycin induces strand cleavage). The result of this nuclear damage, if recognized by cellular factors like the p53 system, is to initiate an apoptotic cascade leading to the death of the damaged cell.

However, existing cytotoxic chemotherapeutic agents have serious drawbacks. For example, many known cytotoxic agents show little discrimination between healthy and diseased cells. This lack of specificity often results in severe side effects that can limit efficacy and/or result in early mortality. Moreover, prolonged administration of many existing cytotoxic agents results in the expression of resistance genes (e.g., bcl-2 family or multi-drug resistance (MDR) proteins) that render further dosing either less effective or useless. Some cytotoxic agents induce mutations into p53 and related proteins. Based on these considerations, ideal cytotoxic drugs should only kill diseased cells and not be susceptible to chemo-resistance.

One strategy to selectively kill diseased cells is to develop drugs that selectively recognize molecules expressed in diseased cells. Thus, effective cytotoxic chemotherapeutic agents, would recognize disease indicative molecules and induce (e.g., either directly or indirectly) the death of the diseased cell. Although markers on some types of cancer cells have been identified and targeted with therapeutic antibodies and small molecules, unique traits for diagnostic and therapeutic exploitation are not known for most cancers. Moreover, for diseases like lupus, specific molecular targets for drug development have not been identified.

What are needed are improved compositions and methods for regulating the apoptotic processes in subjects afflicted with diseases and conditions characterized by faulty regulation of these processes (e.g., viral infections, hyperproliferative autoimmune disorders, chronic inflammatory conditions, and cancers).

SUMMARY

The present invention provides novel compounds that find use in treating a number of diseases and conditions and that find use in research, compound screening, and diagnostic applications. The present invention also provides uses of these novel compounds, as well as the use of known compounds, that elicit particular biological responses (e.g., compounds that bind to particular target molecules and/or cause particular cellular events). Such compounds and uses are described throughout the present application and represent a diverse collection of compositions and applications.

Certain preferred compositions and uses are described below. The present invention is not limited to these particular compositions and uses.

The present invention provides a number of useful compositions as described throughout the present application. Certain preferred embodiments of the present invention include a composition comprising the following formula:

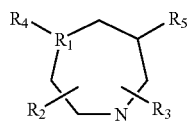

including both R and S enantiomeric forms and racemic mixtures; wherein $R_1$ is a nitrogen atom or a carbon atom; wherein $R_2$ is comprises a chemical moiety comprising a heterocyclic group containing 3 or more carbon atoms; wherein $R_3$ comprises a chemical moiety comprising a heterocyclic group containing 3 or more carbon atoms; and wherein $R_4$ and $R_5$ are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety.

In preferred embodiments, the composition comprises the formula:

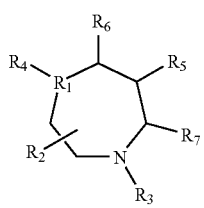

wherein $R_6$ is selected from the group consisting of H and a ketone; and wherein $R_7$ is selected from the group consisting of H and a ketone.

In preferred embodiments, the composition comprises the formula:

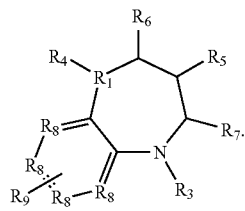

In such preferred embodiments, $R_8$ is carbon or nitrogen and $R_9$ is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; $SR'$; and $NR'_2$, wherein $R'$ is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In preferred embodiments, the composition comprises the formula:

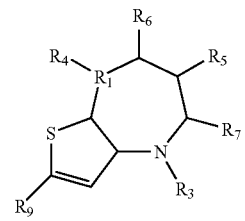

wherein $R_9$ is selected from H, a hydroxy, an alkoxy, a halo, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; $SR'$; and $NR'_2$, wherein $R'$ is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In preferred embodiments, the composition comprises the formula:

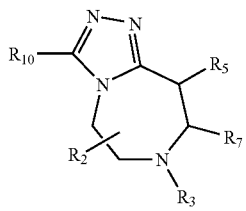

wherein R10 is selected from the group consisting of: hydrogen; halogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R7 is selected from the group consisting of H and a ketone.

In other preferred embodiments, R3 is selected from the group consisting of:

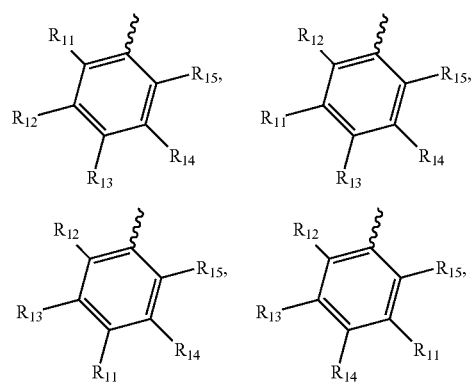

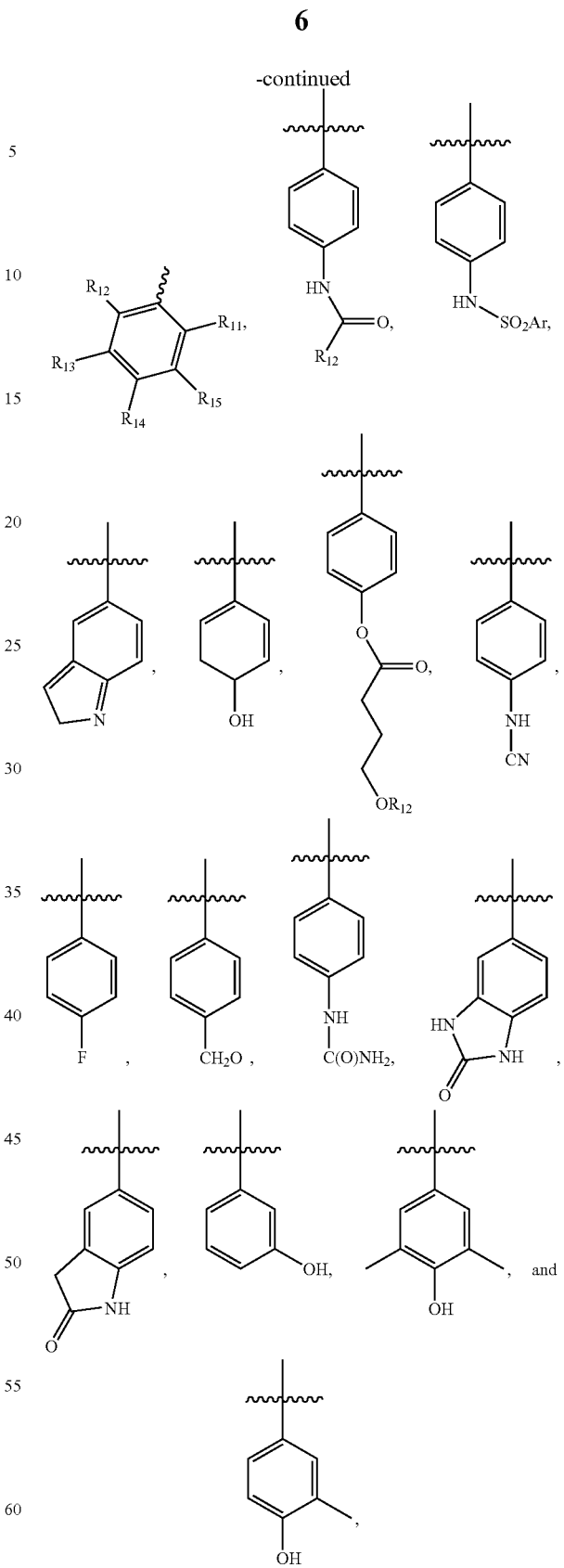

wherein R12, R13, R14 and R15 are selected from the group consisting of: hydrogen; CH$_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In yet other preferred embodiments, R4 or R5 are selected from group consisting of: napthalalanine; phenol; 1-Napthalenol; 2-Napthalenol;

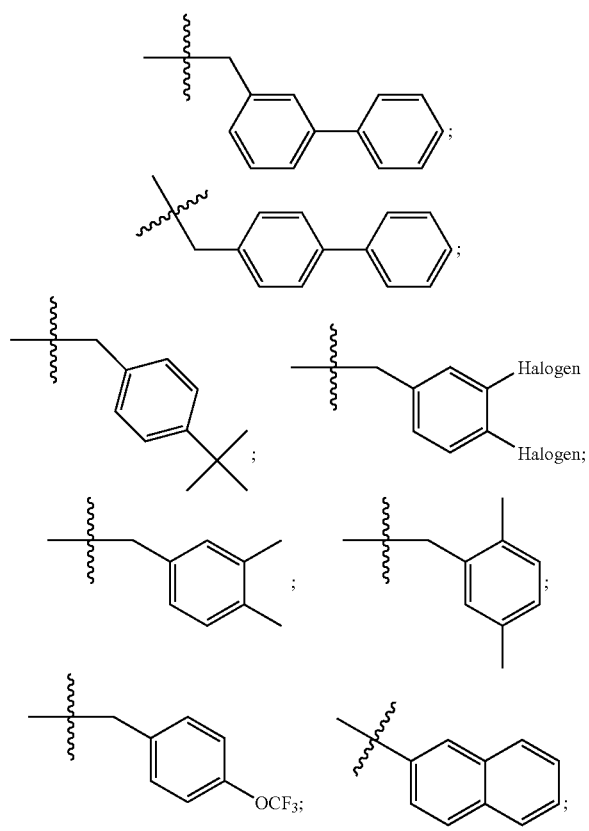

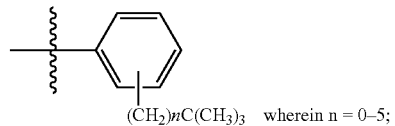

$(CH_2)nC(CH_3)_3$ wherein n = 0–5;

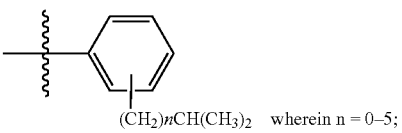

$(CH_2)nCH(CH_3)_2$ wherein n = 0–5;

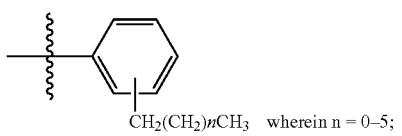

$CH_2(CH_2)nCH_3$ wherein n = 0–5;

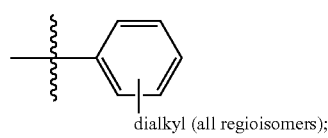

dialkyl (all regioisomers);

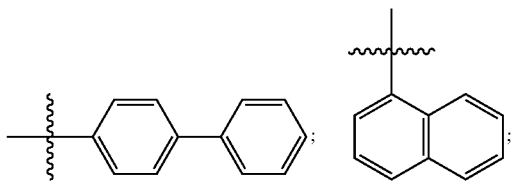

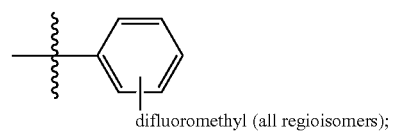

difluoromethyl (all regioisomers);

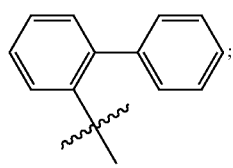

quinolines, and all aromatic regioisomers.

In other preferred embodiments, R4 or R5 is selected from the group consisting of:

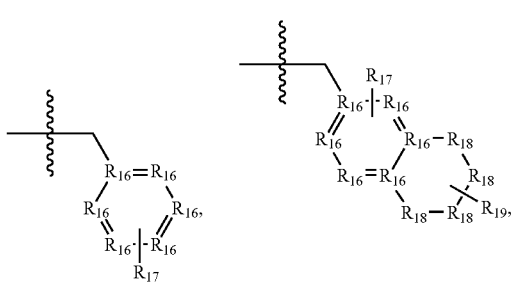

-continued

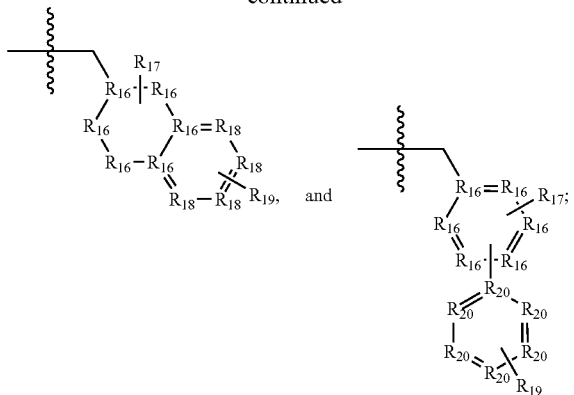

wherein R16 is carbon or nitrogen; wherein R17 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In preferred embodiments, the composition is:

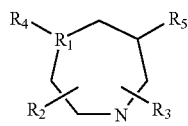

In certain embodiments, the present invention provides a method for cell regulation comprising: a) providing i. target cells having mitochondria; ii. and a composition comprising the following formula:

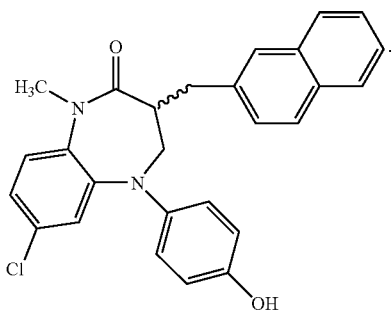

including both R and S enantiomeric forms and racemic mixtures; wherein R1 is a nitrogen atom or a carbon atom; wherein R2 is comprises a chemical moiety comprising a heterocyclic group containing 3 or more carbon atoms; wherein R3 comprises a chemical moiety comprising a heterocyclic group containing 3 or more carbon atoms; and wherein R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and b) exposing the cells to the composition under conditions such that the composition binds to the mitochondria so as to increase superoxide levels or alter cellular ATP levels in the cells.

In preferred embodiments, the composition comprises the formula:

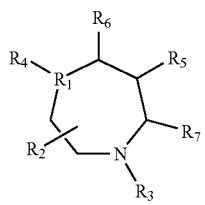

wherein R6 is selected from the group consisting of H and a ketone; and wherein R7 is selected from the group consisting of H and a ketone.

In preferred embodiments, the composition comprises the formula:

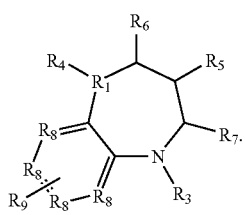

In such preferred embodiments, R8 is carbon or nitrogen and R9 is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In preferred embodiments, the composition comprises the formula:

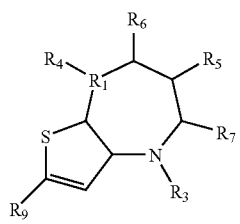

wherein R9 is selected from H, a hydroxy, an alkoxy, a halo, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In other preferred embodiments, the composition comprises the formula:

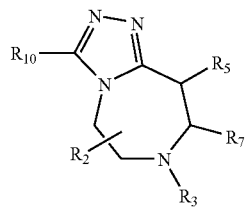

wherein R10 is selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R7 is selected from the group consisting of H and a ketone.

In yet other embodiments, R3 is selected from the group consisting of:

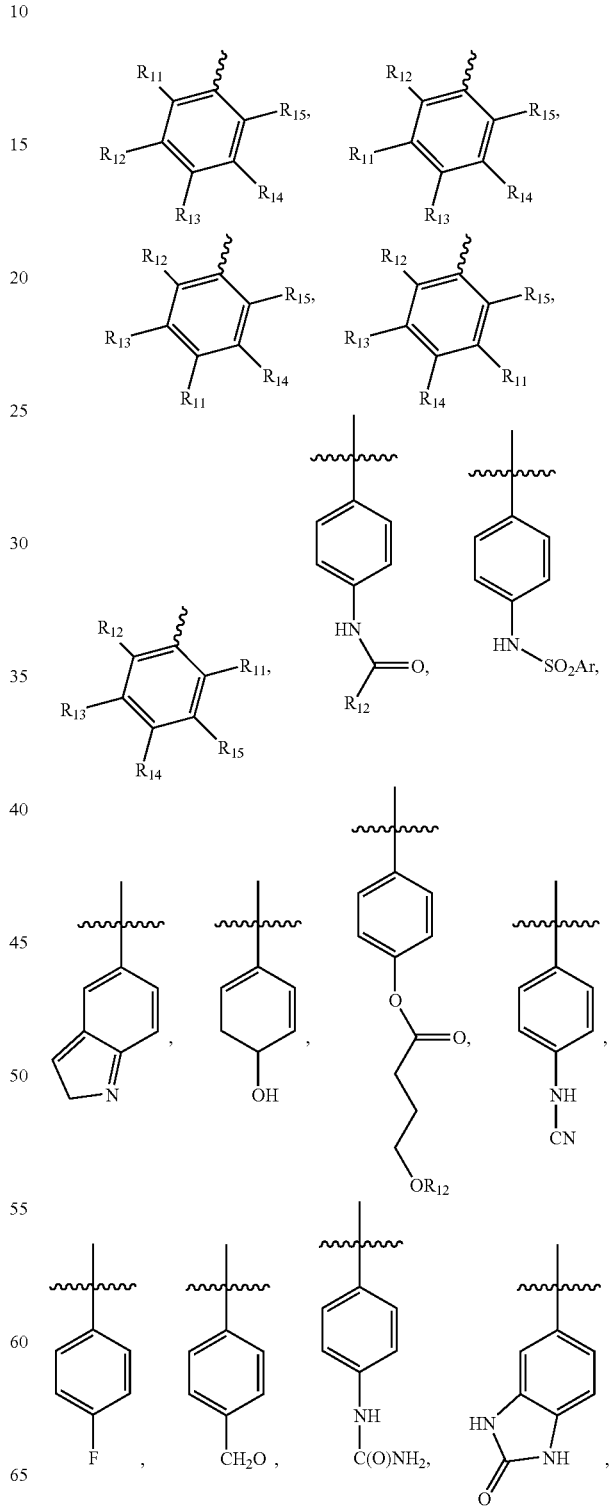

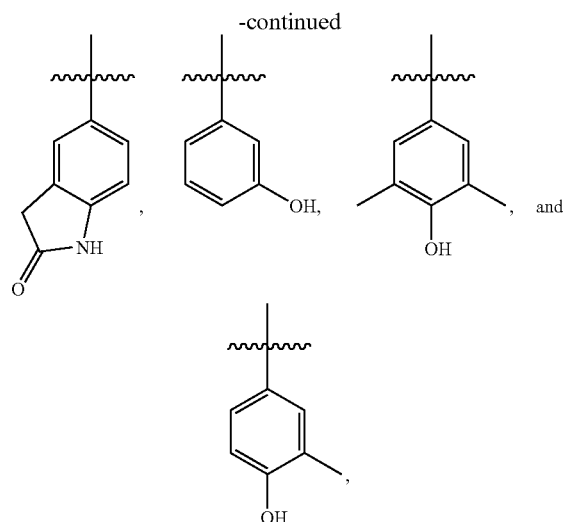

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In preferred embodiments, R4 or R5 are selected from group consisting of: napthalalanine; phenol; 1-Napthalenol; 2-Napthalenol;

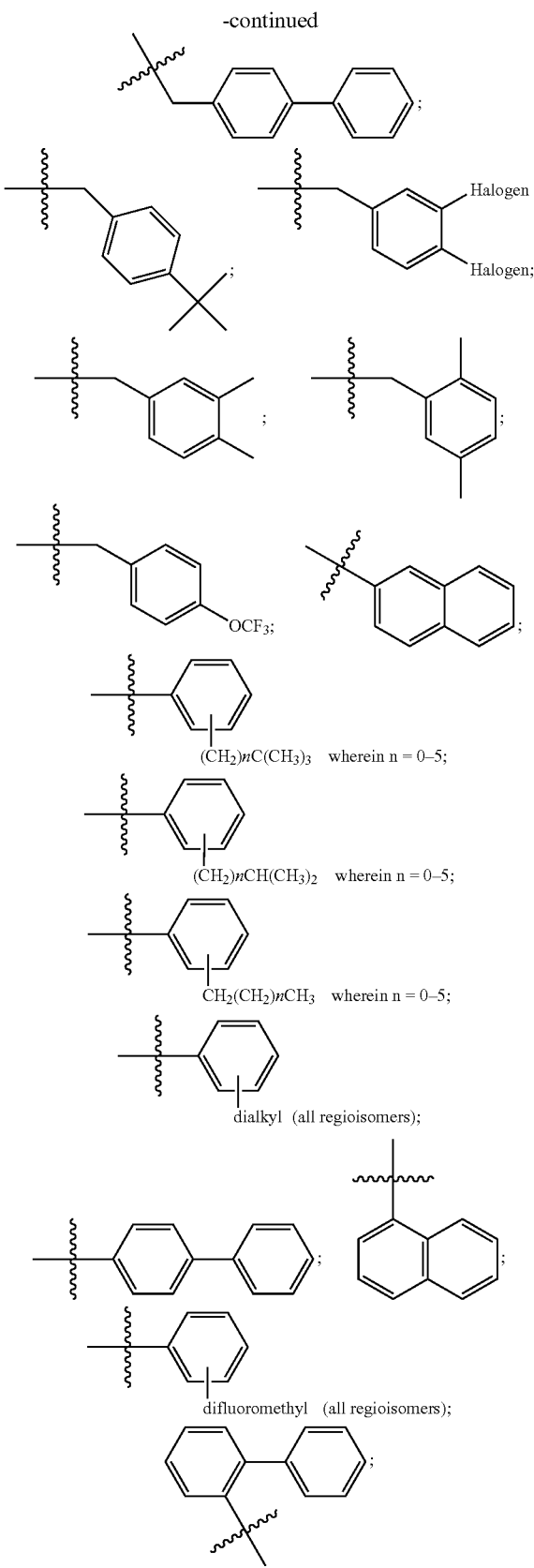

quinolines, and all aromatic regioisomers.

In yet other embodiments, R4 or R5 is selected from the group consisting of:

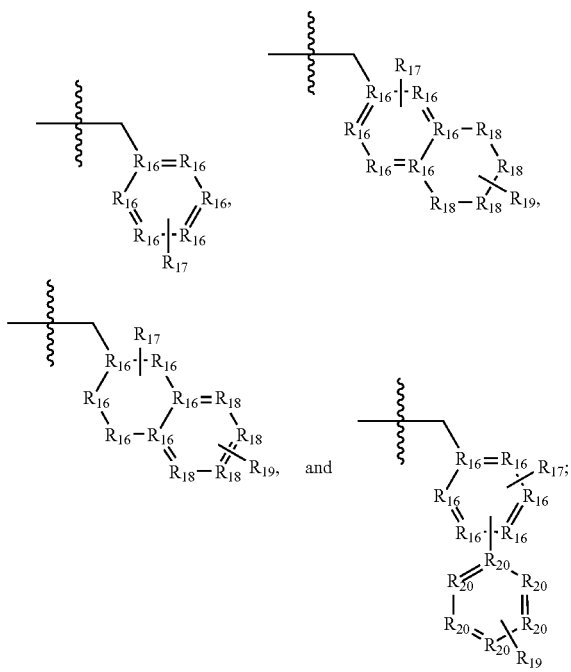

wherein R16 is carbon or nitrogen; wherein R17 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In preferred embodiments, the composition is:

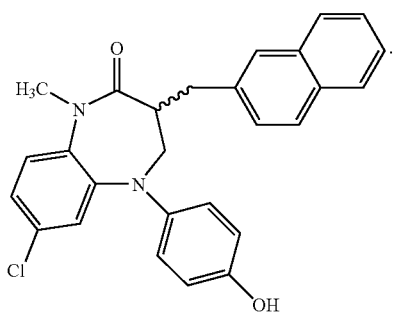

In preferred embodiments, the target cells are selected from the group consisting of in vitro cells, in vivo cells, and ex vivo cells. In other embodiments, the target cells are cancer cells. In yet other embodiments, the target cells are selected from the group consisting of B cells, T cells, and granulocytes.

In certain embodiments, the present invention provides a method for regulating cell death comprising: a) providing: i. target cells having mitochondria; and ii. a composition comprising the following formula:

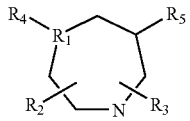

including both R and S enantiomeric forms and racemic mixtures; wherein R1 is a nitrogen atom or a carbon atom; wherein R2 is comprises a chemical moiety comprising a heterocyclic group containing 3 or more carbon atoms; wherein R3 comprises a chemical moiety comprising a heterocyclic group containing 3 or more carbon atoms; and wherein R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and b) exposing the cells to the composition under conditions such that the exposure results in cell death.

In certain embodiments, the present invention provides a composition comprising the following formula:

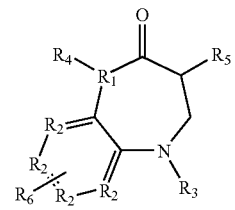

including both R and S enantiomeric forms and racemic mixtures.

In such preferred embodiments, R1 is a nitrogen atom or a carbon atom; R2 is carbon or nitrogen; R3 comprises a chemical moiety comprising a heterocyclic group containing 3 or more carbon atoms; R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and R6 is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and NR'2, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In preferred embodiments, R3 is selected from the group consisting of:

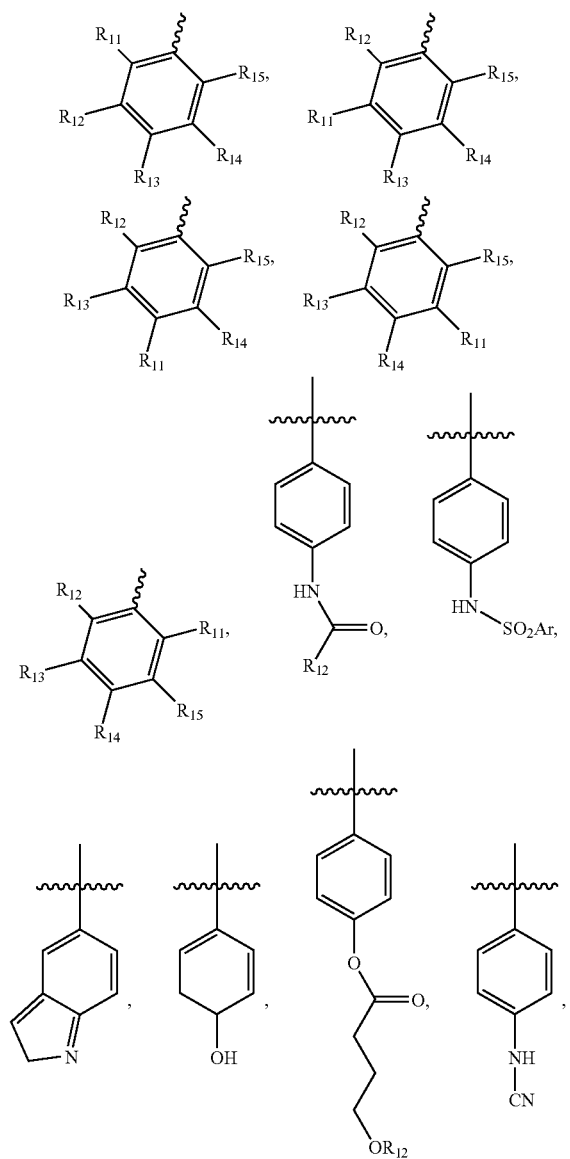

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In preferred embodiments, R4 or R5 are selected from group consisting of: napthalalanine; phenol; 1-Napthalenol; 2-Napthalenol;

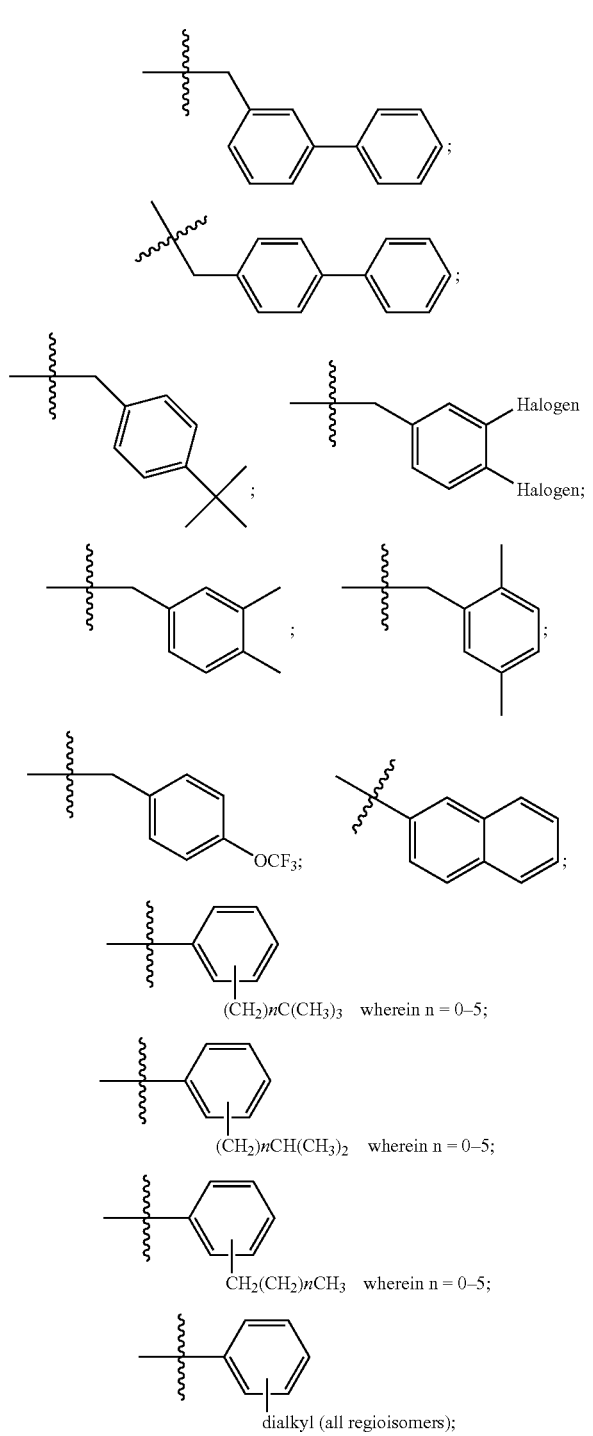

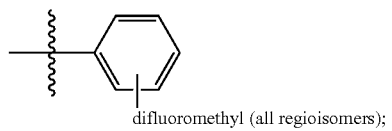

difluoromethyl (all regioisomers);

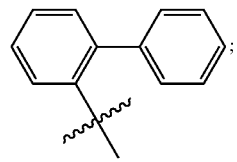

quinolines, and all aromatic regioisomers.

In other preferred embodiments, R4 or R5 is selected from the group consisting of:

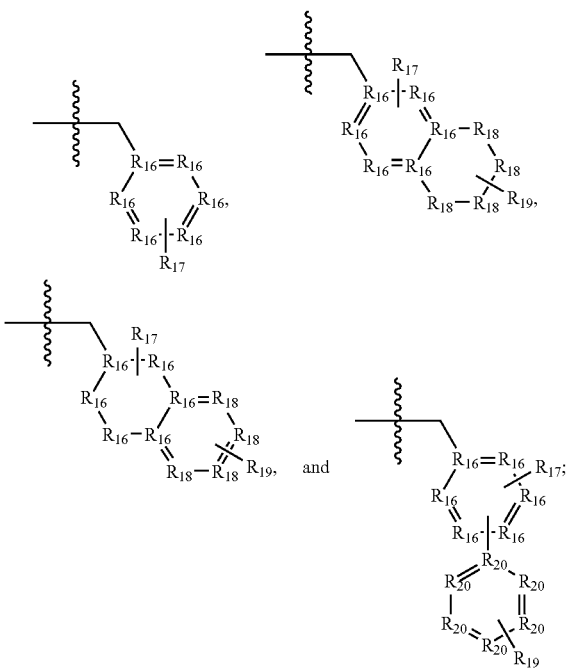

wherein R16 is carbon or nitrogen; wherein R17 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In yet other preferred embodiments, the composition is:

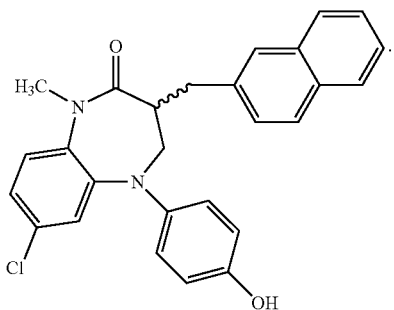

In certain embodiments, the present invention provides a composition comprising the following formula:

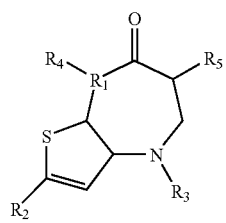

including both R and S enantiomeric forms and racemic mixtures.

In such preferred embodiments, R1 is a nitrogen atom or a carbon atom; R2 is selected from H, a hydroxy, an alkoxy, a halo, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; R3 comprises a chemical moiety comprising a heterocyclic group containing 3 or more carbon atoms; and R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety.

In preferred embodiments, R3 is selected from the group consisting of:

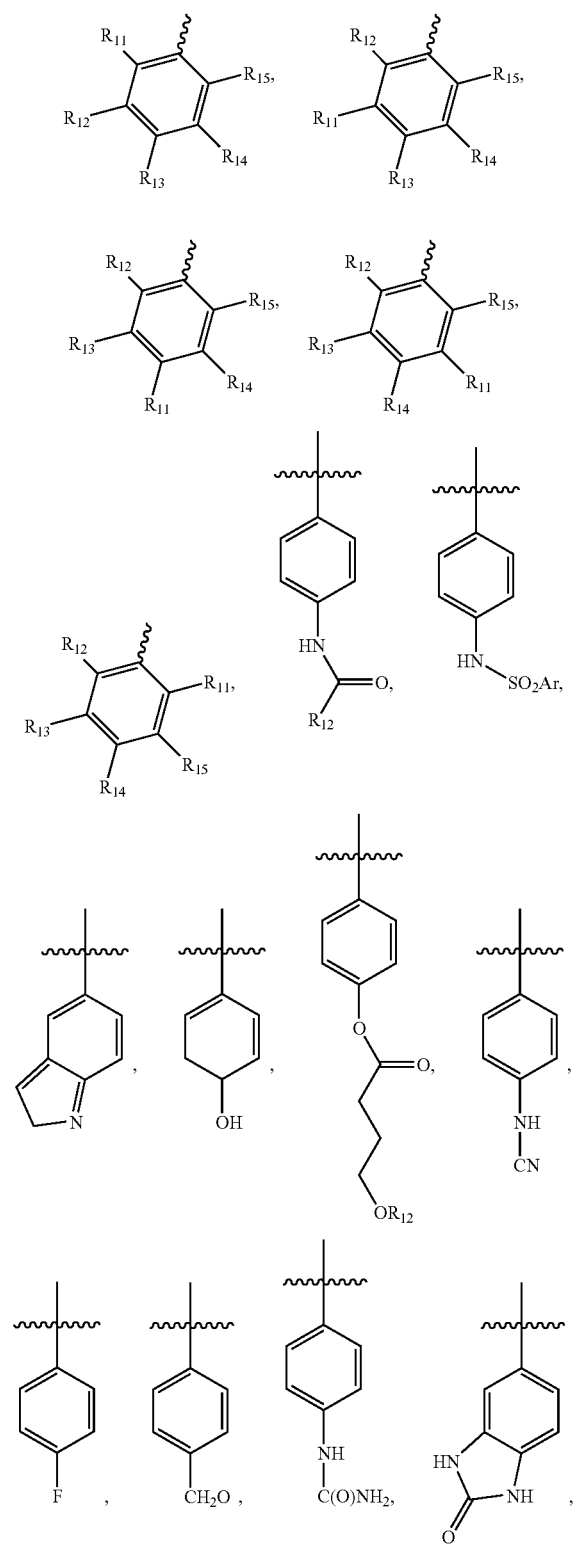

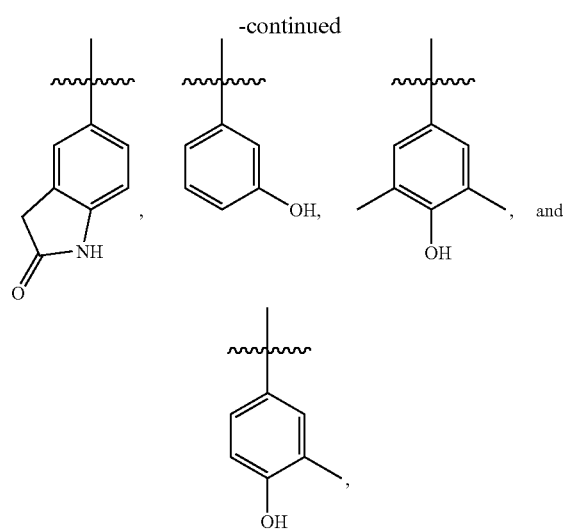

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In preferred embodiments, R4 or R5 are selected from group consisting of: napthalalanine; phenol; 1-Napthalenol; 2-Napthalenol;

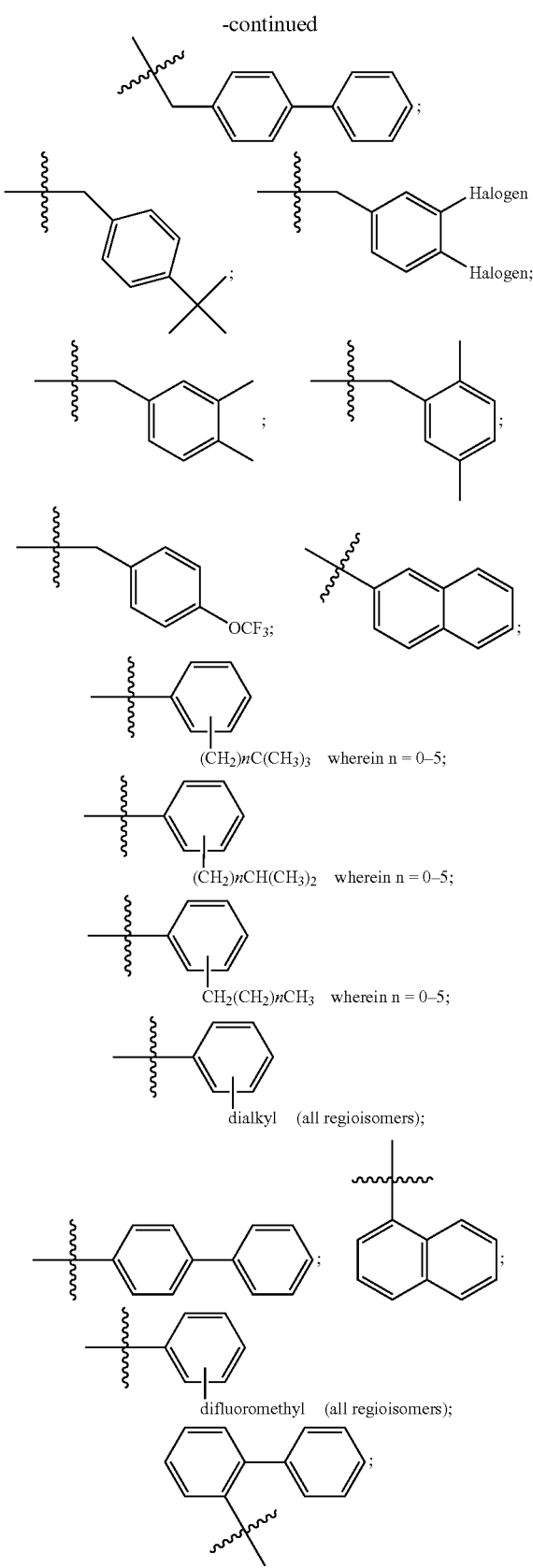

quinolines, and all aromatic regioisomers.

In other preferred embodiments, R4 or R5 is selected from the group consisting of:

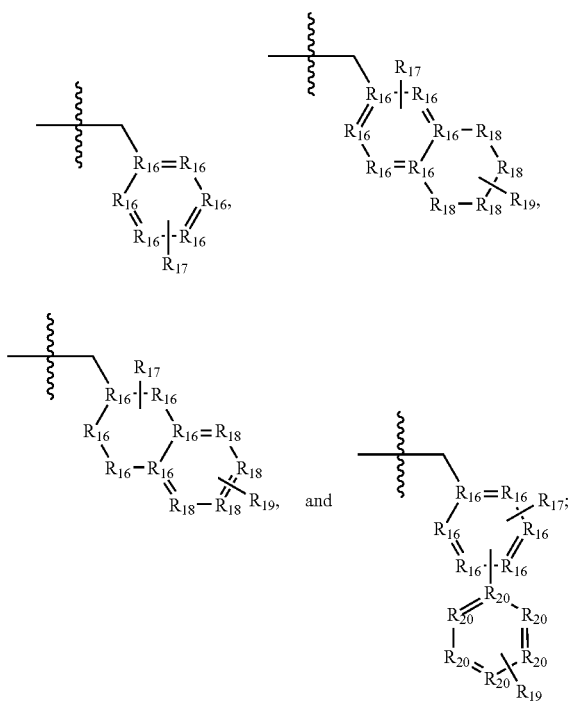

wherein R16 is carbon or nitrogen; wherein R17 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In certain embodiments, the present invention provides a composition comprising the following formula:

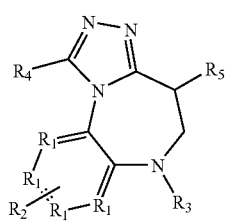

including both R and S enantiomeric forms and racemic mixtures.

In such preferred embodiments, R1 is carbon or nitrogen; R2 is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and NR'$_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; R3 comprises a chemical moiety comprising a heterocyclic group containing 3 or more carbon atoms; R4 is selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and R5 is selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety.

In preferred embodiments, R3 is selected from the group consisting of:

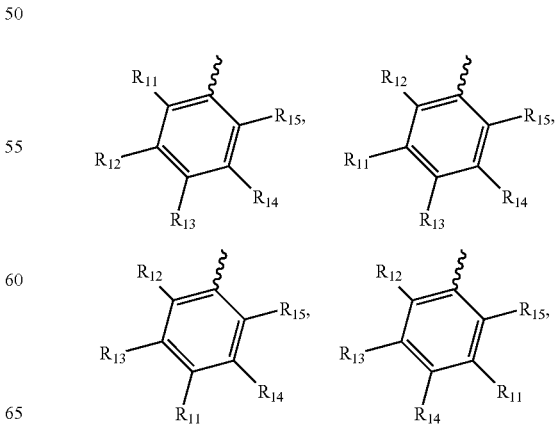

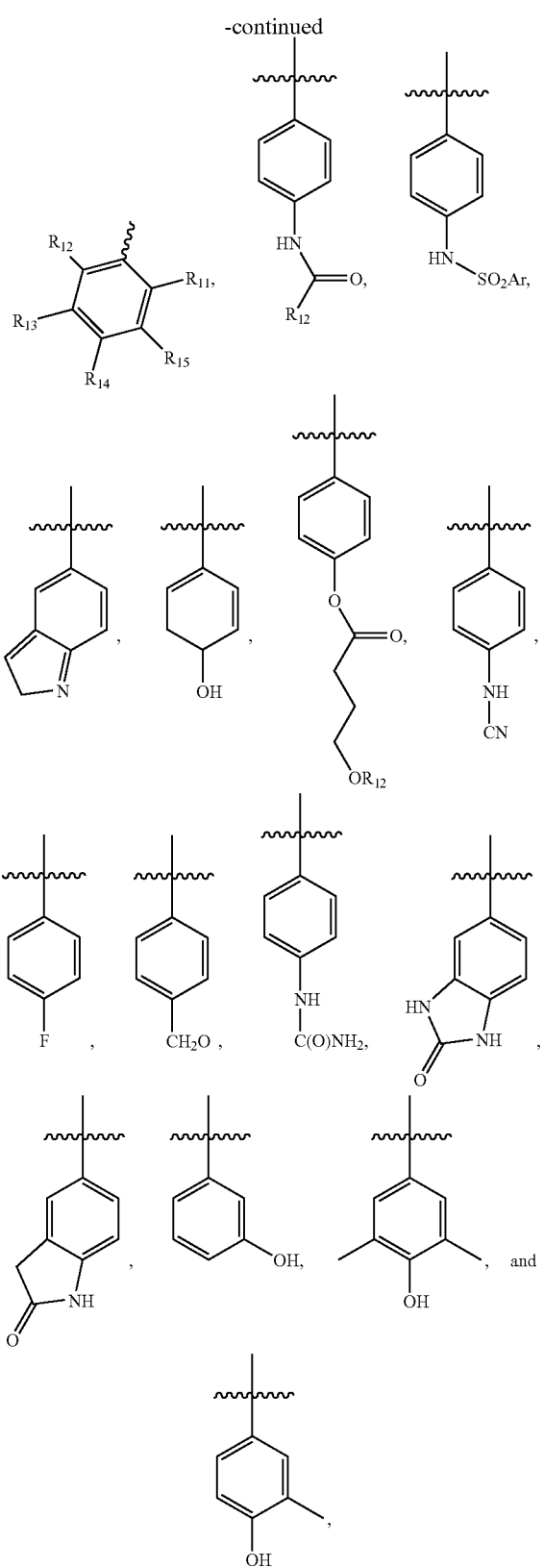

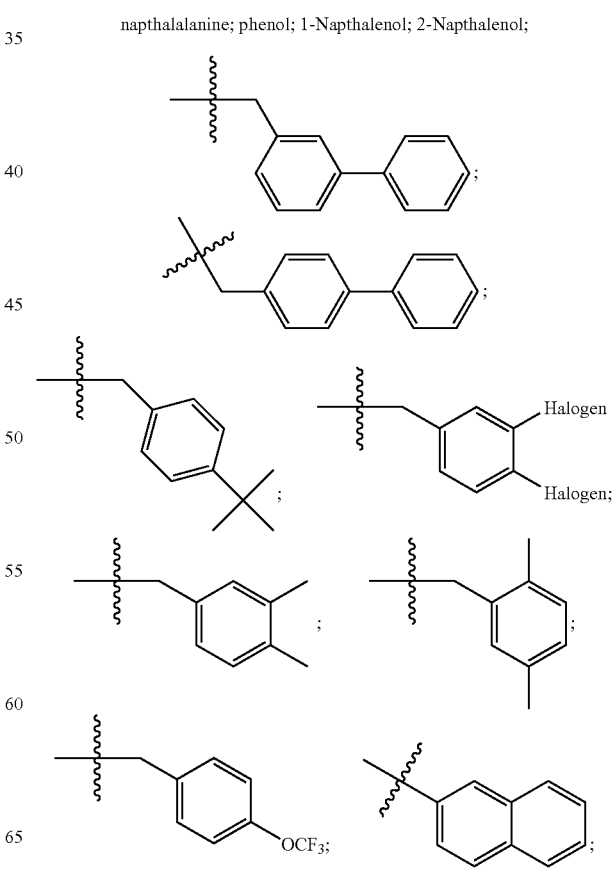

linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In preferred embodiments, R4 or R5 are selected from group consisting of:

napthalalanine; phenol; 1-Napthalenol; 2-Napthalenol;

wherein R12, R13, R14 and R15 are selected from the group consisting of: hydrogen; CH$_3$; a linear or branched, saturated or unsaturated aliphatic chain having at least 1 carbon; a -continued

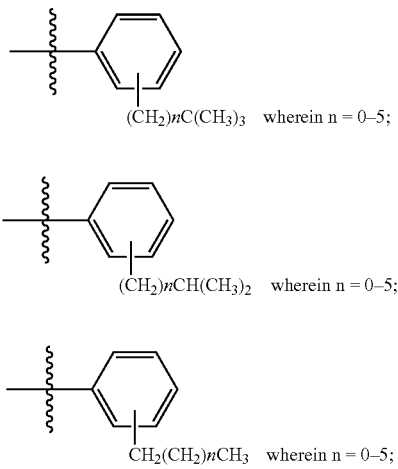

(CH$_2$)$n$C(CH$_3$)$_3$   wherein n = 0–5;

(CH$_2$)$n$CH(CH$_3$)$_2$   wherein n = 0–5;

CH$_2$(CH$_2$)$n$CH$_3$   wherein n = 0–5;

dialkyl (all regioisomers);

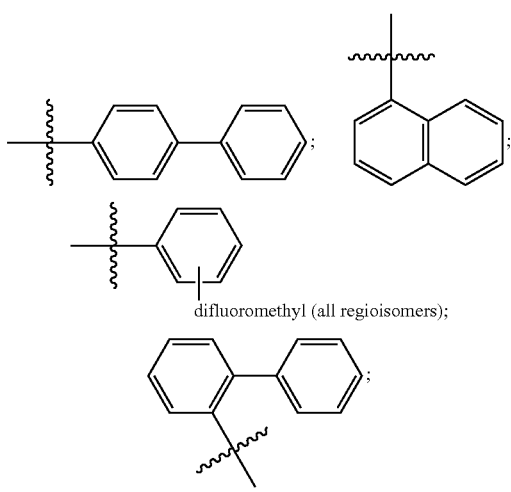

;

difluoromethyl (all regioisomers);

;

quinolines, and all aromatic regioisomers.

In other preferred embodiments, R4 or R5 is selected from the group consisting of:

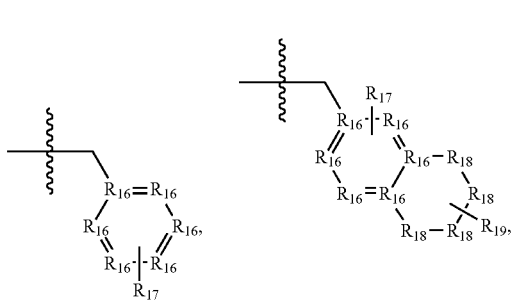

-continued

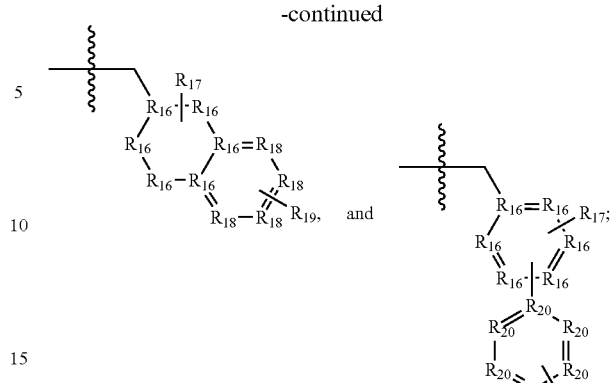

and wherein R16 is carbon or nitrogen; wherein R17 is selected from the group consisting of hydrogen; halogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; halogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In certain embodiments, the present invention provides a method for cell regulation comprising: a. providing: i. target cells having mitochondria; ii. a composition; and exposing the target cells to the composition under conditions such that the exposure results in cell death. In other preferred embodiments, the target cells are exposed to the composition under condition such that the exposure results in cell growth.

In preferred embodiments, the composition binds to the mitochondria so as to increase superoxide levels or alter cellular ATP levels in the target cells. In preferred embodiments, the target cells are selected from the group consisting of in vitro cells, in vivo cells, and ex vivo cells. In preferred embodiments, the target cells are cancer cells. In other preferred embodiments, the target cells are selected from the group consisting of B cells, T cells, transformed cells, and granulocytes.

In preferred embodiments, the composition comprises the following formula:

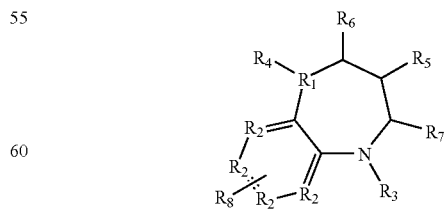

including both R and S enantiomeric forms and racemic mixtures; wherein R1 is a nitrogen atom or a carbon atom; wherein R2 is carbon or nitrogen; wherein R3 comprises a chemical moiety comprising a heterocyclic group containing 3 or more carbon atoms; wherein R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R6 is selected from the group consisting of H and a ketone; wherein R7 is selected from the group consisting of H and a ketone; and wherein R8 is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein said aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein said aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In preferred embodiments, the composition comprises the following formula:

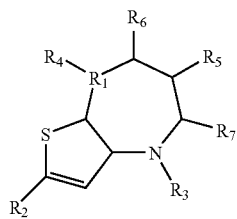

including both R and S enantiomeric forms and racemic mixtures; wherein R1 is a nitrogen atom or a carbon atom; wherein R2 is selected from H, a hydroxy, an alkoxy, a halo, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein said aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein said aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; wherein R3 comprises a chemical moiety comprising a heterocyclic group containing 3 or more carbon atoms; wherein R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R6 is selected from the group consisting of H and a ketone; and wherein R7 is selected from the group consisting of H and a ketone.

In preferred embodiments, the composition comprises the following formula:

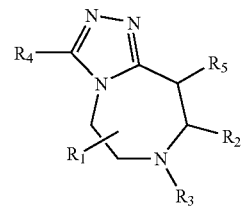

including both R and S enantiomeric forms and racemic mixtures; wherein R1 comprises a chemical moiety comprising a heterocyclic group containing 3 or more carbon atoms; wherein R2 is selected from the group consisting of H and a ketone; wherein R3 comprises a chemical moiety comprising a heterocyclic group containing 3 or more carbon atoms; and wherein R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety.

In preferred embodiments, the composition comprises the following formula:

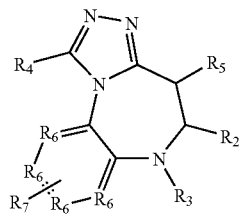

including both R and S enantiomeric forms and racemic mixtures; wherein R1 comprises a chemical moiety comprising a heterocyclic group containing 3 or more carbon atoms; wherein R2 is selected from the group consisting of H and a ketone; wherein R3 comprises a chemical moiety comprising a heterocyclic group containing 3 or more carbon atoms; wherein R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R6 is carbon or nitrogen; and wherein R7 is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein said aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein said aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In certain embodiments, the present invention provides a composition comprising the following formula:

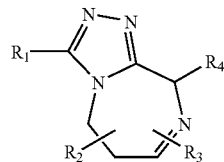

including both R and S enantiomeric forms and racemic mixtures; wherein R1 is selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R2 is comprises a chemical moiety comprising a heterocyclic group containing 3 or more carbon atoms; wherein R3 comprises a chemical moiety comprising a heterocyclic group containing 3 or more carbon atoms; and wherein R4 is selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety.

In preferred embodiments, the composition comprises the formula:

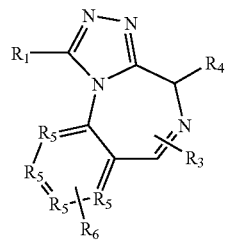

wherein R5 is carbon or nitrogen; and wherein R6 is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In preferred embodiments, R3 is selected from the group consisting of:

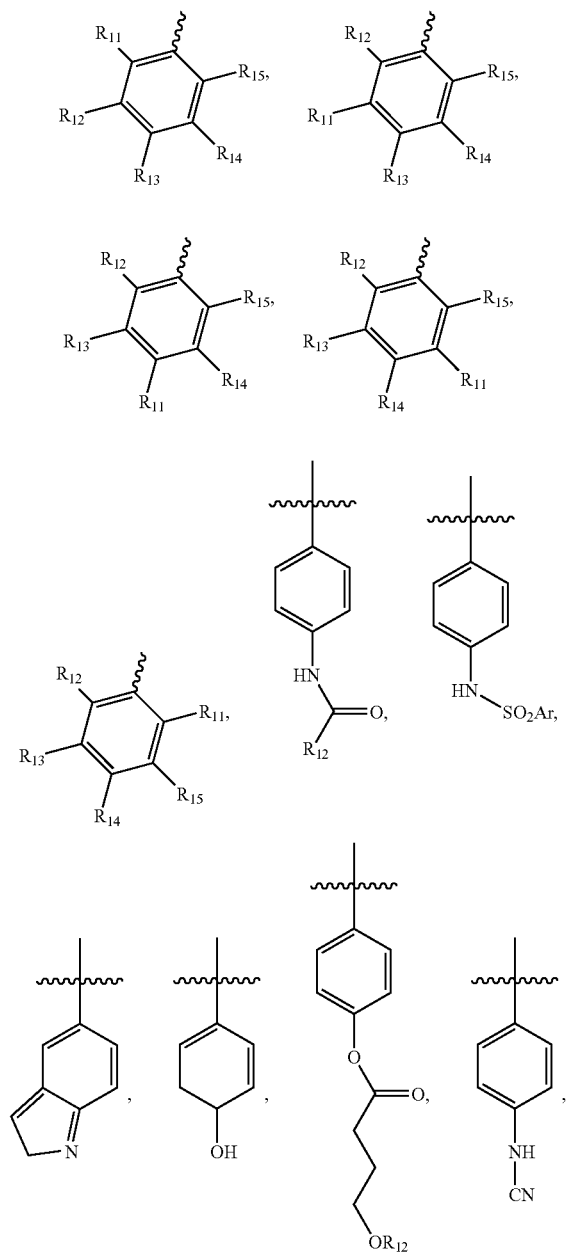

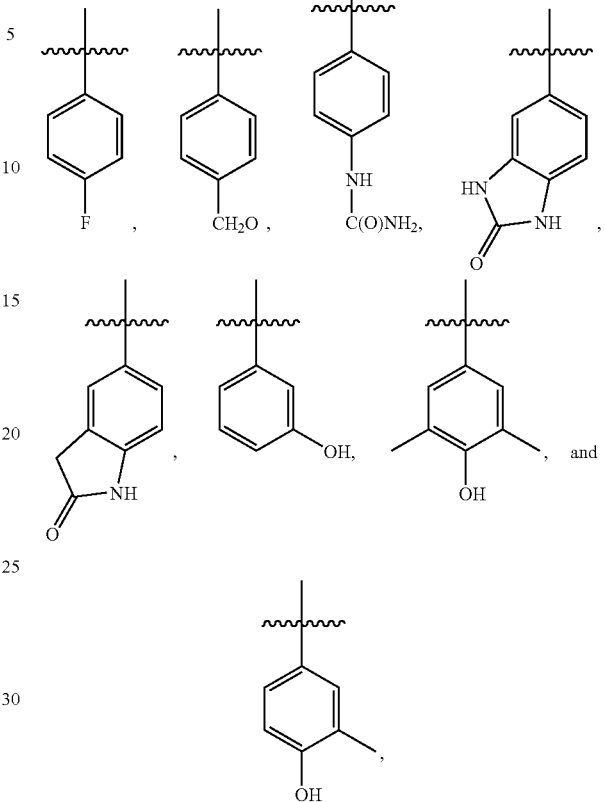

wherein $R_{12}$, $R_{13}$, $R_{14}$ and $R_{15}$ are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and $R_{11}$ is OH.

In other preferred embodiments, R1 or R4 are selected from group consisting of: napthalalanine; phenol; 1-Napthalenol; 2-Napthalenol;

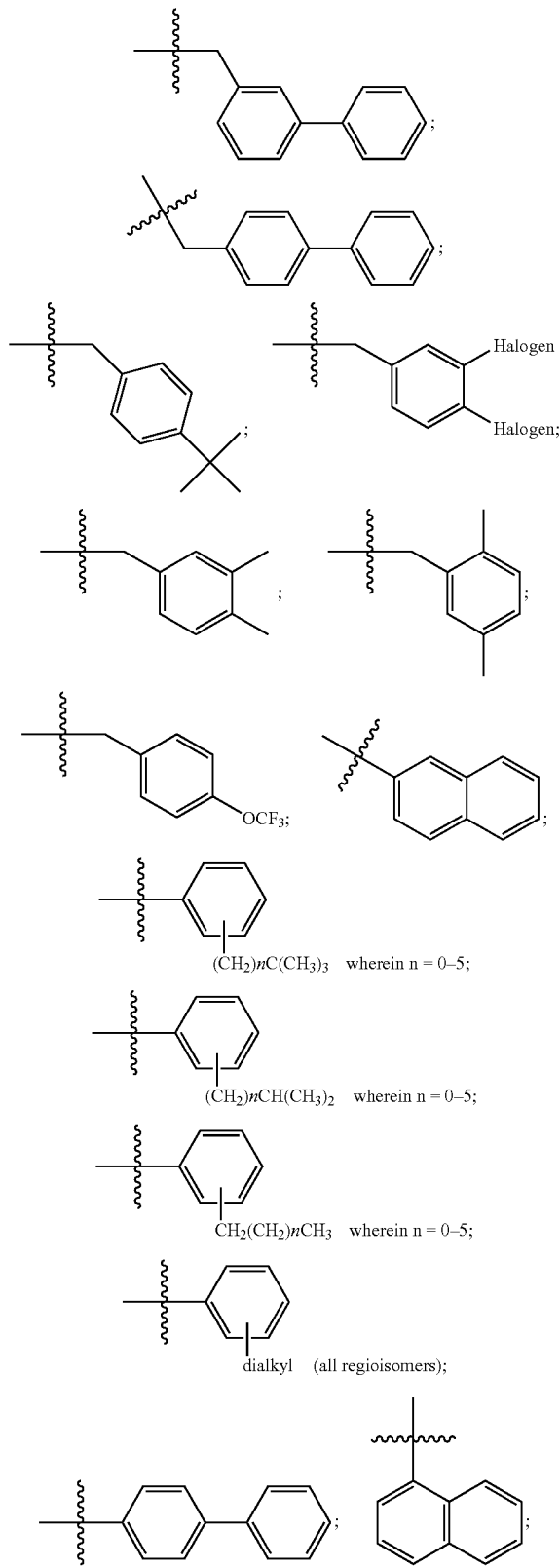

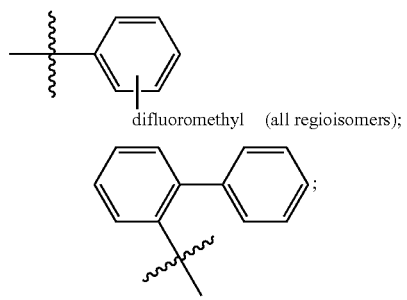

quinolines, and all aromatic regioisomers.

In preferred embodiments, R1 or R5 is selected from the group consisting of: of: napthalalanine; phenol; 1-Napthalenol; 2-Napthalenol;

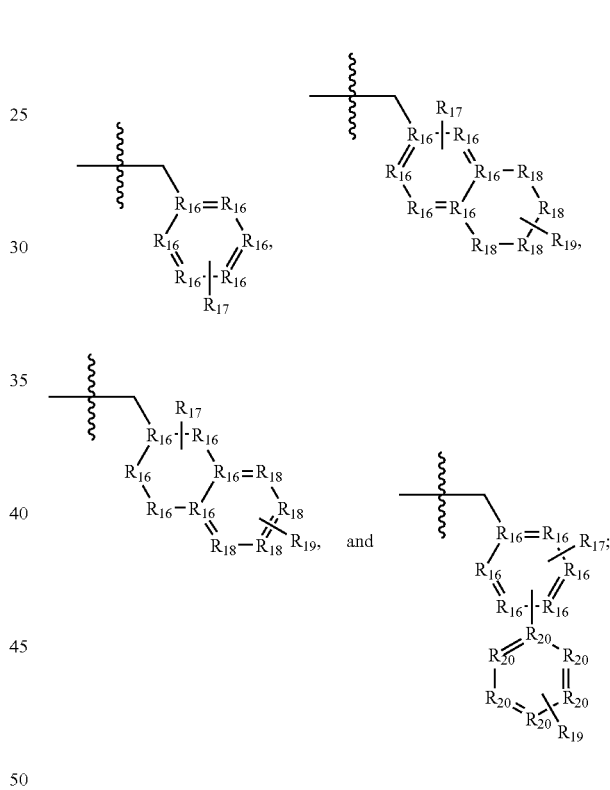

wherein R16 is carbon or nitrogen; wherein R17 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In certain embodiments, the present invention provides a composition comprising the following formula:

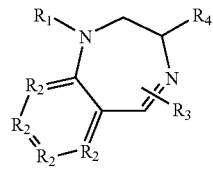

including both R and S enantiomeric forms and racemic mixtures; wherein R1 and R4 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R2 is carbon or nitrogen; and wherein R3 comprises a chemical moiety comprising a heterocyclic group containing 3 or more carbon atoms.

In preferred embodiments, the composition comprises the formula:

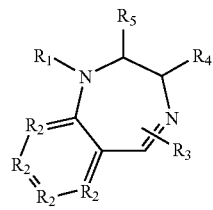

wherein R5 is selected from the group consisting of H and ketone.

In other preferred embodiments, R3 is selected from the group consisting of:

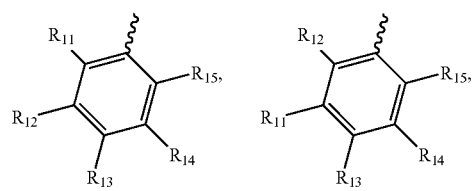

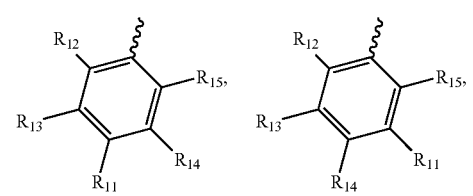

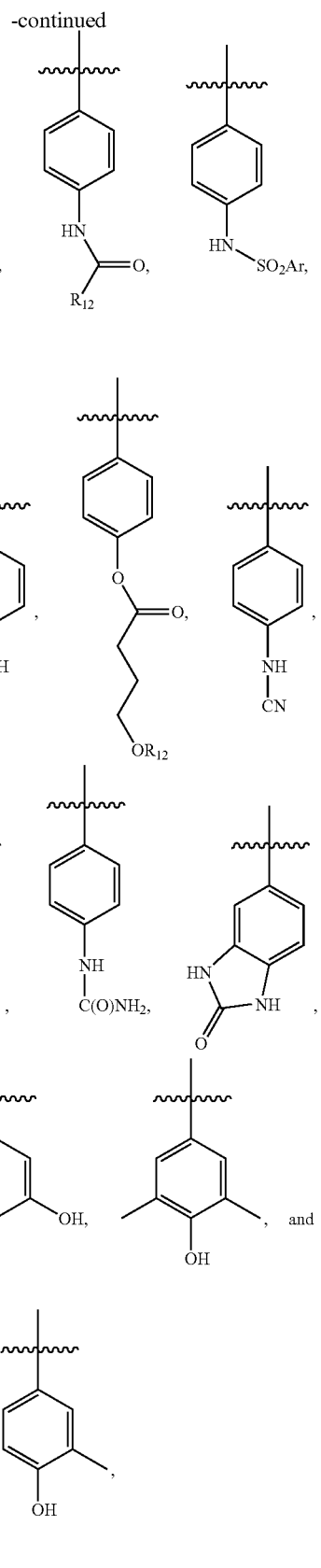

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In yet other preferred embodiments, R1 or R4 is selected from group consisting of: napthalalanine; phenol; 1-Napthalenol; 2-Napthalenol;

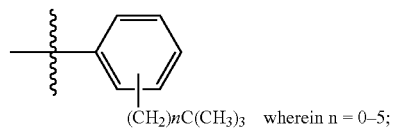

(CH$_2$)$_n$C(CH$_3$)$_3$   wherein n = 0–5;

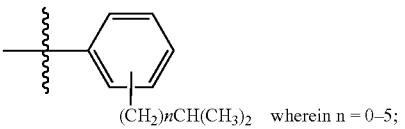

(CH$_2$)$_n$CH(CH$_3$)$_2$   wherein n = 0–5;

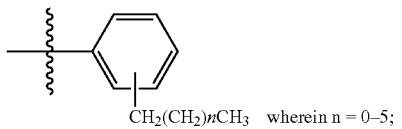

CH$_2$(CH$_2$)$_n$CH$_3$   wherein n = 0–5;

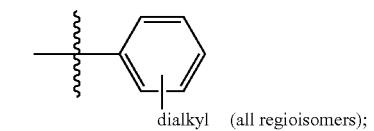

dialkyl   (all regioisomers);

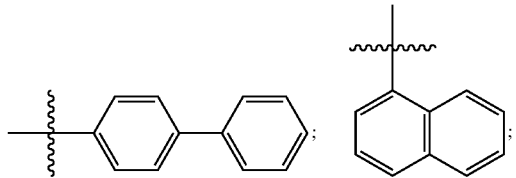

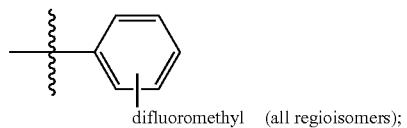

difluoromethyl   (all regioisomers);

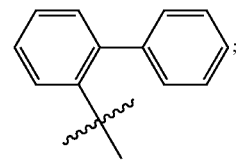

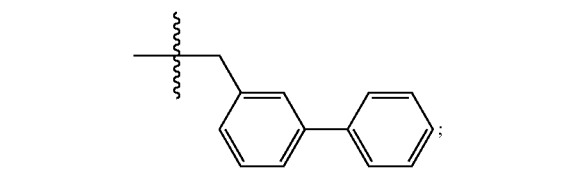

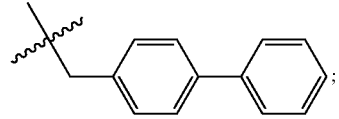

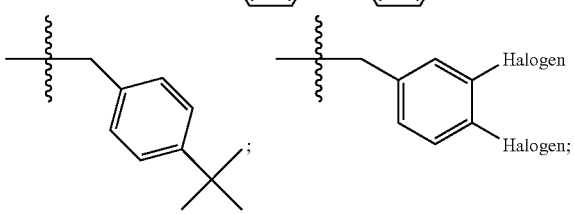

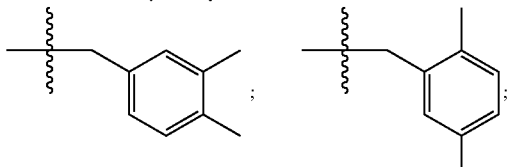

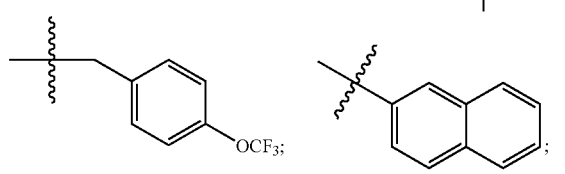

quinolines, and all aromatic regioisomers.

In preferred embodiments, R1 or R4 is selected from the group consisting of:

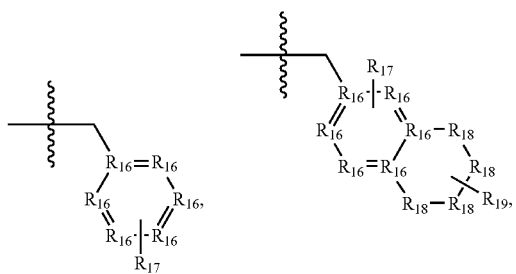

-continued

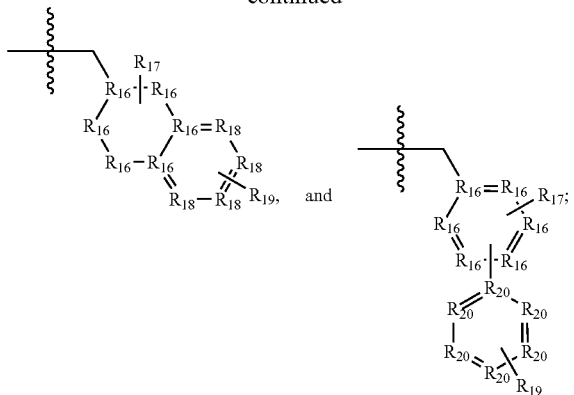

wherein R16 is carbon or nitrogen; wherein R17 is selected from the group consisting of hydrogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In certain embodiments, the present invention provides a composition comprising the following formula:

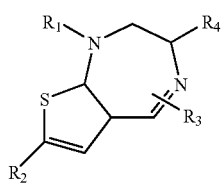

including both R and S enantiomeric forms and racemic mixtures; wherein R1 and R4 are separately selected from the group consisting of: hydrogen; halogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R2 is selected from H, a hydroxy, an alkoxy, a halo, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, NO$_2$; SR'; and NR'$_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and wherein R3 comprises a chemical moiety comprising a heterocyclic group containing 3 or more carbon atoms.

In preferred embodiments, the composition comprises the formula:

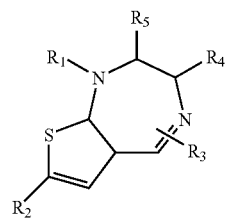

wherein R5 is selected from the group consisting of H and ketone.

In preferred embodiments, R3 is selected from the group consisting of:

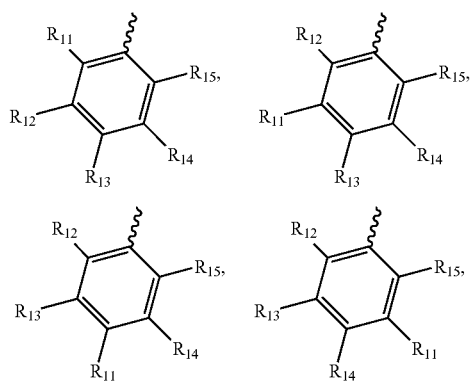

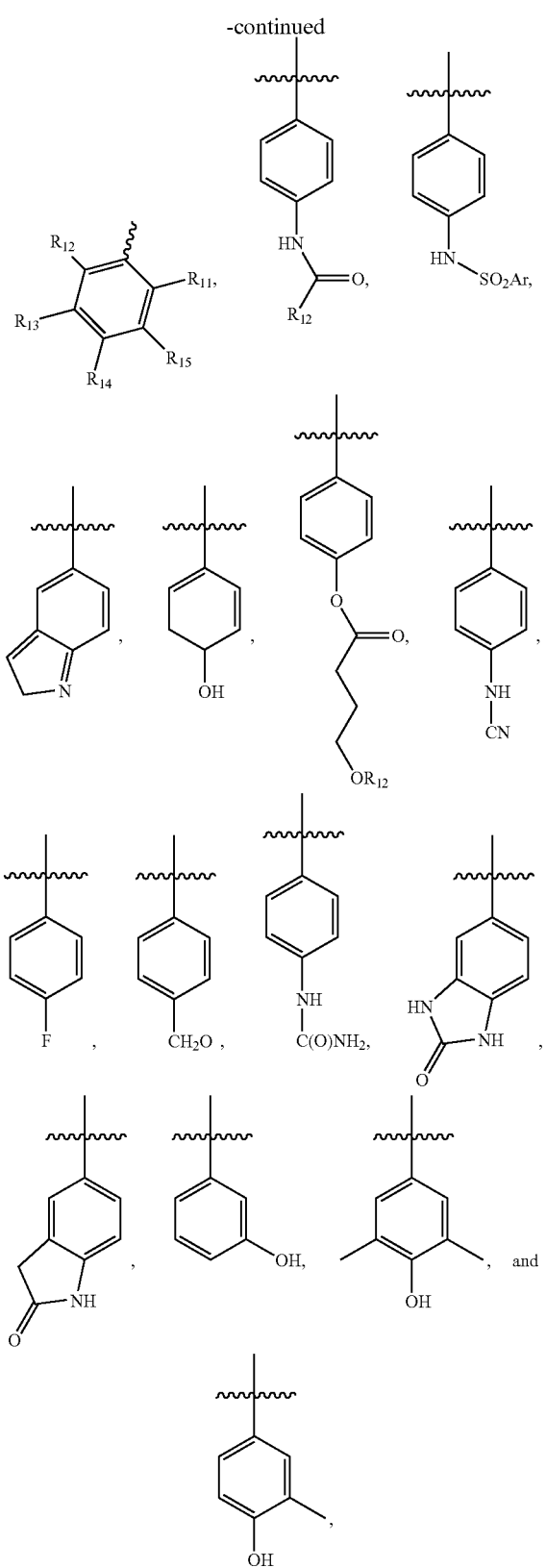

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In other preferred embodiments, R1 or R4 is selected from group consisting of: napthalalanine; phenol; 1-Napthalenol; 2-Napthalenol;

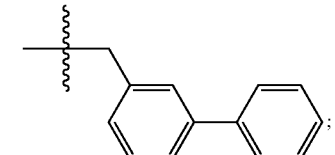

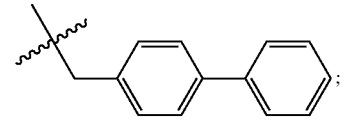

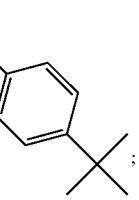 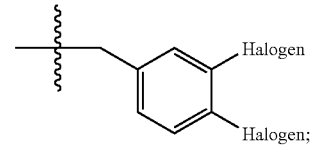

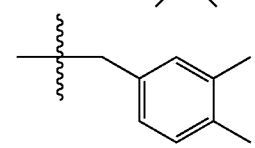 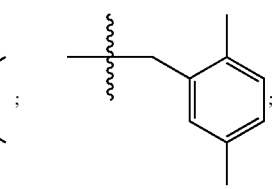

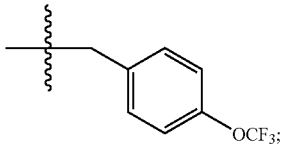 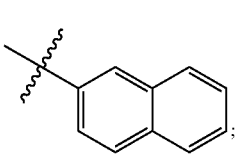

-continued

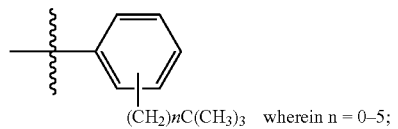

(CH₂)nC(CH₃)₃  wherein n = 0–5;

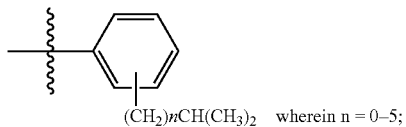

(CH₂)nCH(CH₃)₂  wherein n = 0–5;

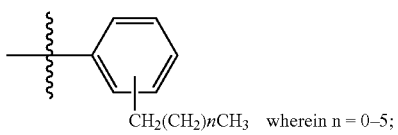

CH₂(CH₂)nCH₃  wherein n = 0–5;

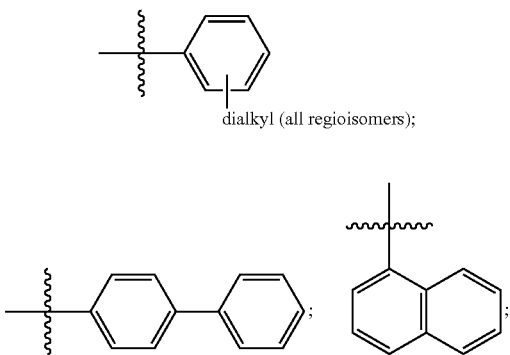

dialkyl (all regioisomers);

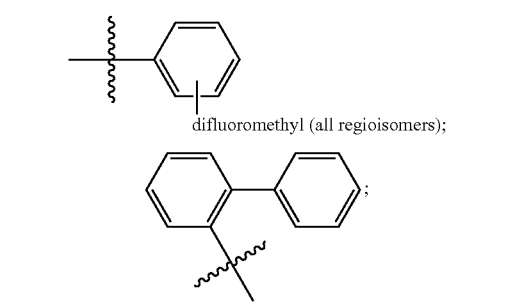

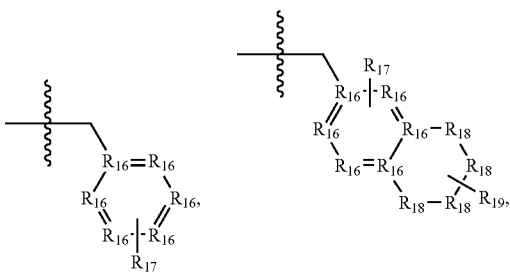

difluoromethyl (all regioisomers);

quinolines, and all aromatic regioisomers.

In preferred embodiments, R1 or R4 is selected from the group consisting of:

-continued

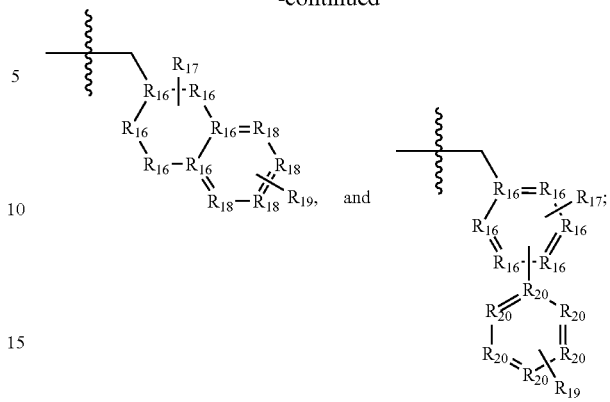

wherein R16 is carbon or nitrogen; wherein R17 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

DEFINITIONS

Figure 1:
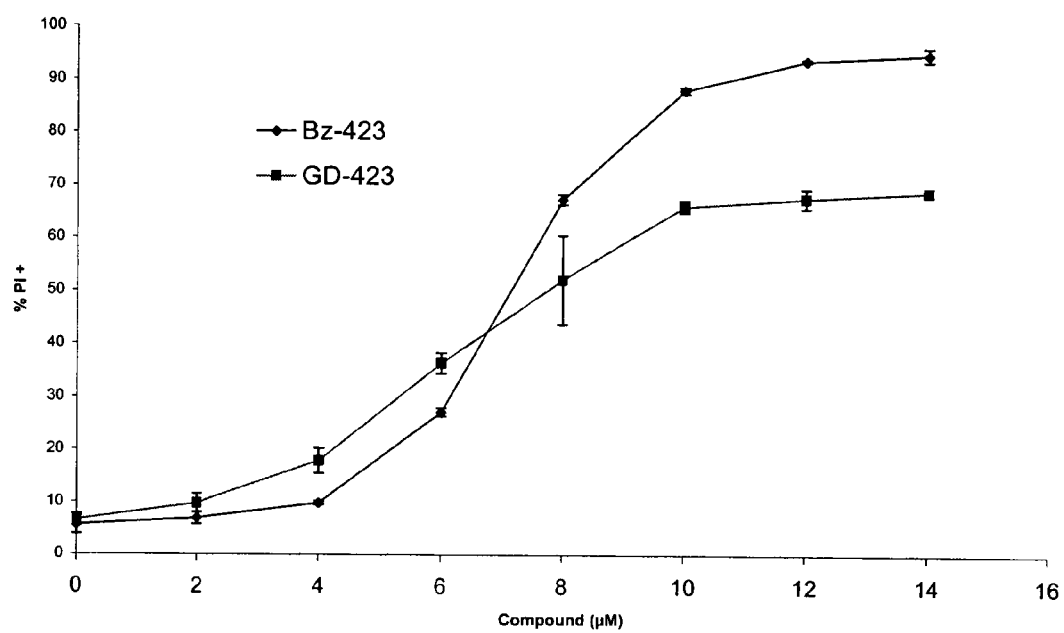
FIG. 1 shows data demonstrating that GD-423 causes cell death.

To facilitate an understanding of the present invention, a number of terms and phrases are defined below.

As used herein, the term "benzodiazepine" refers to a seven membered non-aromatic heterocyclic ring fused to a phenyl ring wherein the seven-membered ring has two nitrogen atoms, as part of the heterocyclic ring. In some aspects, the two nitrogen atoms are in 1 and 5 positions or 1 and 4 positions, as shown in the general structures below:

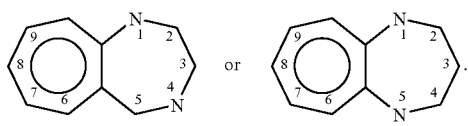

The term "larger than benzene" refers to any chemical group containing 7 or more non-hydrogen atoms.

The term "chemical moiety" refers to any chemical compound containing at least one carbon atom. Examples of chemical moieties include, but are not limited to, aromatic chemical moieties, chemical moieties comprising Sulfur, chemical moieties comprising Nitrogen, hydrophilic chemical moieties, and hydrophobic chemical moieties.

As used herein, the term "aliphatic" represents the groups including, but not limited to, alkyl, alkenyl, alkynyl, alicyclic.

As used herein, the term "aryl" represents a single aromatic ring such as a phenyl ring, or two or more aromatic rings (e.g., bisphenyl, naphthalene, anthracene), or an aromatic ring and one or more non-aromatic rings. The aryl group can be optionally substituted with a lower aliphatic group (e.g., alkyl, alkenyl, alkynyl, or alicyclic). Additionally, the aliphatic and aryl groups can be further substituted by one or more functional groups including, but not limited to, —NH$_2$, —NHCOCH$_3$, —OH, lower alkoxy (C$_1$-C$_4$), halo (—F, —Cl, —Br, or —I).

As used herein, the term "substituted aliphatic" refers to an alkane possessing where at least one of the aliphatic hydrogen atoms has been replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic, etc.). Examples of such include, but are not limited to, 1-chloroethyl and the like.

As used herein, the term "substituted aryl" refers to an aryl group where at least one of the hydrogen atoms on a ring carbon is replaced by, for example, a halogen, an amino, a hydroxy, a nitro, a thio, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, hydroxyphenyl and the like.

As used herein, the term "cycloaliphatic" refers to a cycloalkane possessing 3 or more carbons or a fused ring. Examples of such include, but are not limited to, decalin and the like.

As used herein, the term "substituted cycloaliphatic" refers to a cycloalkane possessing 3 or more carbons or a fused ring system consisting of two or more fused rings, and where at least one of the aliphatic hydrogen atoms has been replaced by, for example, a halogen, a nitro, a thio, an amino, a hydroxy, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 1-chlorodecalyl, bicyclo-heptanes, octanes, and nonanes (e.g., nonrbornyl) and the like.

As used herein, the term "heterocyclic" represents, for example, an aromatic or nonaromatic ring containing one or more heteroatoms. The heteroatoms can be the same or different from each other. Examples of heteratoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole. The heterocyclic ring is optionally further substituted with one or more groups selected from aliphatic, nitro, acetyl (i.e., —C(=O)—CH$_3$), or aryl groups.

As used herein, the term "substituted heterocyclic" refers to a cycloalkane, an aryl ring system, and/or a fused ring system where at least one of the ring carbon atoms is replaced by, for example, oxygen, nitrogen or sulfur, and where at least one of the aliphatic hydrogen atoms has been replaced by, for example, a halogen, hydroxy, a thio, nitro, an amino, a ketone, an aldehyde, an ester, an amide, a lower aliphatic, a substituted lower aliphatic, or a ring (aryl, substituted aryl, cycloaliphatic, or substituted cycloaliphatic). Examples of such include, but are not limited to, 2-chloropyranyl.

As used herein, the term "a moiety that participates in hydrogen bonding" as used herein represents a group that can accept or donate a proton to form a hydrogen bond thereby. Some specific non-limiting examples of moieties that participate in hydrogen bonding include a fluoro, oxygen-containing and nitrogen-containing groups that are well-known in the art. Some examples of oxygen-containing groups that participate in hydrogen bonding include: hydroxy, lower alkoxy, lower carbonyl, lower carboxyl, lower ethers and phenolic groups. The qualifier "lower" as used herein refers to lower aliphatic groups (C$_1$-C$_4$) to which the respective oxygen-containing functional group is attached. Thus, for example, the term "lower carbonyl" refers to inter alia, formaldehyde, acetaldehyde. Some nonlimiting examples of nitrogen-containing groups that participate in hydrogen bond formation include amino and amido groups. Additionally, groups containing both an oxygen and a nitrogen atom can also participate in hydrogen bond formation. Examples of such groups include nitro, N-hydroxy and nitrous groups. It is also possible that the hydrogen-bond acceptor in the present invention can be the π electrons of an aromatic ring.

As used herein, the term "lower-alkyl-substituted-amino" refers to any alkyl unit containing up to and including eight carbon atoms where one of the aliphatic hydrogen atoms is replaced by an amino group. Examples of such include, but are not limited to, ethylamino and the like.

As used herein, the term "lower-alkyl-substituted-halogen" refers to any alkyl chain containing up to and including eight carbon atoms where one of the aliphatic hydrogen atoms is replaced by a halogen. Examples of such include, but are not limited to, chlorethyl and the like.

As used herein, the term "acetylamino" shall mean any primary or secondary amino that is acetylated. Examples of such include, but are not limited to, acetamide and the like.

The term "derivative" of a compound, as used herein, refers to a chemically modified compound wherein the chemical modification takes place either at a functional group of the compound or on the aromatic ring.

The term "epidermal hyperplasia," as used herein, refers to an abnormal multiplication or increase in the number of normal cells in normal arrangement in epidermal tissue. Epidermal hyperplasia is a characteristic of numerous disorders, including but not limited to, psoriasis.

The term "keratinocyte" as used herein, refers to a skin cell of the keratinized layer of the epidermis.

The term "fibroblast" as used herein, refers to mesodermally derived resident cells of connective tissue that secrete fibrillar procollagen, fibronectin and collegenase.

The term "stent" or "drug-eluting stent," as used herein, refers to any device which when placed into contact with a site in the wall of a lumen to be treated, will also place fibrin at the lumen wall and retain it at the lumen wall. This can include especially devices delivered percutaneously to treat coronary artery occlusions and to seal dissections or aneurysms of splenic, carotid, iliac and popliteal vessels. The stent can also have underlying polymeric or metallic structural elements onto which the fibrin is applied or the stent can be a composite of fibrin intermixed with a polymer. For example, a deformable metal wire stent such as that disclosed in U.S. Pat. No. 4,886,062, herein incorporated by reference, could be coated with fibrin as set forth above in one or more coats (i.e., polymerization of fibrin on the metal framework by application of a fibrinogen solution and a solution of a fibrinogen-coagulating protein) or provided with an attached fibrin preform such as an encircling film of fibrin. The stent and fibrin could then be placed onto the balloon at a distal end of a balloon catheter and delivered by conventional percutaneous means (e.g. as in an angioplasty procedure) to the site of the restriction or closure to be treated where it would then be expanded into contact with the body lumen by inflating the balloon. The catheter can then be withdrawn, leaving the fibrin stent of the present invention in place at the treatment site. The stent may therefore provide both a supporting structure for the lumen at the site of treatment and also a structure supporting the secure placement of fibrin at the lumen wall. Generally, a drug-eluting stent allows for an active release of a particular drug at the stent implementation site.

As used herein, the term "catheter" refers generally to a tube used for gaining access to a body cavity or blood vessel.

As used herein, the term "valve" or "vessel" refers to any lumen within a mammal. Examples include, but are not limited to, arteries, veins, capillaries, and biological lumen.

As used herein, the term "restenosis" refers to any valve which is narrowed. Examples include, but are not limited to, the reclosure of a peripheral or coronary artery following trauma to that artery caused by efforts to open a stenosed portion of the artery, such as, for example, by balloon dilation, ablation, atherectomy or laser treatment of the artery.

As used herein, "angioplasty" or "balloon therapy" or "balloon angioplasty" or "percutaneous transluminal coronary angioplasty" refers to a method of treating blood vessel disorders that involves the use of a balloon catheter to enlarge the blood vessel and thereby improve blood flow.

As used herein, "cardiac catheterization" or "coronary angiogram" refers to a test used to diagnose coronary artery disease using a catheterization procedure. Such a procedure may involve, for example, the injection of a contrast dye into the coronary arteries via a catheter, permitting the visualization of a narrowed or blocked artery.

As used herein, the term "subject" refers to organisms to be treated by the methods of the present invention. Such organisms preferably include, but are not limited to, mammals (e.g., murines, simians, equines, bovines, porcines, canines, felines, and the like), and most preferably includes humans. In the context of the invention, the term "subject" generally refers to an individual who will receive or who has received treatment (e.g., administration of a compound of the present invention and optionally one or more other agents) for a condition characterized by the dysregulation of apoptotic processes.

The term "diagnosed," as used herein, refers to the to recognition of a disease by its signs and symptoms (e.g., resistance to conventional therapies), or genetic analysis, pathological analysis, histological analysis, and the like.

As used herein, the terms "anticancer agent," or "conventional anticancer agent" refer to any chemotherapeutic compounds, radiation therapies, or surgical interventions, used in the treatment of cancer.

As used herein the term, "in vitro" refers to an artificial environment and to processes or reactions that occur within an artificial environment. In vitro environments include, but are not limited to, test tubes and cell cultures. The term "in vivo" refers to the natural environment (e.g., an animal or a cell) and to processes or reaction that occur within a natural environment.

As used herein, the term "host cell" refers to any eukaryotic or prokaryotic cell (e.g., mammalian cells, avian cells, amphibian cells, plant cells, fish cells, and insect cells), whether located in vitro or in vivo.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

In preferred embodiments, the "target cells" of the compositions and methods of the present invention include, refer to, but are not limited to, lymphoid cells or cancer cells. Lymphoid cells include B cells, T cells, and granulocytes. Granulocytes include eosinophils and macrophages. In some embodiments, target cells are continuously cultured cells or uncultured cells obtained from patient biopsies.

Cancer cells include tumor cells, neoplastic cells, malignant cells, metastatic cells, and hyperplastic cells. Neoplastic cells can be benign or malignant. Neoplastic cells are benign if they do not invade or metastasize. A malignant cell is one that is able to invade and/or metastasize. Hyperplasia is a pathologic accumulation of cells in a tissue or organ, without significant alteration in structure or function.

In one specific embodiment, the target cells exhibit pathological growth or proliferation. As used herein, the term "pathologically proliferating or growing cells" refers to a localized population of proliferating cells in an animal that is not governed by the usual limitations of normal growth.

As used herein, the term "un-activated target cell" refers to a cell that is either in the $G_o$ phase or one in which a stimulus has not been applied.

As used herein, the term "activated target lymphoid cell" refers to a lymphoid cell that has been primed with an appropriate stimulus to cause a signal transduction cascade, or alternatively, a lymphoid cell that is not in $G_o$ phase. Activated lymphoid cells may proliferate, undergo activation induced cell death, or produce one or more of cytotoxins, cytokines, and other related membrane-associated proteins characteristic of the cell type (e.g., $CD8^+$ or $CD4^+$). They are also capable of recognizing and binding any target cell that displays a particular antigen on its surface, and subsequently releasing its effector molecules.

As used herein, the term "activated cancer cell" refers to a cancer cell that has been primed with an appropriate stimulus to cause a signal transduction. An activated cancer cell may or may not be in the $G_O$ phase.

An activating agent is a stimulus that upon interaction with a target cell results in a signal transduction cascade. Examples of activating stimuli include, but are not limited to, small molecules, radiant energy, and molecules that bind to cell activation cell surface receptors. Responses induced by activation stimuli can be characterized by changes in, among others, intracellular $Ca^{2+}$, superoxide, or hydroxyl radical levels; the activity of enzymes like kinases or phosphatases; or the energy state of the cell. For cancer cells, activating agents also include transforming oncogenes.

In one aspect, the activating agent is any agent that binds to a cell surface activation receptor. These can be selected from the group consisting of a T cell receptor ligand, a B cell activating factor ("BAFF"), a TNF, a Fas ligand (FasL), a CD40 ligand, a proliferation inducing ligand ("APRIL"), a cytokine, a chemokine, a hormone, an amino acid (e.g., glutamate), a steroid, a B cell receptor ligand, gamma irradiation, UV irradiation, an agent or condition that enhances cell stress, or an antibody that specifically recognizes and binds a cell surface activation receptor (e.g., anti-CD4, anti-CD8, anti-CD20, anti-TACI, anti-BCMA, anti-TNF receptor, anti-CD40, anti-CD3, anti-CD28, anti-B220, anti-CD38, and-CD19, and anti-CD21). BCMA is B cell maturation antigen receptor and TACI is transmembrane activator and CAML interactor. (Gross, A. et al. (2000); Laabi, Y et al. (1992) and Madry, C. et al. (1998)). Antibodies include monoclonal or polyclonal or a mixture thereof.

Examples of a T cell ligand include, but are not limited to, a peptide that binds to an MHC molecule, a peptide MHC complex, or an antibody that recognizes components of the T cell receptor.

Examples of a B cell ligand include, but are not limited to, a molecule or antibody that binds to or recognizes components of the B cell receptor.

Examples of reagents that bind to a cell surface activation receptor include, but are not limited to, the natural ligands of these receptors or antibodies raised against them (e.g., anti-CD20). RITUXIN (Genentech, Inc., San Francisco, Calif.) is a commercially available anti-CD 20 chimeric monoclonal antibody.

Examples of agents or conditions that enhance cell stress include heat, radiation, oxidative stress, or growth factor withdrawal and the like. Examples of growth factors include, but are not limited to serum, IL-2, platelet derived growth factor ("PDGF"), and the like.

As used herein, the term "effective amount" refers to the amount of a compound (e.g., a compound of the present invention) sufficient to effect beneficial or desired results. An effective amount can be administered in one or more administrations, applications or dosages and is not limited intended to be limited to a particular formulation or administration route.

As used herein, the term "dysregulation of the process of cell death" refers to any aberration in the ability of (e.g., predisposition) a cell to undergo cell death via either necrosis or apoptosis. Dysregulation of cell death is associated with or induced by a variety of conditions, including for example, autoimmune disorders (e.g., systemic lupus erythematosus, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes, papilloma, HIV), and other conditions such as osteoarthritis and atherosclerosis.

It should be noted that when the dysregulation is induced by or associated with a viral infection, the viral infection may or may not be detectable at the time dysregulation occurs or is observed. That is, viral-induced dysregulation can occur even after the disappearance of symptoms of viral infection.

A "hyperproliferative disorder," as used herein refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo, invasion or metastasis and malignant if it does either of these. A metastatic cell or tissue means that the cell can invade and destroy neighboring body structures. Hyperplasia is a form of cell proliferation involving an increase in cell number in a tissue or organ, without significant alteration in structure or function. Metaplasia is a form of controlled cell growth in which one type of fully differentiated cell substitutes for another type of differentiated cell. Metaplasia can occur in epithelial or connective tissue cells. A typical metaplasia involves a somewhat disorderly metaplastic epithelium.

The pathological growth of activated lymphoid cells often results in an autoimmune disorder or a chronic inflammatory condition. As used herein, the term "autoimmune disorder" refers to any condition in which an organism produces antibodies or immune cells which recognize the organism's own molecules, cells or tissues. Non-limiting examples of autoimmune disorders include autoimmune hemolytic anemia, autoimmune hepatitis, Berger's disease or IgA nephropathy, Celiac Sprue, chronic fatigue syndrome, Crohn's disease, dermatomyositis, fibromyalgia, graft versus host disease, Grave's disease, Hashimoto's thyroiditis, idiopathic thrombocytopenia purpura, lichen planus, multiple sclerosis, myasthenia gravis, psoriasis, rheumatic fever, rheumatic arthritis, scleroderma, Sjorgren syndrome, systemic lupus erythematosus, type 1 diabetes, ulcerative colitis, vitiligo, and the like.

As used herein, the term "chronic inflammatory condition" refers to a condition wherein the organism's immune cells are activated. Such a condition is characterized by a persistent inflammatory response with pathologic sequelae. This state is characterized by infiltration of mononuclear cells, proliferation of fibroblasts and small blood vessels, increased connective tissue, and tissue destruction. Examples of chronic inflammatory diseases include, but are not limited to, Crohn's disease, psoriasis, chronic obstructive pulmonary disease, inflammatory bowel disease, multiple sclerosis, and asthma. Autoimmune diseases such as rheumatoid arthritis and systemic lupus erythematosus can also result in a chronic inflammatory state.

As used herein, the term "co-administration" refers to the administration of at least two agent(s) (e.g., a compound of the present invention) or therapies to a subject. In some embodiments, the co-administration of two or more agents/therapies is concurrent. In other embodiments, a first agent/therapy is administered prior to a second agent/therapy. Those of skill in the art understand that the formulations and/or routes of administration of the various agents/therapies used may vary. The appropriate dosage for co-administration can be readily determined by one skilled in the art. In some embodiments, when agents/therapies are co-administered, the respective agents/therapies are administered at lower dosages than appropriate for their administration alone. Thus, co-administration is especially desirable in embodiments where the co-administration of the agents/therapies lowers the requisite dosage of a known potentially harmful (e.g., toxic) agent(s).

As used herein, the term "toxic" refers to any detrimental or harmful effects on a cell or tissue as compared to the same cell or tissue prior to the administration of the toxicant.

As used herein, the term "pharmaceutical composition" refers to the combination of an active agent with a carrier, inert or active, making the composition especially suitable for diagnostic or therapeutic use in vivo, in vivo or ex vivo.

As used herein, the term "pharmaceutically acceptable carrier" refers to any of the standard pharmaceutical carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the terms "solid phase supports" or "solid supports," are used in their broadest sense to refer to a number of supports that are available and known to those of ordinary skill in the art. Solid phase supports include, but are not limited to, silica gels, resins, derivatized plastic films, glass beads, cotton, plastic beads, alumina gels, and the like. As used herein, "solid supports" also include synthetic antigen-presenting matrices, cells, liposomes, and the like. A suitable solid phase support may be selected on the basis of desired end use and suitability for various protocols. For example, for peptide synthesis, solid phase supports may refer to resins such as polystyrene (e.g., PAM-resin obtained from Bachem, Inc., Peninsula Laboratories, etc.), POLYHIPE) resin (obtained from Aminotech, Canada), polyamide resin (obtained from Peninsula Laboratories), polystyrene resin grafted with polyethylene glycol (TENTAGEL, Rapp Polymere, Tubingen, Germany) or polydimethylacrylamide resin (obtained from Milligen/Biosearch, California).

As used herein, the term "pathogen" refers a biological agent that causes a disease state (e.g., infection, cancer, etc.) in a host. "Pathogens" include, but are not limited to, viruses, bacteria, archaea, fungi, protozoans, mycoplasma, prions, and parasitic organisms.

The terms "bacteria" and "bacterium" refer to all prokaryotic organisms, including those within all of the phyla in the Kingdom Procaryotae. It is intended that the term encompass all microorganisms considered to be bacteria including *Mycoplasma, Chlamydia, Actinomyces, Streptomyces*, and *Rickettsia*. All forms of bacteria are included within this definition including cocci, bacilli, spirochetes, spheroplasts, protoplasts, etc. Also included within this term are prokaryotic organisms which are gram negative or gram positive. "Gram negative" and "gram positive" refer to staining patterns with the Gram-staining process which is well known in the art. (See e.g., Finegold and Martin, Diagnostic Microbiology, 6th Ed., CV Mosby St. Louis, pp. 13-15 [1982]). "Gram positive bacteria" are bacteria which retain the primary dye used in the Gram stain, causing the stained cells to appear dark blue to purple under the microscope. "Gram negative bacteria" do not retain the primary dye used in the Gram stain, but are stained by the counterstain. Thus, gram negative bacteria appear red.

As used herein, the term "microorganism" refers to any species or type of microorganism, including but not limited to, bacteria, archaea, fungi, protozoans, mycoplasma, and parasitic organisms. The present invention contemplates that a number of microorganisms encompassed therein will also be pathogenic to a subject.

As used herein, the term "fungi" is used in reference to eukaryotic organisms such as the molds and yeasts, including dimorphic fungi.

As used herein, the term "virus" refers to minute infectious agents, which with certain exceptions, are not observable by light microscopy, lack independent metabolism, and are able to replicate only within a living host cell. The individual particles (i.e., virions) typically consist of nucleic acid and a protein shell or coat; some virions also have a lipid containing membrane. The term "virus" encompasses all types of viruses, including animal, plant, phage, and other viruses.

The term "sample" as used herein is used in its broadest sense. A sample suspected of indicating a condition characterized by the dysregulation of apoptotic function may comprise a cell, tissue, or fluids, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the terms "purified" or "to purify" refer, to the removal of undesired components from a sample. As used herein, the term "substantially purified" refers to molecules that are at least 60% free, preferably 75% free, and most preferably 90%, or more, free from other components with which they usually associated.

As used herein, the term "antigen binding protein" refers to proteins which bind to a specific antigen. "Antigen binding proteins" include, but are not limited to, immunoglobulins, including polyclonal, monoclonal, chimeric, single chain, and humanized antibodies, Fab fragments, F(ab')2 fragments, and Fab expression libraries. Various procedures known in the art are used for the production of polyclonal antibodies. For the production of antibody, various host animals can be immunized by injection with the peptide corresponding to the desired epitope including but not limited to rabbits, mice, rats, sheep, goats, etc. In a preferred embodiment, the peptide is conjugated to an immunogenic carrier (e.g., diphtheria toxoid, bovine serum albumin (BSA), or keyhole limpet hemocyanin [KLH]). Various adjuvants are used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (Bacille Calmette-Guerin) and *Corynebacterium parvum*.

For preparation of monoclonal antibodies, any technique that provides for the production of antibody molecules by continuous cell lines in culture may be used (See e.g., Harlow and Lane, Antibodies: A Laboratory Manual, Cold Spring Harbor Laboratory Press, Cold Spring Harbor, N.Y.). These include, but are not limited to, the hybridoma technique originally developed by Köhler and Milstein (Köhler and Milstein, Nature, 256:495-497 [1975]), as well as the trioma technique, the human B-cell hybridoma technique (See e.g., Kozbor et al., Immunol. Today, 4:72 [1983]), and the EBV-hybridoma technique to produce human monoclonal antibodies (Cole et al., in Monoclonal Antibodies and Cancer Therapy, Alan R. Liss, Inc., pp. 77-96 [1985]).

According to the invention, techniques described for the production of single chain antibodies (U.S. Pat. No. 4,946, 778; herein incorporated by reference) can be adapted to produce specific single chain antibodies as desired. An additional embodiment of the invention utilizes the techniques known in the art for the construction of Fab expression libraries (Huse et al., Science, 246:1275-1281 [1989]) to allow rapid and easy identification of monoclonal Fab fragments with the desired specificity.

Antibody fragments that contain the idiotype (antigen binding region) of the antibody molecule can be generated by known techniques. For example, such fragments include but are not limited to: the F(ab')2 fragment that can be produced by pepsin digestion of an antibody molecule; the Fab' fragments that can be generated by reducing the disulfide bridges of an F(ab')2 fragment, and the Fab fragments that can be generated by treating an antibody molecule with papain and a reducing agent.

Genes encoding antigen binding proteins can be isolated by methods known in the art. In the production of antibodies, screening for the desired antibody can be accomplished by techniques known in the art (e.g., radioimmunoassay, ELISA (enzyme-linked immunosorbant assay), "sandwich" immunoradiometric assays, gel diffusion precipitin reactions, immunodiffusion assays, in situ immunoassays (using colloidal gold, enzyme or radioisotope labels, for example), Western Blots, precipitation reactions, agglutination assays (e.g., gel agglutination assays, hemagglutination assays, etc.), complement fixation assays, immunofluorescence assays, protein A assays, and immunoelectrophoresis assays, etc.) etc.

As used herein, the term "immunoglobulin" or "antibody" refer to proteins that bind a specific antigen. Immunoglobulins include, but are not limited to, polyclonal, monoclonal, chimeric, and humanized antibodies, Fab fragments, F(ab')$_2$ fragments, and includes immunoglobulins of the following classes: IgG, IgA, IgM, IgD, IbE, and secreted immunoglobulins (sIg). Immunoglobulins generally comprise two identical heavy chains and two light chains. However, the terms "antibody" and "immunoglobulin" also encompass single chain antibodies and two chain antibodies.

The term "epitope" as used herein refers to that portion of an antigen that makes contact with a particular immunoglobulin. When a protein or fragment of a protein is used to immunize a host animal, numerous regions of the protein may induce the production of antibodies which bind specifically to a given region or three-dimensional structure on the protein; these regions or structures are referred to as "antigenic determinants". An antigenic determinant may compete with the intact antigen (i.e., the "immunogen" used to elicit the immune response) for binding to an antibody.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "modulate" refers to the activity of a compound (e.g., a compound of the present invention) to affect (e.g., to promote or retard) an aspect of cellular function, including, but not limited to, cell growth, proliferation, apoptosis, and the like.

As used herein, the term "competes for binding" is used in reference to a first molecule (e.g., a first compound of the present invention) with an activity that binds to the same substrate (e.g., the oligomycin sensitivity conferring protein in mitochondrial ATP synthase) as does a second molecule (e.g., a second compound of the present invention or other molecule that binds to the oligomycin sensitivity conferring protein in mitochondrial ATP synthase, etc.). The efficiency (e.g., kinetics or thermodynamics) of binding by the first molecule may be the same as, or greater than, or less than, the efficiency of the substrate binding to the second molecule. For example, the equilibrium binding constant ($K_D$) for binding to the substrate may be different for the two molecules.

As used herein, the term "instructions for administering said compound to a subject," and grammatical equivalents thereof, includes instructions for using the compositions contained in a kit for the treatment of conditions characterized by the dysregulation of apoptotic processes in a cell or tissue (e.g., providing dosing, route of administration, decision trees for treating physicians for correlating patient-specific characteristics with therapeutic courses of action). The term also specifically refers to instructions for using the compositions contained in the kit to treat autoimmune disorders (e.g., systemic lupus erythematosus, rheumatoid arthritis, graft-versus-host disease, myasthenia gravis, Sjögren's syndrome, etc.), chronic inflammatory conditions (e.g., psoriasis, asthma and Crohn's disease), hyperproliferative disorders (e.g., tumors, B cell lymphomas, T cell lymphomas, etc.), viral infections (e.g., herpes virus, papilloma virus, HIV), and other conditions such as osteoarthritis and atherosclerosis, and the like.

The term "test compound" refers to any chemical entity, pharmaceutical, drug, and the like, that can be used to treat or prevent a disease, illness, sickness, or disorder of bodily function, or otherwise alter the physiological or cellular status of a sample (e.g., the level of dysregulation of apoptosis in a cell or tissue). Test compounds comprise both known and potential therapeutic compounds. A test compound can be determined to be therapeutic by using the screening methods of the present invention. A "known therapeutic compound" refers to a therapeutic compound that has been shown (e.g., through animal trials or prior experience with administration to humans) to be effective in such treatment or prevention. In preferred embodiments, "test compounds" are agents that modulate apoptosis in cells.

As used herein, the term "third party" refers to any entity engaged in selling, warehousing, distributing, or offering for sale a test compound contemplated for administered with a compound for treating conditions characterized by the dysregulation of apoptotic processes.

GENERAL DESCRIPTION OF THE INVENTION

As a class of drugs, benzodiazepine compounds have been widely studied and reported to be effective medicaments for treating a number of disease. For example, U.S. Pat. Nos. 4,076,823, 4,110,337, 4,495,101, 4,751,223 and 5,776,946, each incorporated herein by reference in its entirety, report that certain benzodiazepine compounds are effective as analgesic and anti-inflammatory agents. Similarly, U.S. Pat. No. 5,324,726 and U.S. Pat. No. 5,597,915, each incorporated by reference in its entirety, report that certain benzodiazepine compounds are antagonists of cholecystokinin and gastrin and thus might be useful to treat certain gastrointestinal disorders.

Other benzodiazepine compounds have been studied as inhibitors of human neutrophil elastase in the treating of human neutrophil elastase-mediated conditions such as myocardial ischemia, septic shock syndrome, among others (See e.g., U.S. Pat. No. 5,861,380 incorporated herein by reference in its entirety). U.S. Pat. No. 5,041,438, incorporated herein by reference in its entirety, reports that certain benzodiazepine compounds are useful as anti-retroviral agents.

Despite the attention benzodiazepine compounds have drawn, it will become apparent from the description below, that the present invention provides novel benzodiazepine compounds and related compounds and methods of using the novel compounds, as well as known compounds, for treating a variety of diseases.

Benzodiazepine compounds are known to bind to benzodiazepine receptors in the central nervous system (CNS) and thus have been used to treat various CNS disorders including anxiety and epilepsy. Peripheral benzodiazepine receptors have also been identified, which receptors may incidentally also be present in the CNS. The present invention demonstrates that benzodiazepines and related compounds have pro-apoptotic and cytotoxic properties useful in the treatment of transformed cells grown in tissue culture. The route of action of these compounds is not through the previously identified benzodiazepine receptors.

Experiments conducted during the development of the present invention have identified novel biological targets for benzodiazepine compounds and related compounds (some of which are related by their ability to bind cellular target molecules rather than their homology to the overall chemical structure of benzodiazepine compounds). In particular, the present invention provides compounds that interact, directly or indirectly, with particular mitochondrial proteins to elicit the desired biological effects.

Thus, in some embodiments, the present invention provides a number of novel compounds and previously known compounds directed against novel cellular targets to achieve desired biological results. In other embodiments, the present invention provides methods for using such compounds to regulate biological processes. The present invention also provides drug-screening methods to identify and optimize compounds. The present invention further provides diagnostic markers for identifying diseases and conditions, for monitoring treatment regimens, and/or for identifying optimal therapeutic courses of action. These and other research and therapeutic utilities are described below.

Similar benzodiazepine related compounds, described in U.S. patent application Ser. Nos. 10/886,450, 10/795,535, 10/634,114, 10/427, 212, 10/427,211, 10/217,878, 09/767, 283, and 09/700,101, and U.S. Provisional Patent Application Nos. 60/607,599 and 60/565,788, each herein incorporated by reference in their entireties, are also characterized as modulators of cell death. Gene expression profiles of such benzodiazepine related compounds demonstrate a modulation of genes directed toward apoptosis. Such benzodiazepine related compounds further find use within pharmaceutical compositions along with apoptotic agents. Additionally, such benzodiazepine related compounds find use in therapeutic applications (e.g., treating hyperproliferative disorders).

DETAILED DESCRIPTION OF THE INVENTION

The present invention provides novel chemical compounds, methods for their discovery, and their therapeutic use. In particular, the present invention provides benzodiazepine derivatives and related compounds and methods of using benzodiazepine derivatives and related compounds as therapeutic agents to treat a number of conditions associated with the faulty regulation of the processes of programmed cell death, autoimmunity, inflammation, and hyperproliferation, and the like.

Exemplary compositions and methods of the present invention are described in more detail in the following sections: I. Modulators of Cell Death; II. Modulators of Cell Growth and Proliferation; III. Exemplary Compounds; IV. Pharmaceutical compositions, formulations, and exemplary administration routes and dosing considerations; V. Drug screens; VI. Therapeutic Applications; and VII. ATPase Inhibitors And Methods For Identifying Therapeutic Inhibitors.

The practice of the present invention employs, unless otherwise indicated, conventional techniques of organic chemistry, pharmacology, molecular biology (including recombinant techniques), cell biology, biochemistry, and immunology, which are within the skill of the art. Such techniques are explained fully in the literature, such as, "Molecular cloning: a laboratory manual" Second Edition (Sambrook et al., 1989); "Oligonucleotide synthesis" (M. J. Gait, ed., 1984); "Animal cell culture" (R. I. Freshney, ed., 1987); the series "Methods in enzymology" (Academic Press, Inc.); "Handbook of experimental immunology" (D. M. Weir & C. C. Blackwell, eds.); "Gene transfer vectors for mammalian cells" (J. M. Miller & M. P. Calos, eds., 1987); "Current protocols in molecular biology" (F. M. Ausubel et al., eds., 1987, and periodic updates); "PCR: the polymerase chain reaction" (Mullis et al., eds., 1994); and "Current protocols in immunology" (J. E. Coligan et al., eds., 1991), each of which is herein incorporated by reference in its entirety.

I. Modulators of Cell Death

In preferred embodiments, it is contemplated that the present invention regulates apoptosis through the exposure of cells to compounds. The effect of compounds can be measured by detecting any number of cellular changes. Cell death may be assayed as described herein and in the art. In preferred embodiments, cell lines are maintained under appropriate cell culturing conditions (e.g., gas ($CO_2$), temperature and media) for an appropriate period of time to attain exponential proliferation without density dependent constraints. Cell number and or viability are measured using standard techniques, such as trypan blue exclusion/hemo-cytometry, or MTT dye conversion assay. Alternatively, the cell may be analyzed for the expression of genes or gene products associated with aberrations in apoptosis or necrosis.

In preferred embodiments, it is contemplated that exposing the present invention to a cell induces apoptosis. In some embodiments, it is contemplated that the present invention causes an initial increase in cellular ROS levels (e.g., $O_2^-$). In further embodiments, it is contemplated that exposure of the compounds of the present invention to a cell causes an increase in cellular $O_2^-$ levels. In still further embodiments, it is contemplated that the increase in cellular $O_2^-$ levels resulting from the compounds of the present invention is detectable with a redox-sensitive agent that reacts specifically with $O_2^-$ (e.g., dihyroethedium (DHE)).

In other embodiments, it is contemplated that increased cellular $O_2^-$ levels resulting from compounds of the present invention diminish after a period of time (e.g., 10 minutes). In other embodiments, it is contemplated that increased cellular $O_2^-$ levels resulting from the compounds of the present invention diminish after a period of time and increase again at a later time (e.g., 10 hours). In further embodiments, it is contemplated that increased cellular $O_2^-$ levels resulting from the compounds of the present invention diminish at 1 hour and increase again after 4 hours. In preferred embodiments, it is contemplated that an early increase in cellular $O_2^-$ levels, followed by a diminishing in cellular $O_2^-$ levels, followed by another increase in cellular $O_2^-$ levels resulting from the compounds of the present invention is due to different cellular processes (e.g., bimodal cellular mechanisms).

In some embodiments, it is contemplated that the present invention causes a collapse of a cell's mitochondrial $\Delta\Psi_m$. In preferred embodiments, it is contemplated that a collapse of a cell's mitochondrial $\Delta\Psi_m$ resulting from the present invention is detectable with a mitochondria-selective potentiometric probe (e.g., $DiOC_6$). In further embodiments, it is contemplated that a collapse of a cell's mitochondrial $\Delta\Psi_m$ resulting from the present invention occurs after an initial increase in cellular $O_2^-$ levels.

In some embodiments, it is contemplated that the present invention enables caspace activation. In other embodiments, it is contemplated that the present invention causes the release of cytochrome c from mitochondria. In further embodiments, it is contemplated that the present invention alters cystolic cytochrome c levels. In still other embodiments, it is contemplated that altered cystolic cytochrome c levels resulting from the present invention are detectable with immunoblotting cytosolic fractions. In preferred embodiments, it is contemplated that diminished cystolic cytochrome c levels resulting from the present invention are detectable after a period of time (e.g., 10 hours). In further preferred embodiments, it is contemplated that diminished cystolic cytochrome c levels resulting from the present invention are detectable after 5 hours.

In other embodiments, it is contemplated that the present invention causes the opening of the mitochondrial PT pore. In preferred embodiments, it is contemplated that the cellular release of cytochrome c resulting from the present invention is consistent with a collapse of mitochondrial $\Delta\Psi_m$. In still further preferred embodiments, it is contemplated that the present invention causes an increase in cellular $O_2^-$ levels after a mitochondrial $\Delta\Psi_m$ collapse and a release of cytochrome c. In further preferred embodiments, it is contemplated that a rise in cellular $O_2^-$ levels is caused by a mitochondrial $\Delta\Psi_m$ collapse and release of cytochrome c resulting from the present invention.

In other embodiments, it is contemplated that the present invention causes cellular caspase activation. In preferred embodiments, it is contemplated that caspase activation resulting from the present invention is measurable with a pan-caspase sensitive fluorescent substrate (e.g., FAM-VAD-fmk). In still further embodiments, it is contemplated that caspase activation resulting from the present invention tracks with a collapse of mitochondrial $\Delta\Psi_m$. In other embodiments, it is contemplated that the present invention causes an appearance of hypodiploid DNA. In preferred embodiments, it is contemplated that an appearance of hypodiploid DNA resulting from the present invention is slightly delayed with respect to caspase activation.

In some embodiments, it is contemplated that the molecular target for the present invention is found within mitochondria. In further embodiments, it is contemplated that the molecular target of the present invention involves the mitochondrial ATPase. The primary sources of cellular ROS include redox enzymes and the mitochondrial respiratory chain (hereinafter MRC). In preferred embodiments, it is contemplated that cytochrome c oxidase (complex IV of the MRC) inhibitors (e.g., $NaN_3$) preclude a present invention dependent increase in cellular ROS levels. In other preferred embodiments, it is contemplated that the ubiquinol-cytochrome c reductase component of MRC complex III inhibitors (e.g., FK506) preclude a present invention dependent increase in ROS levels.

In some embodiments, it is contemplated that an increase in cellular ROS levels result from the binding of the compounds of the present invention to a target within mitochondria. In preferred embodiments, it is contemplated that the compounds of the present invention oxidize 2',7'-dichlorodihydrofluorescin (hereinafter DCF) diacetate to DCF. DCF is a redox-active species capable of generating ROS. In further embodiments, it is contemplated that the rate of DCF production resulting from the present invention increases after a lag period.

Antimycin A generates $O_2^-$ by inhibiting ubiquinol-cytochrome c reductase. In preferred embodiments, it is contemplated that the present invention increases the rate of ROS production in an equivalent manner to antimycin A. In further embodiments, it is contemplated that the present invention increases the rate of ROS production in an equivalent manner to antimycin A under aerobic conditions supporting state 3 respiration. In further embodiments, it is contemplated that the compounds of the present invention do not directly target the MPT pore. In additional embodiments, it is contemplated that the compounds of the present invention do not generate substantial ROS in the subcellular S15 fraction (e.g., cytosol; microsomes). In even further embodiments, it is contemplated that the compounds of the present invention do not stimulate ROS if mitochondria are in state 4 respiration.

MRC complexes I-III are the primary sources of ROS within mitochondria. In preferred embodiments, it is contemplated that the primary source of an increase in cellular ROS levels resulting from the dependent invention emanates from these complexes as a result of inhibiting the mitochondrial $F_1F_0$-ATPase. Indeed, in still further embodiments, it is contemplated that the present invention inhibits mitochondrial ATPase activity of bovine sub-mitochondrial particles (hereinafter SMPs). In particularly preferred embodiments, it is contemplated that the compounds of the present invention bind to the OSCP component of the mitochondrial $F_1F_0$-ATPase.

Oligomycin is a macrolide natural product that binds to the mitochondrial $F_1F_0$-ATPase, induces a state 3 to 4 transition, and as a result, generates ROS (e.g., $O_2^-$). In preferred embodiments, it is contemplated that the present invention binds the OSCP component of the mitochondrial $F_1F_0$-ATPase. In certain embodiments, it is contemplated that screening assays of the present invention permit detection of binding partners of the OSCP. OSCP is an intrinsically fluorescent protein. In certain embodiments, it is contemplated that titrating a solution of test compounds of the present invention into an *E. coli* sample overexpressed with OSCP results in quenching of the intrinsic OSCP fluorescence. In other embodiments, fluorescent or radioactive test compounds can be used in direct binding assays. In other embodiments, competition binding experiments can be conducted. In this type of assay, test compounds are assessed for their ability to compete with a compound of the present invention for binding to the OSCP. In some embodiments, it is contemplated that the compounds of the present invention cause a reduced increase in cellular ROS levels and reduce apoptosis in cells through regulation of the OSCP gene (e.g., altering expression of the OSCP gene). In further embodiments, it is contemplated that the present invention functions by altering the molecular motions of the ATPase motor.

II. Modulators of Cellular Proliferation and Cell Growth

In some embodiments, it is contemplated that the compounds and methods of the present invention cause decreased cellular proliferation. In other embodiments, it is contemplated that the compounds and methods of the present invention cause decreased cellular proliferation and apoptosis.

III. Exemplary Compounds

Exemplary compounds of the present invention are provided below. The present invention is not limited to any particular compound.

In certain embodiments, the present invention provides a composition comprising the following formula:

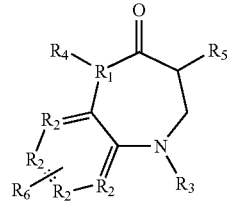

including both R and S enantiomeric forms and racemic mixtures.

In such preferred embodiments, R1 is a nitrogen atom or a carbon atom; R2 is carbon or nitrogen; R3 comprises a chemical moiety comprising a heterocyclic group containing 3 or more carbon atoms; R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and R6 is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In preferred embodiments, R3 is selected from the group consisting of:

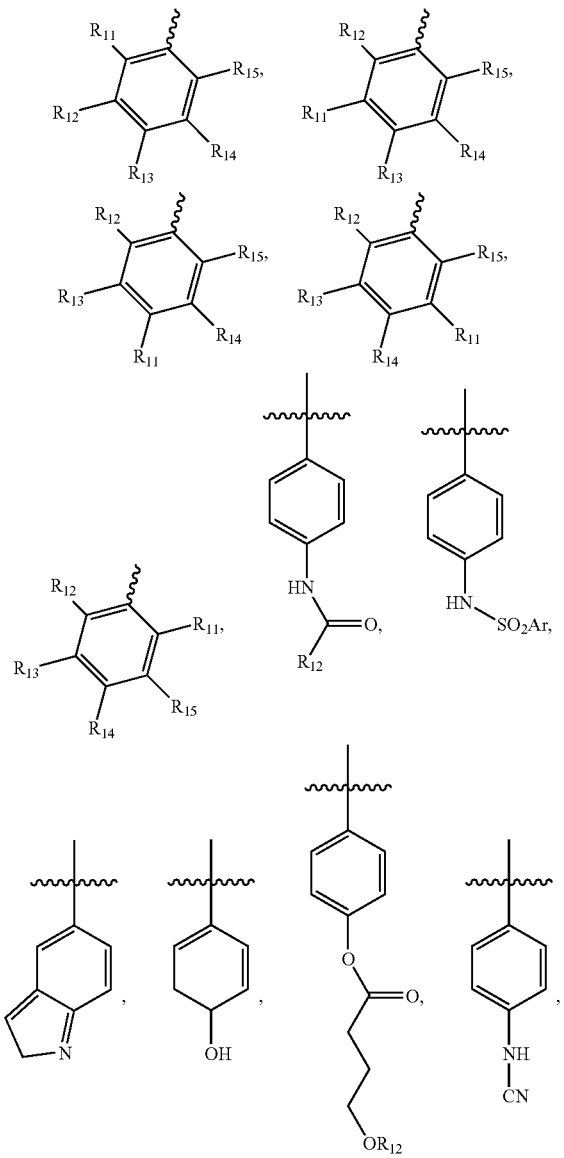

-continued

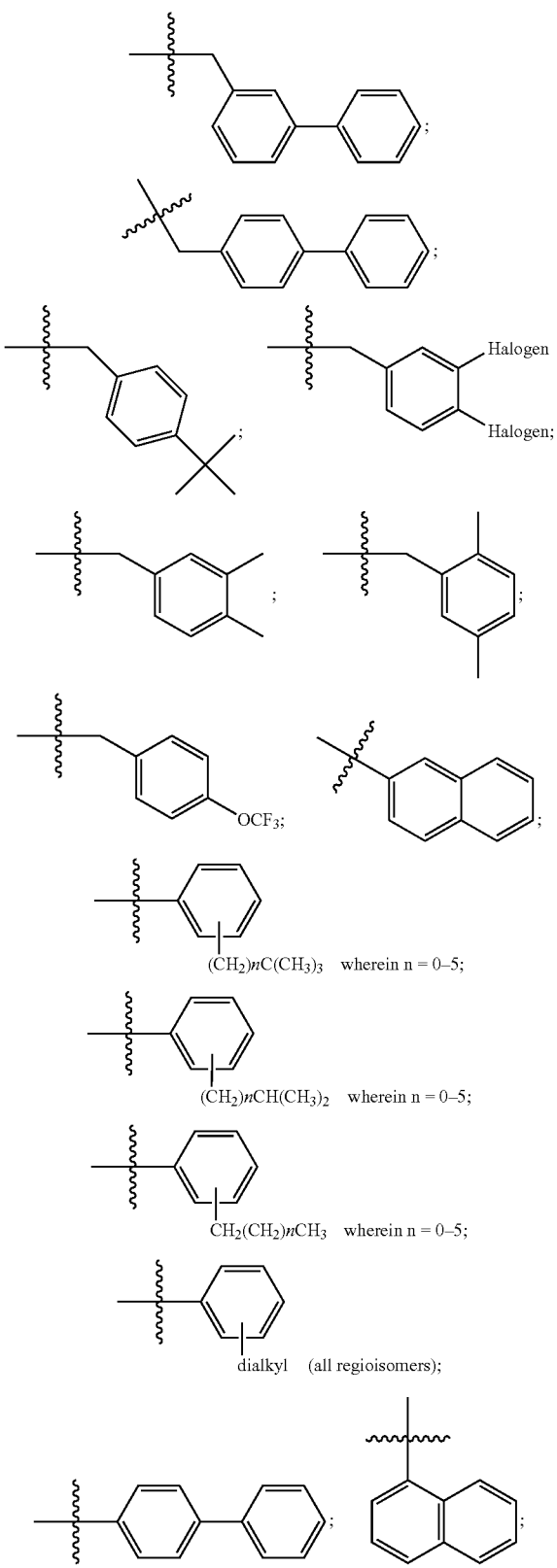

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In preferred embodiments, R4 or R5 are selected from group consisting of: napthalalanine; phenol; 1-Nathalenol; 2-Napthalenol;

-continued

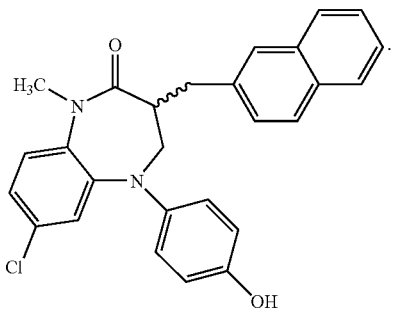

In other preferred embodiments, R4 or R5 is selected from the group consisting of:

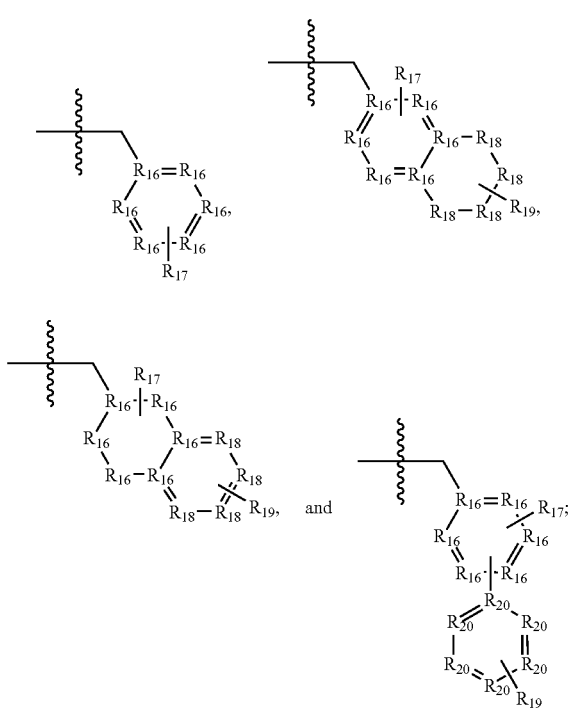

wherein R16 is carbon or nitrogen; wherein R17 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In yet other preferred embodiments, the composition is:

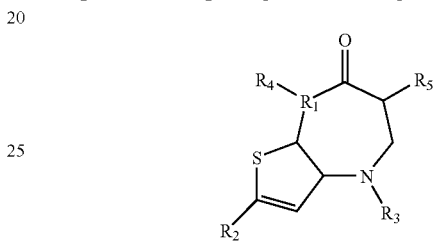

In certain embodiments, the present invention provides a composition comprising the following formula:

including both R and S enantiomeric forms and racemic mixtures.

In such preferred embodiments, R1 is a nitrogen atom or a carbon atom; R2 is selected from H, a hydroxy, an alkoxy, a halo, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; R3 comprises a chemical moiety comprising a heterocyclic group containing 3 or more carbon atoms; and R4 and R5 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety.

In preferred embodiments, R3 is selected from the group consisting of:

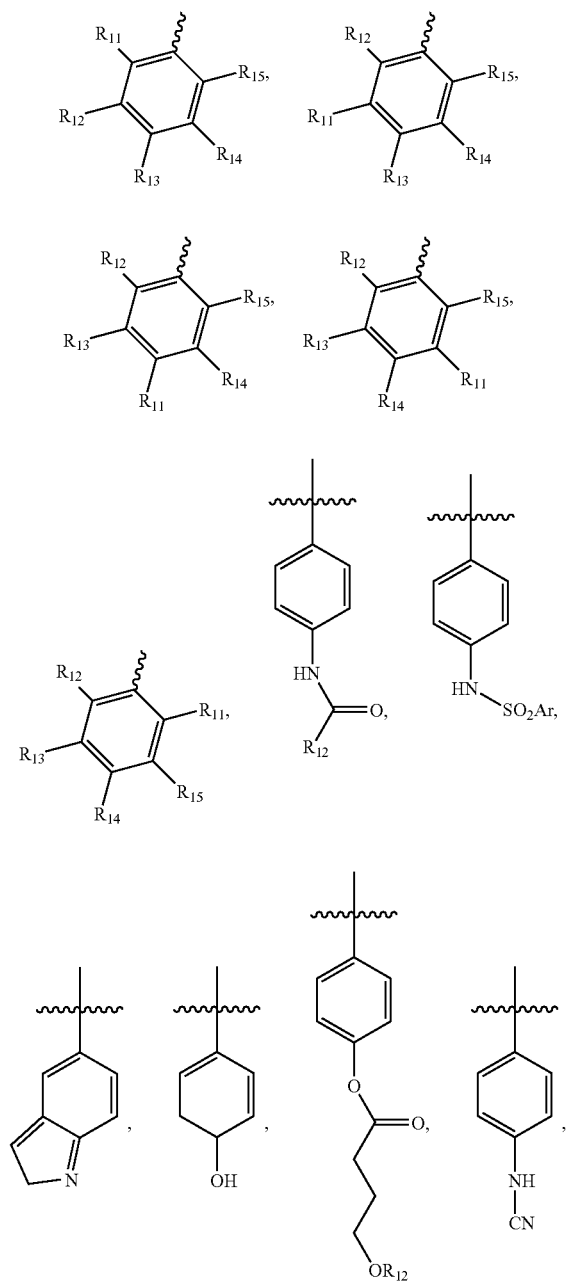

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In preferred embodiments, R4 or R5 are selected from group consisting of:

napthalalanine; phenol; 1-Napthalenol; 2-Napthalenol;

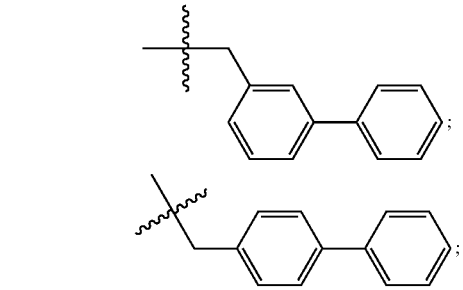

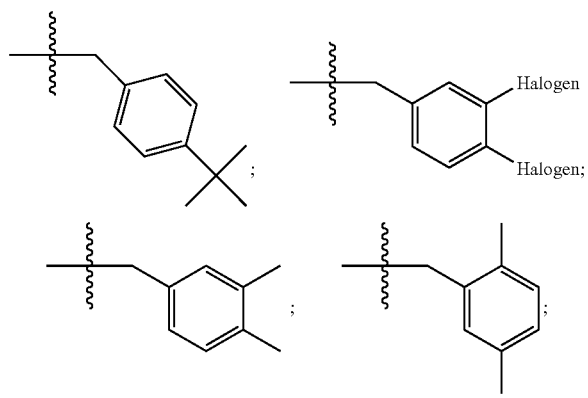

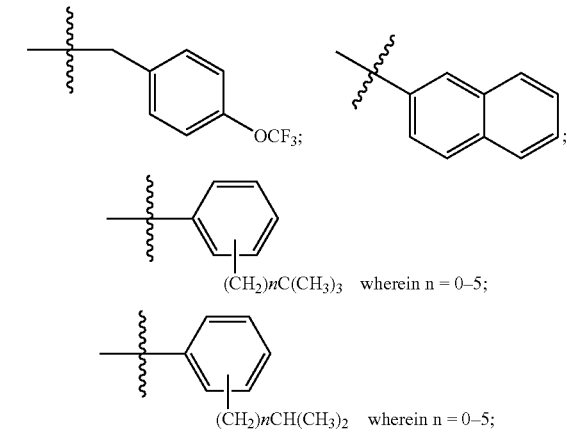

(CH$_2$)$n$C(CH$_3$)$_3$ wherein n = 0–5;

(CH$_2$)$n$CH(CH$_3$)$_2$ wherein n = 0–5;

CH$_2$(CH$_2$)$n$CH$_3$ wherein n = 0–5;

dialkyl (all regioisomers);

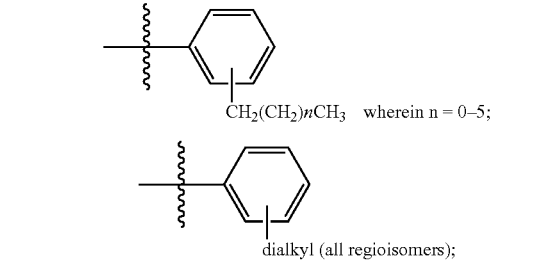

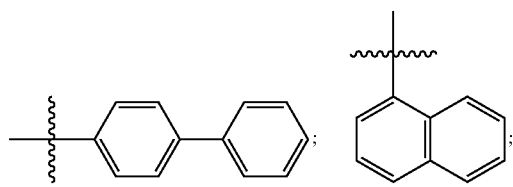

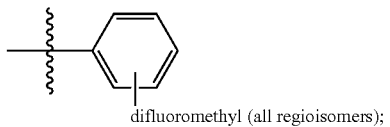

difluoromethyl (all regioisomers);

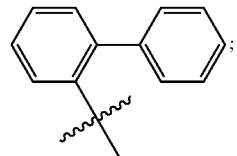

quinolines, and all aromatic regioisomers.

In other preferred embodiments, R4 or R5 is selected from the group consisting of:

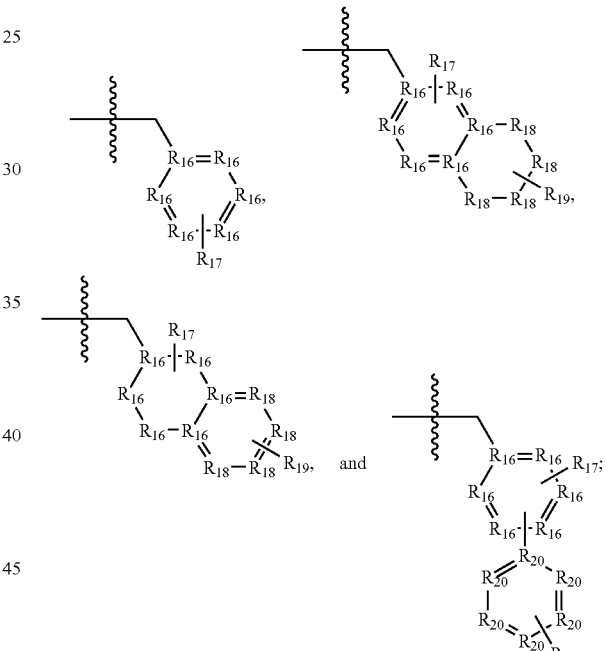

wherein R16 is carbon or nitrogen; wherein R17 is selected from the group consisting of hydrogen; halogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; halogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In certain embodiments, the present invention provides a composition comprising the following formula:

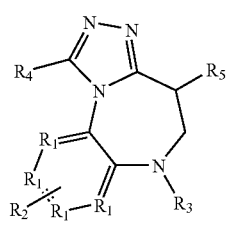

including both R and S enantiomeric forms and racemic mixtures.

In such preferred embodiments, R1 is carbon or nitrogen; R2 is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; R3 comprises a chemical moiety comprising a heterocyclic group containing 3 or more carbon atoms; R4 is selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and R5 is selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety.

In preferred embodiments, R3 is selected from the group consisting of:

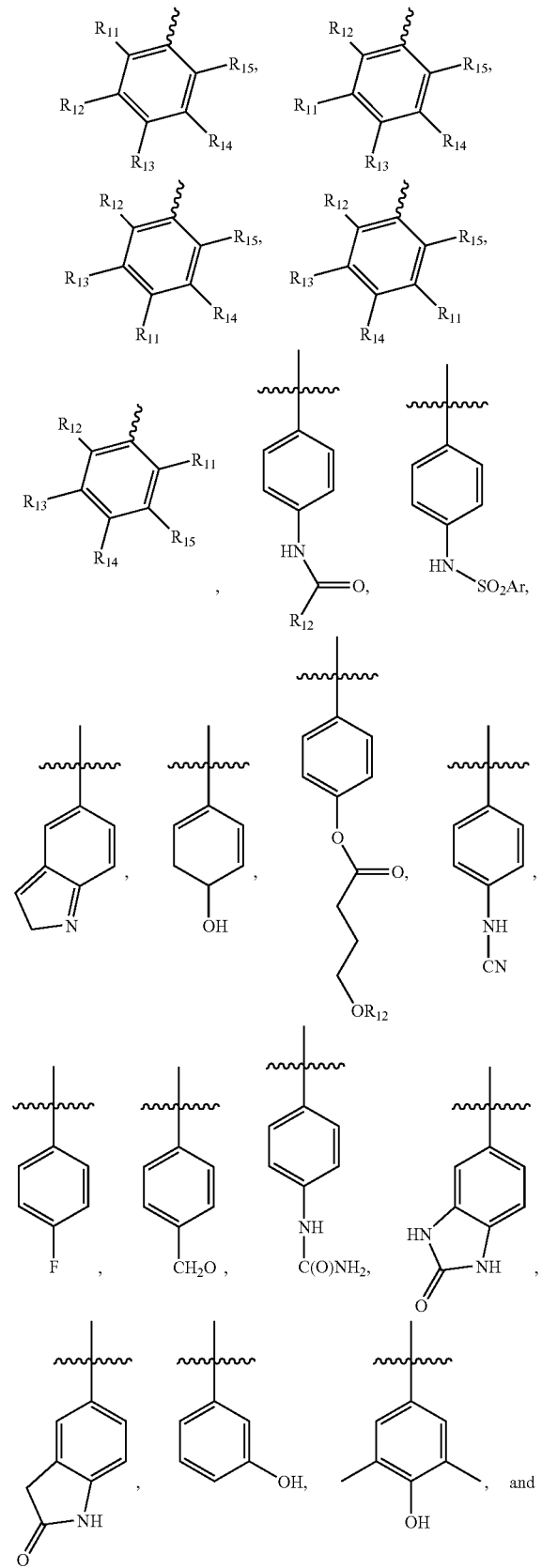

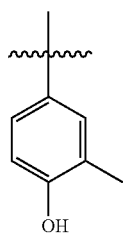

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In preferred embodiments, R4 or R5 are selected from group consisting of:

napthalalanine; phenol; 1-Napthalenol; 2-Napthalenol;

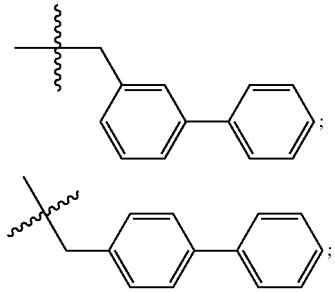

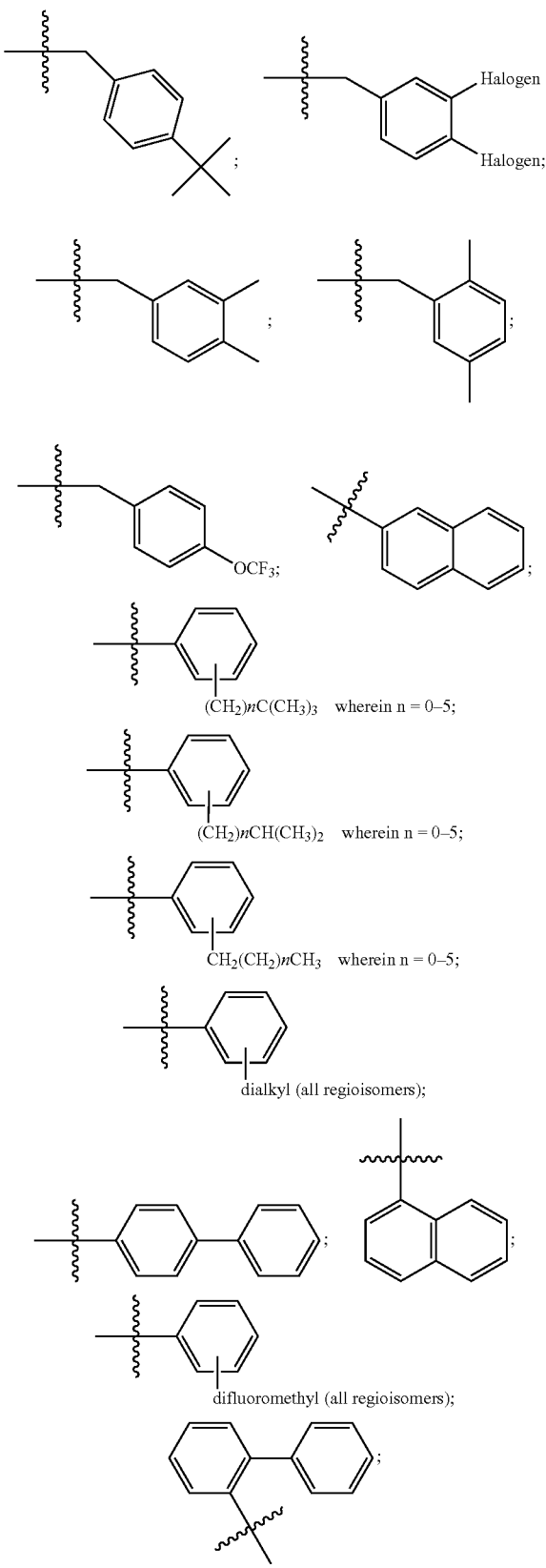

quinolines, and all aromatic regioisomers.

In other preferred embodiments, R4 or R5 is selected from the group consisting of:

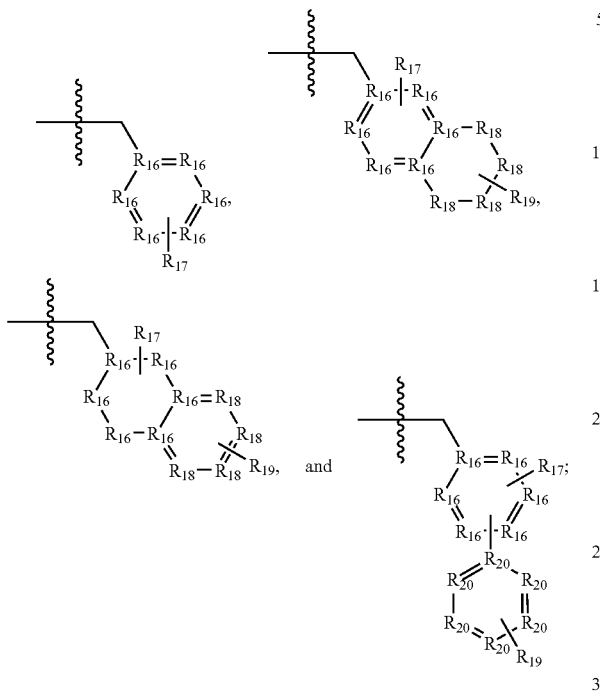

wherein R16 is carbon or nitrogen; wherein R17 is selected from the group consisting of hydrogen; halogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; halogen; CH$_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

From the above description, it is apparent that many specific examples are represented by the generic formulas presented above. A wide variety of sub combinations arising from selecting a particular group at each substituent position are possible and all such combinations are within the scope of this invention.

Further, it should be understood that the numerical ranges given throughout this disclosure should be construed as a flexible range that contemplates any possible subrange within that range. For example, the description of a group having the range of 1-10 carbons would also contemplate a group possessing a subrange of, for example, 1-3, 1-5, 1-8, or 2-3, 2-5, 2-8, 3-4, 3-5, 3-7, 3-9, 3-10, etc., carbons. Thus, the range 1-10 should be understood to represent the outer boundaries of the range within which many possible subranges are clearly contemplated. Additional examples contemplating ranges in other contexts can be found throughout this disclosure wherein such ranges include analogous subranges within.

Some specific examples of the compounds of the present invention include, but are not limited to:

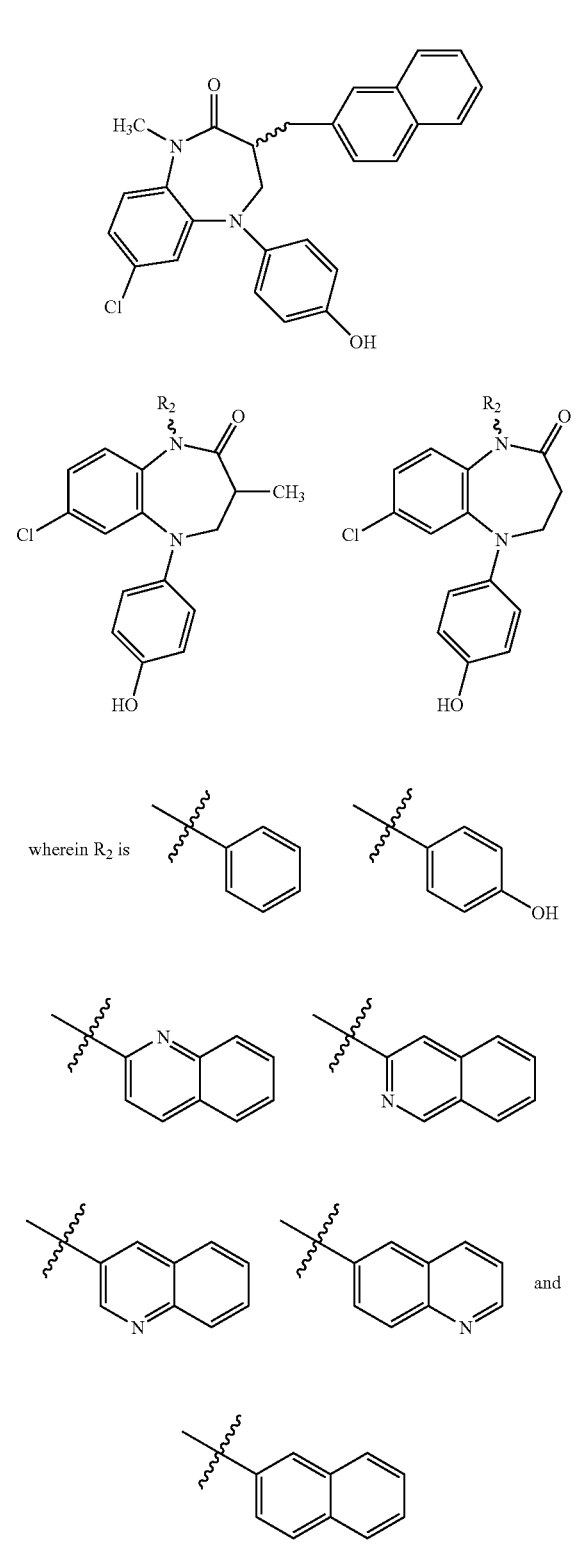

and dimethylphenyl (all isomers) and ditrifluoromethyl (all isomers).

The following compound (GD-423) is also contemplated:

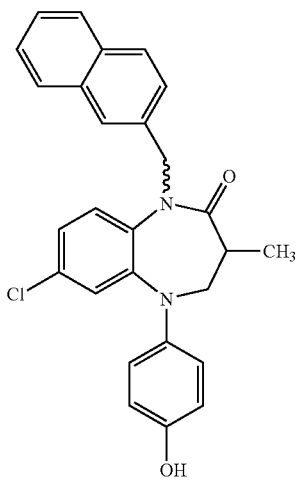

The following compounds are also contemplated:

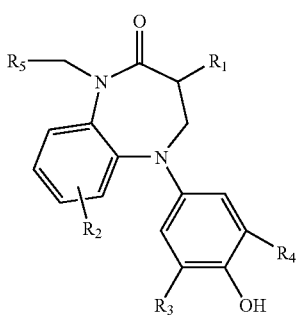

R1 = H, alkyl, or substituted alkyl
R3 = H, alkyl, or substituted alkyl
R4 = H, alkyl, or substituted alkyl stereochemistry is R, S, or racemic R2 is selected from hydrogen, a hydroxy, an alkoxy, a halo, an amino, a lower-alkyl-a-substituted-amino, an acetylamino, a hydroxyamino, an aliphatic group having 1–8 carbons and 1–20 hydrogens, a substituted aliphatic group of similar size, a cycloaliphatic group consisting of < 10 carbons, a substituted cycloaliphatic group, an aryl, and a heterocyclic

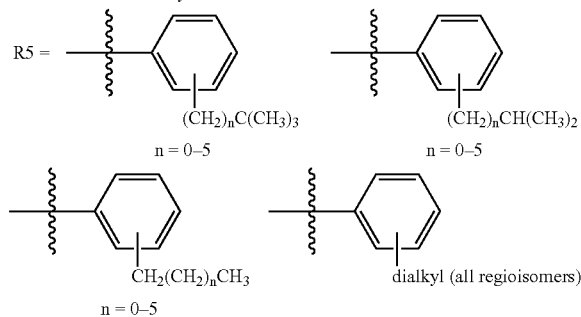

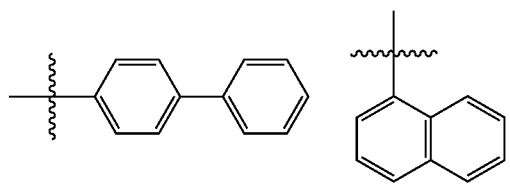

-continued

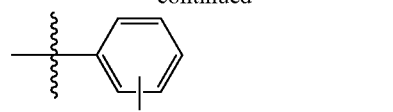

Difluoromethyl (all regioisomers)

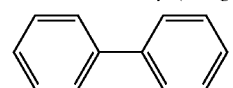

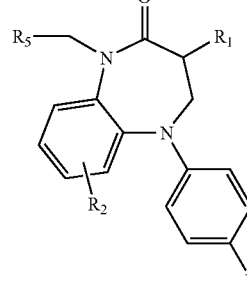

R1 = H, alkyl, or substituted alkyl
R3 = H, alkyl, or substituted alkyl
R4 = H, alkyl, or substituted alkyl stereochemistry is R, S, or racemic R2 is selected from hydrogen, hydroxy, an alkoxy, a halo, an amino, a lower-alkyl-a-substituted-amino, an acetylamino, a hydroxyamino, an aliphatic group having 1–8 carbons and 1–20 hydrogens, a substituted aliphatic group of similar size, a cycloaliphatic group consisting of < 10 carbons, a substituted cycloaliphatic group, an aryl, and a heterocyclic

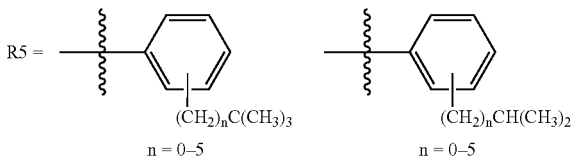

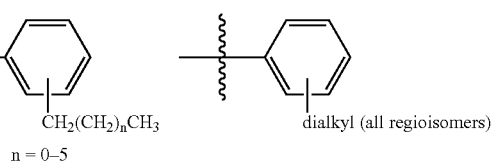

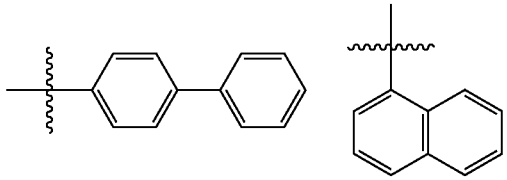

Difluoromethyl (all regioisomers)

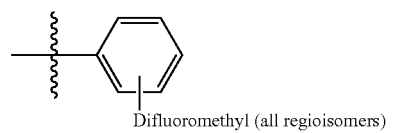

-continued

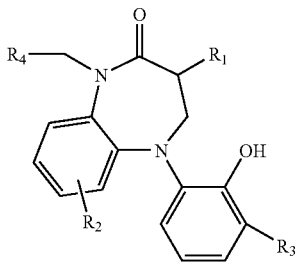

R1 = H, alkyl, or substituted alkyl
R3 = H, alkyl, or substituted alkyl stereochemistry is R, S, or racemic R2 is selected from hydrogen, hydroxy, an alkoxy, a halo, an amino, a lower-alkyl-a-substituted-amino, an acetylamino, a hydroxyamino, an aliphatic group having 1–8 carbons and 1–20 hydrogens, a substituted aliphatic group of similar size, a cycloaliphatic group consisting of < 10 carbons, a substituted cycloaliphatic group, an aryl, and a heterocyclic R4 = 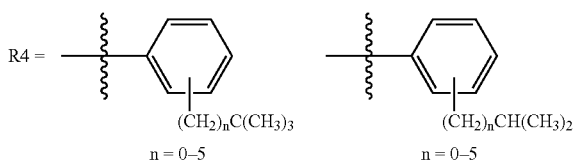

$(CH_2)_nC(CH_3)_3$    $(CH_2)_nCH(CH_3)_2$
n = 0–5            n = 0–5

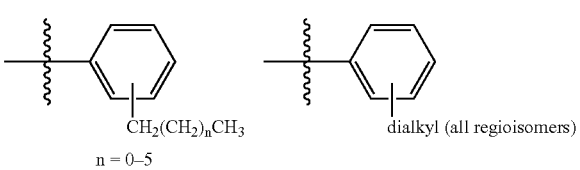

$CH_2(CH_2)_nCH_3$    dialkyl (all regioisomers)
n = 0–5

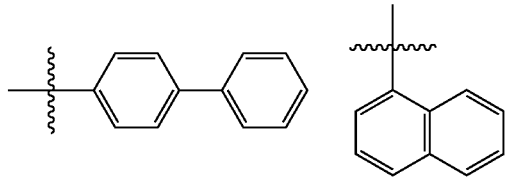

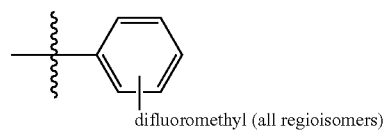

difluoromethyl (all regioisomers)

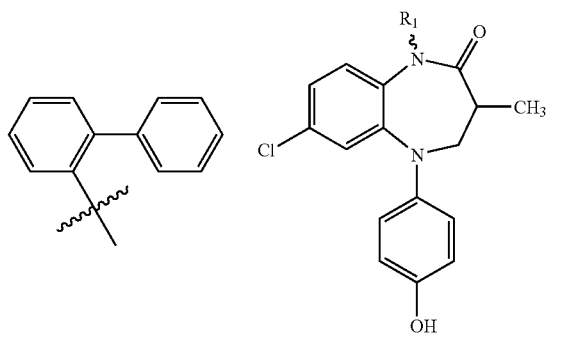

wherein R1 is selected from napthalalanine; phenol; 1-Napthalenol; 2-Napthalenol;

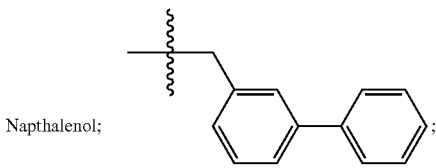

Napthalenol;

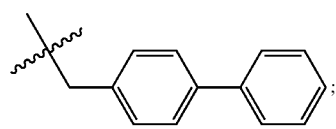

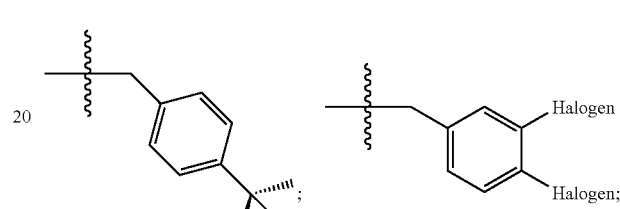

Halogen
Halogen;

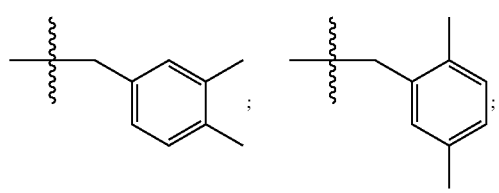

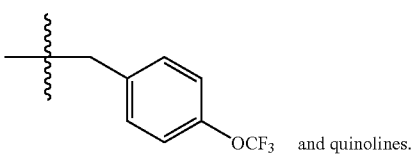

$OCF_3$ and quinolines.

A composition comprising the following formula:

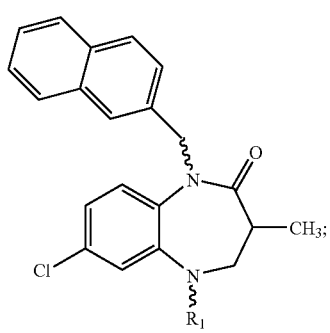

wherein $R_1$ is selected from:

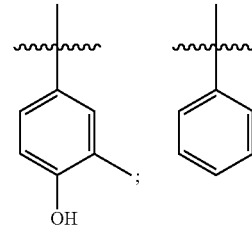

-continued

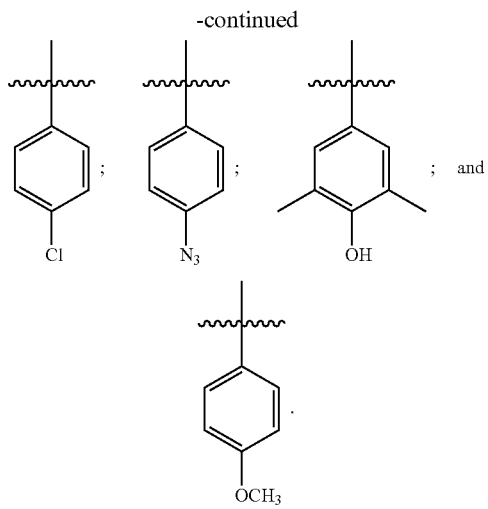

The stereochemistry of all derivatives embodied in the present invention is R, S, or racemic.

In further embodiments, the compounds of the present invention may be provided with 1,4-benzodiazepine related compounds as described in U.S. patent application Ser. Nos. 10/886,450, 10/795,535, 10/634,114, 10/427,211, 10/217,878, 09/767,283, and 09/700,101 and U.S. Provisional Patent Application Nos. 60/607,599 and 60/565,788; each herein incorporated by reference in their entireties. Additionally, the present invention provides the following compositions and compounds:

In preferred embodiments, the present invention provides a composition comprising the following formula:

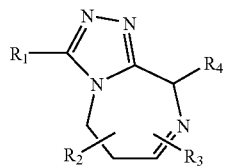

including both R and S enantiomeric forms and racemic mixtures; wherein R1 is selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R2 is comprises a chemical moiety comprising a heterocyclic group containing 3 or more carbon atoms; wherein R3 comprises a chemical moiety comprising a heterocyclic group containing 3 or more carbon atoms; and wherein R4 is selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety.

In preferred embodiments, the composition comprises the formula:

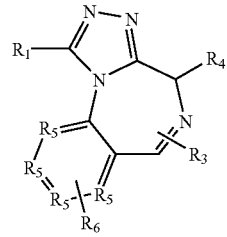

wherein R5 is carbon or nitrogen; and wherein R6 is selected from H, a hydroxy, an alkoxy, a halogen, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup.

In preferred embodiments, R3 is selected from the group consisting of:

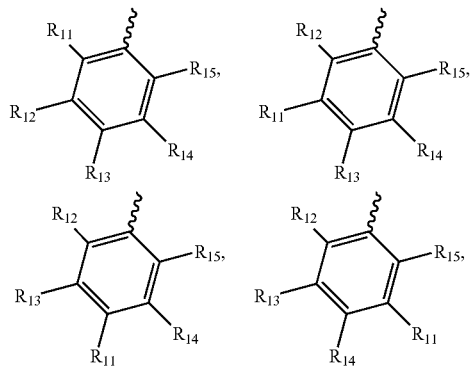

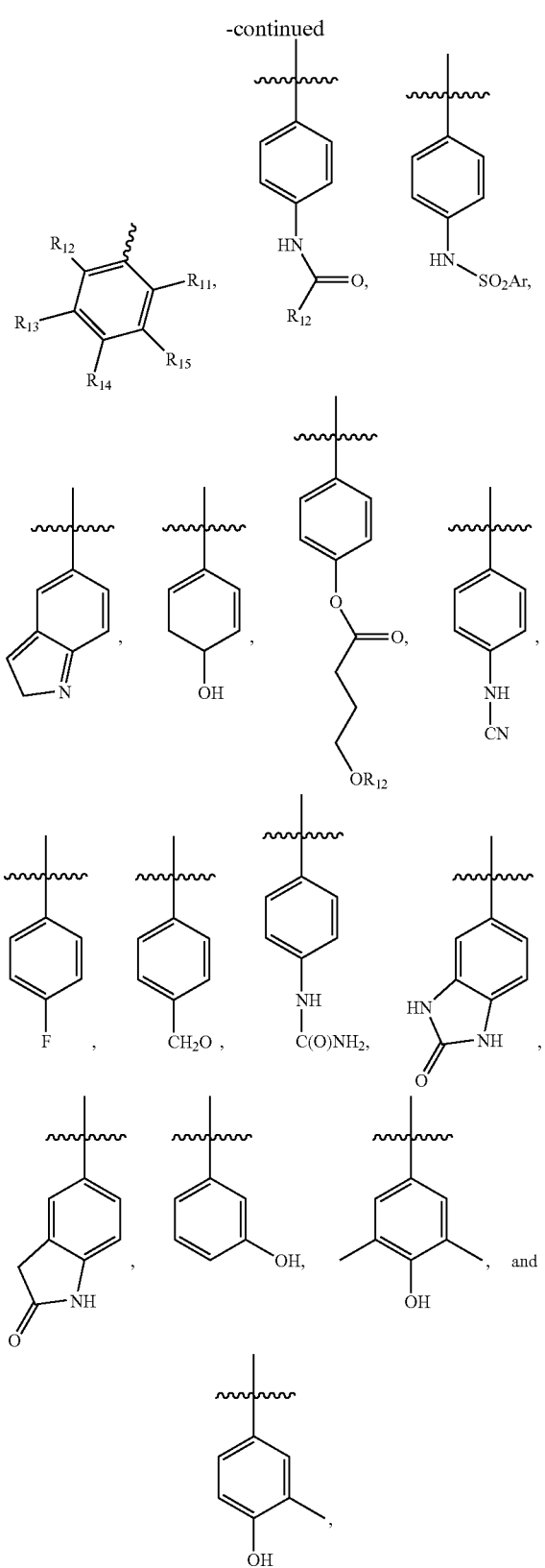

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In other preferred embodiments, R1 or R4 are selected from group consisting of: napthalalanine; phenol; 1-Napthalenol; 2-Napthalenol;

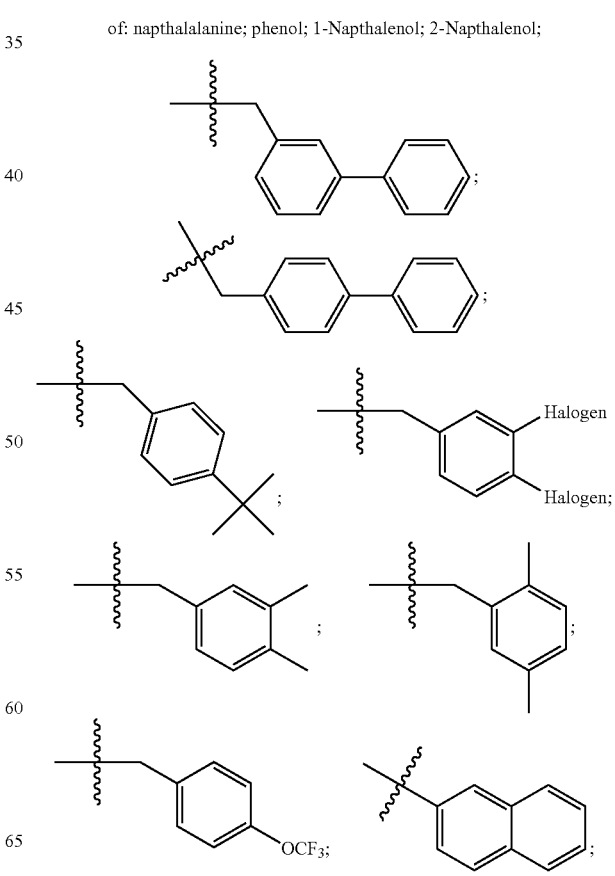

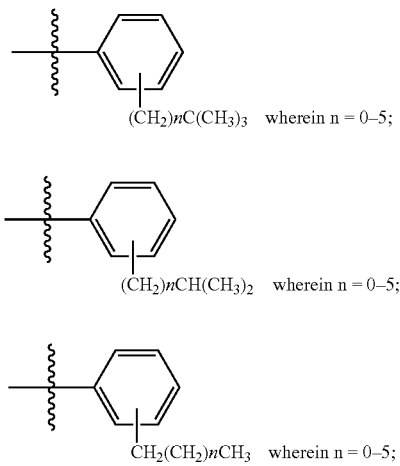

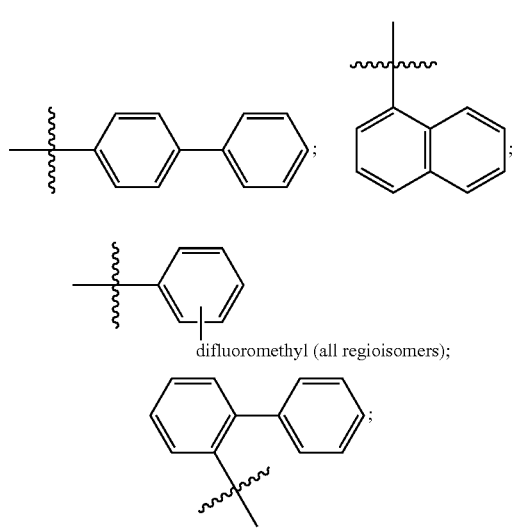

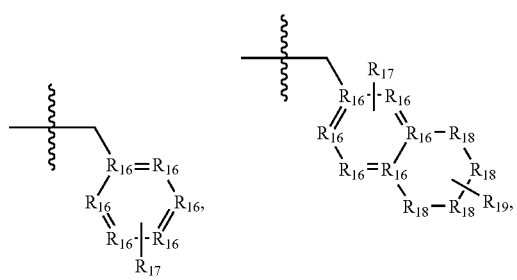

quinolines, and all aromatic regioisomers.

In preferred embodiments, R1 or R5 is selected from the group consisting of:

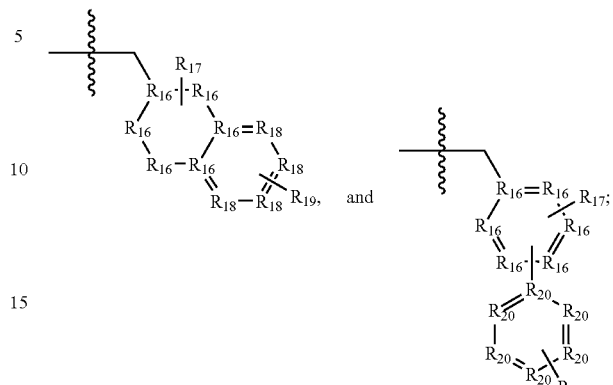

wherein R16 is carbon or nitrogen; wherein R17 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In certain embodiments, the present invention provides a composition comprising the following formula:

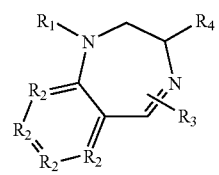

including both R and S enantiomeric forms and racemic mixtures; wherein R1 and R4 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R2 is carbon or nitrogen; and wherein R3 comprises a chemical moiety comprising a heterocyclic group containing 3 or more carbon atoms.

In preferred embodiments, the composition comprises the formula:

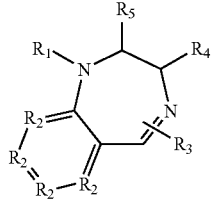

wherein R5 is selected from the group consisting of H and ketone.

In other preferred embodiments, R3 is selected from the group consisting of:

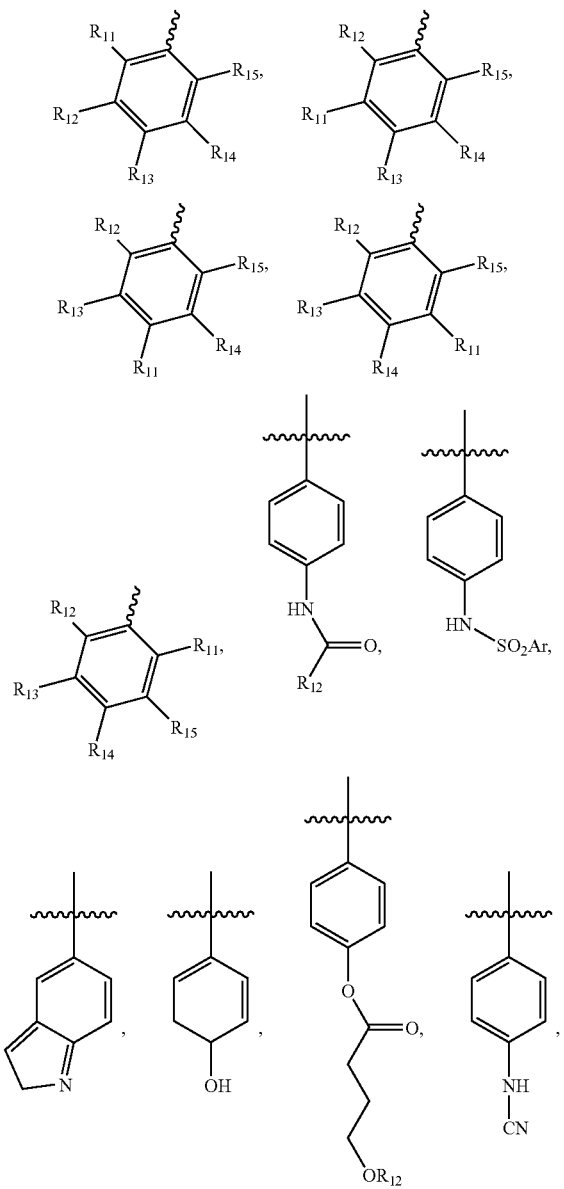

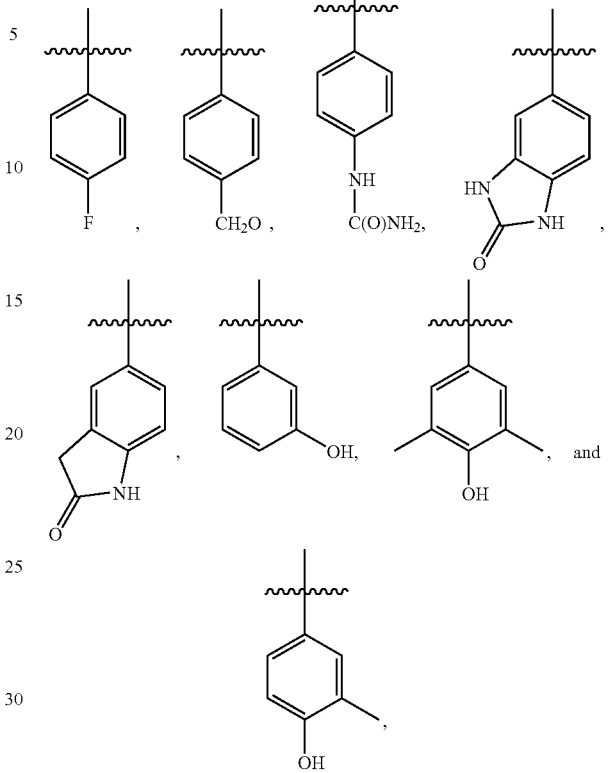

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In yet other preferred embodiments, R1 or R4 is selected from group consisting of: napthalalanine; phenol; 1-Napthalenol; 2-Napthalenol;

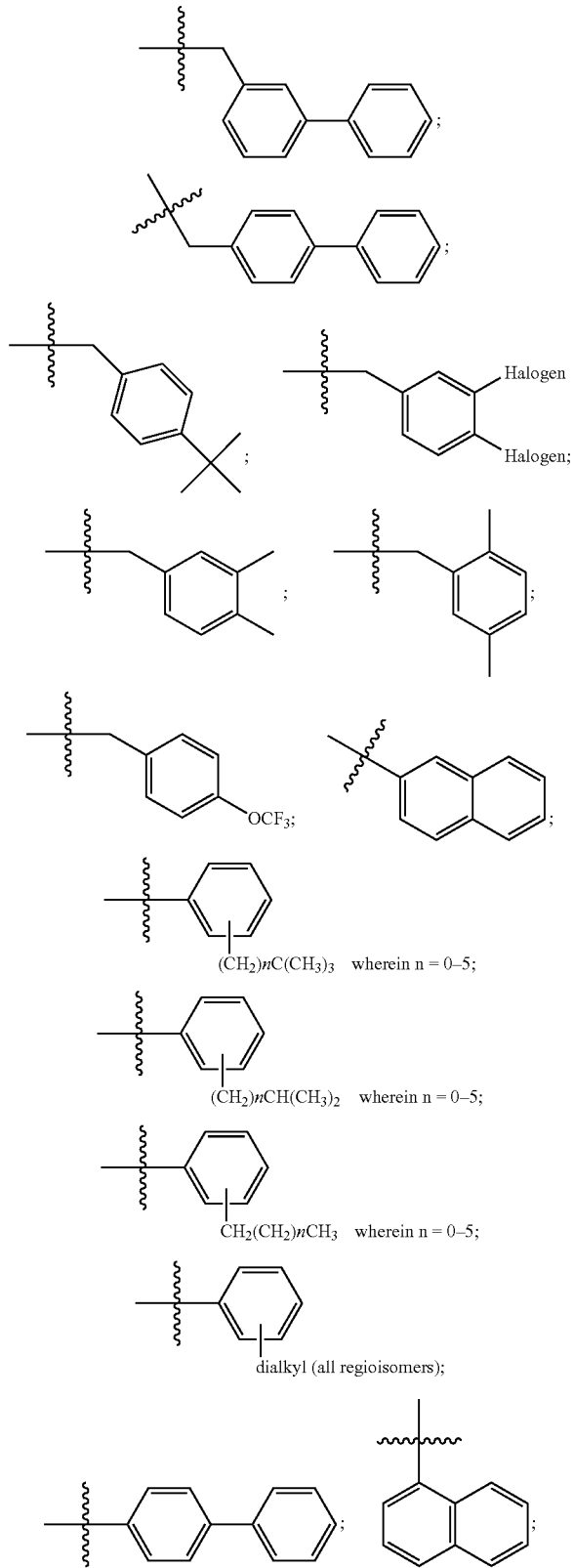

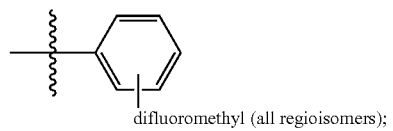

difluoromethyl (all regioisomers);

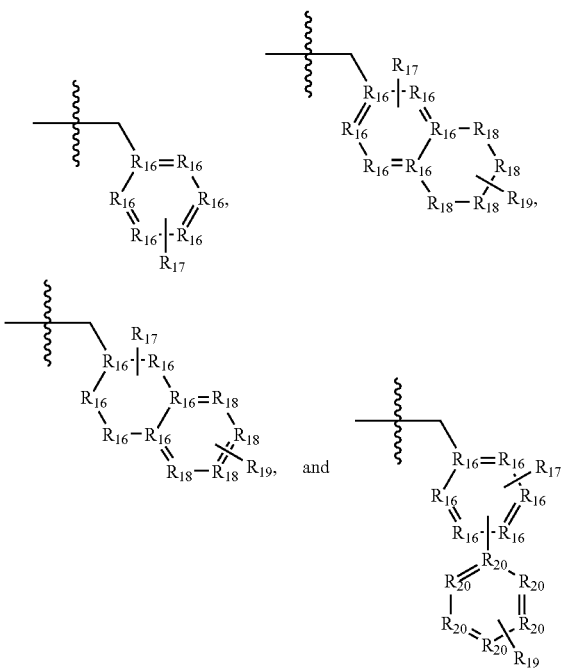

quinolines, and all aromatic regioisomers.

In preferred embodiments, R1 or R4 is selected from the group consisting of:

wherein R16 is carbon or nitrogen; wherein R17 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In certain embodiments, the present invention provides a composition comprising the following formula:

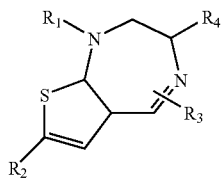

including both R and S enantiomeric forms and racemic mixtures; wherein R1 and R4 are separately selected from the group consisting of: hydrogen; halogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R2 is selected from H, a hydroxy, an alkoxy, a halo, an amino, a lower-alkyl, a substituted-amino, an acetylamino, a hydroxyamino, an aliphatic group having 1-8 carbons and 1-20 hydrogens, a substituted aliphatic group of similar size, a cycloaliphatic group consisting of less than 10 carbons, a substituted cycloaliphatic group, an aryl, a heterocyclic, $NO_2$; SR'; and $NR'_2$, wherein R' is defined as a linear or branched, saturated or unsaturated aliphatic chain having at least one carbon; a linear or branched, saturated or unsaturated aliphatic chain having at least 2 carbons, and having at least one hydroxyl subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and wherein R3 comprises a chemical moiety comprising a heterocyclic group containing 3 or more carbon atoms.

In preferred embodiments, the composition comprises the formula:

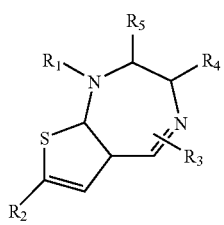

wherein R5 is selected from the group consisting of H and ketone.

In preferred embodiments, R3 is selected from the group consisting of:

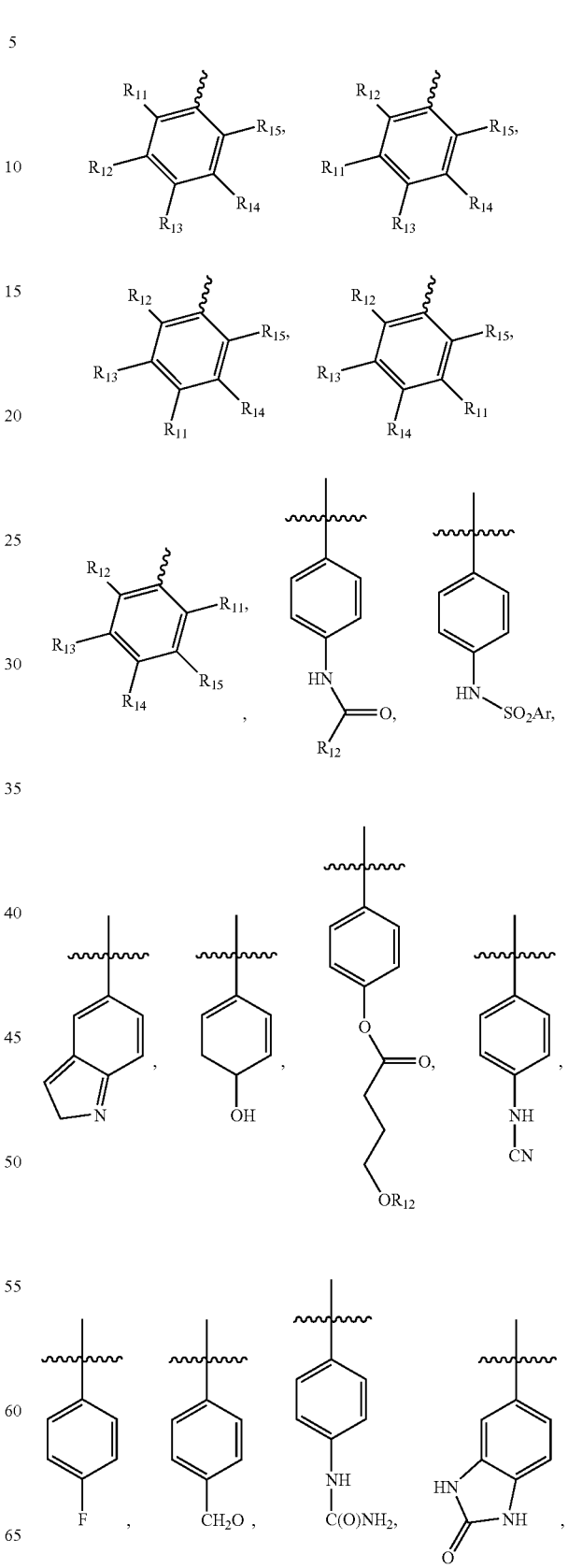

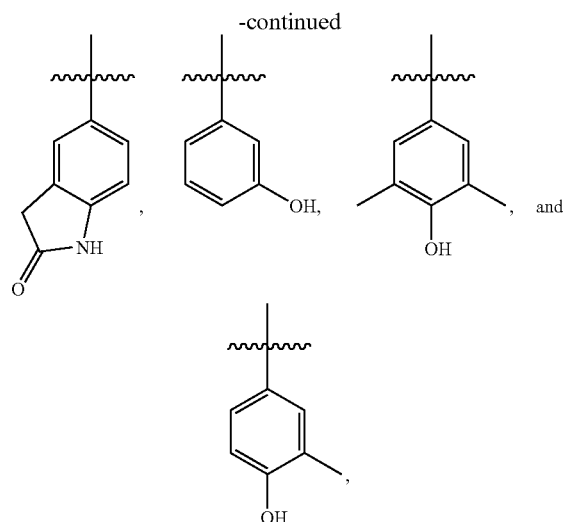

wherein R12, R13, R14 and R15 are selected from the group consisting of: hydrogen; $CH_3$; a linear or branched, saturated or unsaturated aliphatic chain having at least 1 carbon; a linear or branched, saturated or unsaturated aliphatic chain having at least 2 carbons, and having at least one hydroxy subgroup; a linear or branched, saturated or unsaturated aliphatic chain having at least 2 carbons, and having at least one thiol subgroup; a linear or branched, saturated or unsaturated aliphatic chain having at least 2 carbons, wherein the aliphatic chain terminates with an aldehyde subgroup; a linear or branched, saturated or unsaturated aliphatic chain having at least 2 carbons, and having at least one ketone subgroup; a linear or branched, saturated or unsaturated aliphatic chain having at least 2 carbons; wherein the aliphatic chain terminates with a carboxylic acid subgroup; a linear or branched, saturated or unsaturated aliphatic chain having at least 2 carbons, and having at least one amide subgroup; a linear or branched, saturated or unsaturated aliphatic chain having at least 2 carbons, and having at least one acyl group; a linear or branched, saturated or unsaturated aliphatic chain having at least 2 carbons, and having at least one nitrogen containing moiety; a linear or branched, saturated or unsaturated aliphatic chain having at least 2 carbons, and having at least one amine subgroup; a linear or branched, saturated or unsaturated aliphatic chain having at least 2 carbons, and having at least one ether subgroup; a linear or branched, saturated or unsaturated aliphatic chain having at least 2 carbons, and having at least one halogen subgroup; a linear or branched, saturated or unsaturated aliphatic chain having at least 2 carbons, and having at least one nitronium subgroup; and R11 is OH.

In other preferred embodiments, R1 or R4 is selected from group consisting of: napthalalanine; phenol; 1-Napthalenol; 2-Napthalenol;

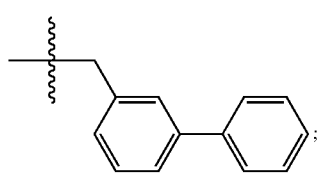

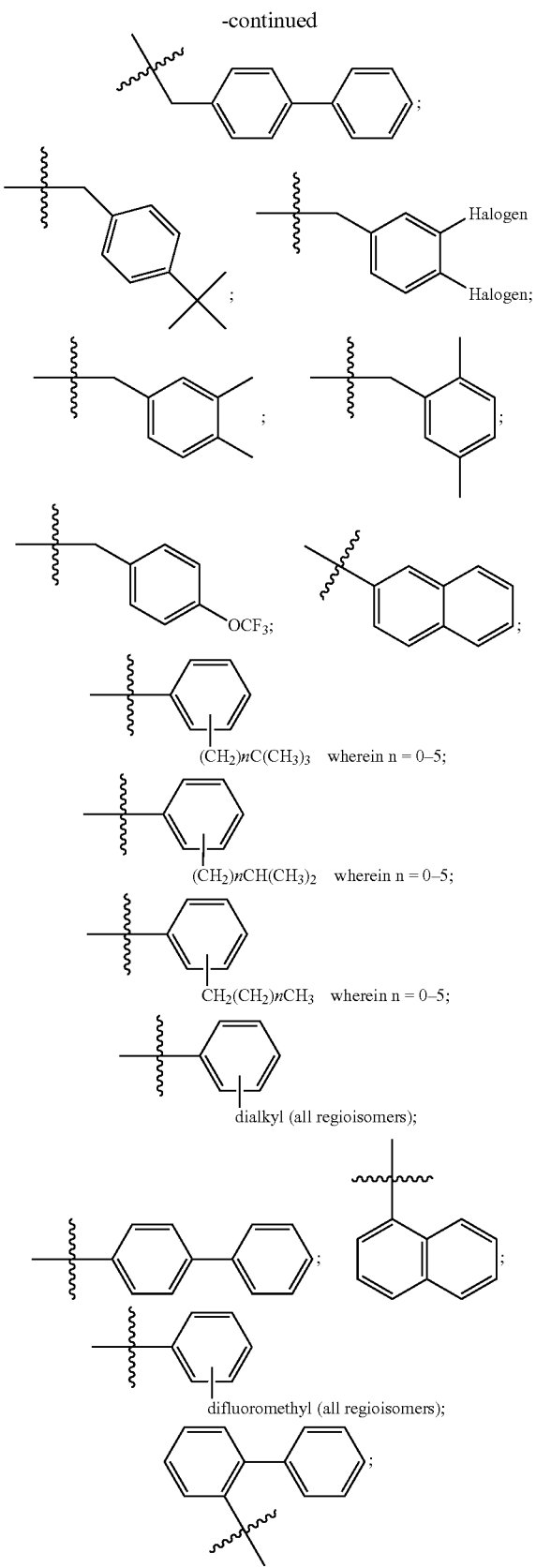

quinolines, and all aromatic regioisomers.

In preferred embodiments, R1 or R4 is selected from the group consisting of:

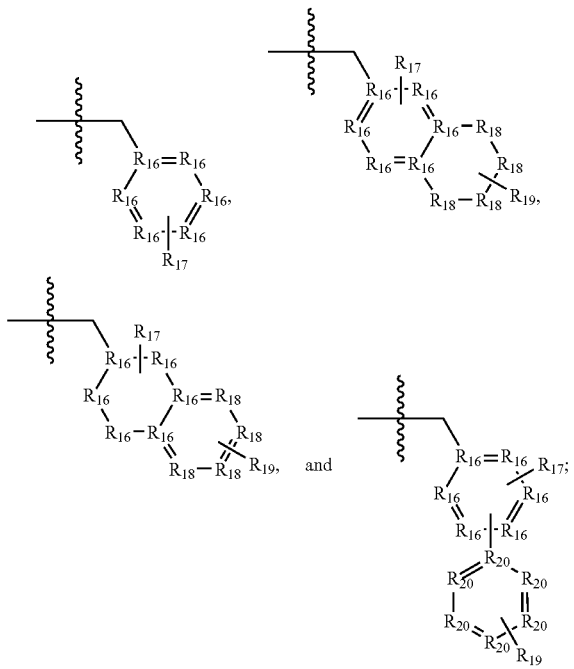

wherein R16 is carbon or nitrogen; wherein R17 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; wherein R18 is carbon or nitrogen; wherein R19 is selected from the group consisting of hydrogen; $CH_3$; a linear or branched, saturated or unsaturated aliphatic chain having at least 2 carbons; a chemical moiety comprising a halogen; a chemical moiety comprising Sulfur; a chemical moiety comprising Nitrogen; an aromatic chemical moiety; a hydrophilic chemical moiety; and a hydrophobic chemical moiety; and wherein R20 is carbon or nitrogen.

In summary, a large number of compounds are presented herein. Any one or more of these compounds can be used to treat a variety of dysregulatory disorders related to cellular death as described elsewhere herein. The above-described compounds can also be used in drug screening assays and other diagnostic methods.

IV. Pharmaceutical Compositions, Formulations, and Exemplary Administration Routes and Dosing Considerations Exemplary embodiments of various contemplated medicaments and pharmaceutical compositions are provided below.

A. Preparing Medicaments

It is contemplated that the compounds of the present invention are useful in the preparation of medicaments to treat a variety of conditions associated with dysregulation of cell death, aberrant cell growth and hyperproliferation.

In addition, it is contemplated that the compounds are also useful for preparing medicaments for treating other disorders wherein the effectiveness of the compounds are known or predicted. Such disorders include, but are not limited to, neurological (e.g., epilepsy) or neuromuscular disorders. The methods and techniques for preparing medicaments of a compound of the present invention are well-known in the art. Exemplary pharmaceutical formulations and routes of delivery are described below.

One of skill in the art will appreciate that any one or more of the compounds described herein, including the many specific embodiments, are prepared by applying standard pharmaceutical manufacturing procedures. Such medicaments can be delivered to the subject by using delivery methods that are well-known in the pharmaceutical arts.

B. Exemplary Pharmaceutical Compositions and Formulation

In some embodiments of the present invention, the compositions are administered alone, while in some other embodiments, the compositions are preferably present in a pharmaceutical formulation comprising at least one active ingredient/agent, as defined above, together with a solid support or alternatively, together with one or more pharmaceutically acceptable carriers and optionally other therapeutic agents (e.g., a benzodiazepine compound as described in U.S. patent application Ser. Nos. 10/886,450, 10/795,535, 10/634,114, 10/427,211, 10/217,878, 09/767,283, and 09/700,101 and U.S. Provisional Patent Application Nos. 60/607,599 and 60/565,788; each herein incorporated by reference in their entireties.). Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. In preferred embodiments, compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose)surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternatively embodiments, topical formulations comprise patches or dressings such as a bandage or adhesive plasters impregnated with active ingredient(s), and optionally one or more excipients or diluents. In preferred embodiments, the topical formulations include a compound(s) that enhances absorption or penetration of the active agent(s) through the skin or other affected areas. Examples of such dermal penetration enhancers include dimethylsulfoxide (DMSO) and related analogues.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in an known manner. This phase typically comprises an lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

Emulgents and emulsion stabilizers suitable for use in the formulation of the present invention include Tween 60, Span 80, cetostearyl alcohol, myristyl alcohol, glyceryl monostearate and sodium lauryl sulfate.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate.

Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, an include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily subdose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoelic acid), extenders, and stabilizers, etc.

C. Exemplary Administration Routes and Dosing Considerations

Various delivery systems are known and can be used to administer therapeutic agents (e.g., exemplary compounds as described in Section III above) of the present invention, e.g., encapsulation in liposomes, microparticles, microcapsules, receptor-mediated endocytosis, and the like. Methods of delivery include, but are not limited to, intra-arterial, intramuscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

It is contemplated that the agents identified can be administered to subjects or individuals susceptible to or at risk of developing pathological growth of target cells and correlated conditions. When the agent is administered to a subject such as a mouse, a rat or a human patient, the agent can be added to a pharmaceutically acceptable carrier and systemically or topically administered to the subject. To determine patients that can be beneficially treated, a tissue sample is removed from the patient and the cells are assayed for sensitivity to the agent.

Therapeutic amounts are empirically determined and vary with the pathology being treated, the subject being treated and the efficacy and toxicity of the agent. When delivered to an animal, the method is useful to further confirm efficacy of the agent. One example of an animal model is MLR/MpJ-lpr/lpr ("MLR-lpr") (available from Jackson Laboratories, Bal Harbor, Me.). MLR-lpr mice develop systemic autoimmune disease. Alternatively, other animal models can be developed by inducing tumor growth, for example, by subcutaneously inoculating nude mice with about $10^5$ to about $10^9$ hyperproliferative, cancer or target cells as defined herein. When the tumor is established, the compounds described herein are administered, for example, by subcutaneous injection around the tumor. Tumor measurements to determine reduction of tumor size are made in two dimensions using venier calipers twice a week. Other animal models may also be employed as appropriate. Such animal models for the above-described diseases and conditions are well-known in the art.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or nonaqueous diluents, syrups, granulates or powders. In addition to an agent of the present invention, the pharmaceutical compositions can also contain other pharmaceutically active compounds or a plurality of compounds of the invention.

More particularly, an agent of the present invention also referred to herein as the active ingredient, may be administered for therapy by any suitable route including, but not limited to, oral, rectal, nasal, topical (including, but not limited to, transdermal, aerosol, buccal and sublingual), vaginal, parental (including, but not limited to, subcutaneous, intramuscular, intravenous and intradermal) and pulmonary. It is also appreciated that the preferred route varies with the condition and age of the recipient, and the disease being treated.

Ideally, the agent should be administered to achieve peak concentrations of the active compound at sites of disease. This may be achieved, for example, by the intravenous injection of the agent, optionally in saline, or orally administered, for example, as a tablet, capsule or syrup containing the active ingredient.

Desirable blood levels of the agent may be maintained by a continuous infusion to provide a therapeutic amount of the active ingredient within disease tissue. The use of operative combinations is contemplated to provide therapeutic combinations requiring a lower total dosage of each component antiviral agent than may be required when each individual therapeutic compound or drug is used alone, thereby reducing adverse effects.

D. Exemplary Co-Administration Routes and Dosing Considerations

The present invention also includes methods involving co-administration of the compounds described herein with one or more additional active agents. Indeed, it is a further aspect of this invention to provide methods for enhancing prior art therapies and/or pharmaceutical compositions by co-administering a compound of this invention. In co-administration procedures, the agents may be administered concurrently or sequentially. In one embodiment, the compounds described herein are administered prior to the other active agent(s). The pharmaceutical formulations and modes of administration may be any of those described above. In addition, the two or more co-administered chemical agents, biological agents or radiation may each be administered using different modes or different formulations.

The agent or agents to be co-administered depends on the type of condition being treated. For example, when the condition being treated is cancer, the additional agent can be a chemotherapeutic agent or radiation. When the condition being treated is an autoimmune disorder, the additional agent can be an immunosuppressant or an anti-inflammatory agent. When the condition being treated is chronic inflammation, the additional agent can be an anti-inflammatory agent. The additional agents to be co-administered, such as anticancer, immunosuppressant, anti-inflammatory, and can be any of the well-known agents in the art, including, but not limited to, those that are currently in clinical use. The determination of appropriate type and dosage of radiation treatment is also within the skill in the art or can be determined with relative ease.

Treatment of the various conditions associated with abnormal apoptosis is generally limited by the following two major factors: (1) the development of drug resistance and (2) the toxicity of known therapeutic agents. In certain cancers, for example, resistance to chemicals and radiation therapy has been shown to be associated with inhibition of apoptosis. Some therapeutic agents have deleterious side effects, including non-specific lymphotoxicity, renal and bone marrow toxicity.

The methods described herein address both these problems. It is contemplated that drug resistance, where increasing dosages are required to achieve therapeutic benefit, is overcome by co-administering the compounds described herein with the known agent. It is contemplated that the compounds described herein sensitize target cells to known agents (and vice versa) and, accordingly, less of these agents are needed to achieve a therapeutic benefit.

It is contemplated that the sensitizing function of the claimed compounds also address the problems associated with toxic effects of known therapeutics. In instances where the known agent is toxic, it is desirable to limit the dosages administered in all cases, and particularly in those cases were drug resistance has increased the requisite dosage. It is contemplated that when the claimed compounds are co-administered with the known agent, they reduce the dosage required which, in turn, reduces the deleterious effects. Further, because the claimed compounds are contemplated to be both effective and non-toxic in large doses, co-administration of proportionally more of these compounds than known toxic therapeutics will achieve the desired effects while minimizing toxic effects.

V. Drug Screens

In preferred embodiments of the present invention, the compounds of the present invention, and other potentially useful compounds, are screened for their binding affinity to the oligomycin sensitivity conferring protein (OSCP) portion of the mitochondrial ATP synthase complex. In particularly preferred embodiments, compounds are selected for use in the methods of the present invention by measuring their binding affinity to recombinant OSCP protein. A number of suitable screens for measuring the binding affinity of drugs and other small molecules to receptors are known in the art. In some embodiments, binding affinity screens are conducted in in vitro systems. In other embodiments, these screens are conducted in in vivo or ex vivo systems. While in some embodiments quantifying the intracellular level of ATP following administration of the compounds of the present invention provides an indication of the efficacy of the methods, preferred embodiments of the present invention do not require intracellular ATP or pH level quantification.

Additional embodiments are directed to measuring levels (e.g., intracellular) of superoxide in cells and/or tissues to measure the effectiveness of particular contemplated methods and compounds of the present invention. In this regard, those skilled in the art will appreciate and be able to provide a number of assays and methods useful for measuring superoxide levels in cells and/or tissues.

In some embodiments, structure-based virtual screening methodologies are contemplated for predicting the binding affinity of compounds of the present invention with OSCP. In some preferred embodiments, compound structures are predicted from a molecular modeling software (e.g., Macro-Model).

Any suitable assay that allows for a measurement of the rate of binding or the affinity of an exemplary compound of the present invention to the OSCP may be utilized. Examples include, but are not limited to, competition binding using an exemplary compound, surface plasma resonance (SPR) and radio-immunopreciptiation assays (Lowman et al., J. Biol. Chem. 266:10982 [1991]). Surface Plasmon Resonance techniques involve a surface coated with a thin film of a conductive metal, such as gold, silver, chrome or aluminum, in which electromagnetic waves, called Surface Plasmons, can be induced by a beam of light incident on the metal glass interface at a specific angle called the Surface Plasmon Resonance angle. Modulation of the refractive index of the interfacial region between the solution and the metal surface following binding of the captured macromolecules causes a change in the SPR angle which can either be measured directly or which causes the amount of light reflected from the underside of the metal surface to change. Such changes can be directly related to the mass and other optical properties of the molecules binding to the SPR device surface. Several biosensor systems based on such principles have been disclosed (See e.g., WO 90/05305). There are also several commercially available SPR biosensors (e.g., BiaCore, Uppsala, Sweden).

In some embodiments, copmpounds are screened in cell culture or in vivo (e.g., non-human or human mammals) for an ability to modulate mitochondrial ATP synthase activity. Any suitable assay may be utilized, including, but not limited to, cell proliferation assays (Commercially available from, e.g., Promega, Madison, Wis. and Stratagene, La Jolla, Calif.) and cell based dimerization assays. (See e.g., Fuh et al., Science, 256:1677 [1992]; Colosi et al., J. Biol. Chem., 268: 12617 [1993]). Additional assay formats that find use with the present invention include, but are not limited to, assays for measuring cellular ATP levels, and cellular superoxide levels.

The present invention also provides methods of modifying and derivatizing the compositions of the present invention to increase desirable properties (e.g., binding affinity, activity, and the like), or to minimize undesirable properties (e.g., nonspecific reactivity, toxicity, and the like). The principles of chemical derivatization are well understood. In some embodiments, iterative design and chemical synthesis approaches are used to produce a library of derivatized child compounds from a parent compound. In other embodiments, rational design methods are used to predict and model in silico ligand-receptor interactions prior to confirming results by routine experimentation.

VI. Therapeutic Application

In certain embodiments, the present invention provides methods (e.g., therapeutic applications) for regulating cell death comprising: a) providing: i. target cells having mitochondria; and ii. a composition (e.g., exemplary compounds as described in Section III above); and b) exposing the target cells to the composition under conditions such that the exposure results in cell death. In preferred embodiments, the composition binds to the mitochondria so as to increase superoxide levels or alter cellular ATP levels in the target cells. Method of the present invention are not limited to particular target cells. In some preferred embodiments, the target cells are selected from the group consisting of in vitro cells, in vivo cells, ex vivo cells, cancer cells, B cells, T cells, and granulocytes. The present invention is not limited to a particular therapeutic application. Non-limiting examples of therapeutic applications for the present invention are described in the following subsections.

A. General Therapeutic Application

In particularly preferred embodiments, the compositions of the present invention are contemplated to provide therapeutic benefits to patients suffering from any one or more of a number of conditions (e.g., diseases characterized by dysregulation of necrosis and/or apoptosis processes in a cell or tissue, disease characterized by aberrant cell growth and/or hyperproliferation, etc.) by modulating (e.g., inhibiting or promoting) the activity of the mitochondrial ATP synthase (as referred to as mitochondrial $F_0F_1$ ATPase) complexes in affected cells or tissues. In further preferred embodiments, it is contemplated that the compositions of the present invention are used to treat autoimmune/chronic inflammatory conditions (e.g., psoriasis). In even further embodiments, it is contemplated that the compositions of the present invention are used in conjunction with stenosis therapy to treat compromised (e.g., occluded) vessels.

In particularly preferred embodiments, it is contemplated that the compositions of the present invention inhibit the activity of mitochondrial ATP synthase complex by binding to a specific subunit of this multi-subunit protein complex. While the present invention is not limited to any particular mechanism, nor to any understanding of the action of the agents being administered, in some embodiments, it is contemplated that the compositions of the present invention bind to the oligomycin sensitivity conferring protein (OSCP) portion of the mitochondrial ATP synthase complex. Likewise, it is further contemplated that when the compositions of the present invention bind to the OSCP the initial affect is overall inhibition of the mitochondrial ATP synthase complex, and that the downstream consequence of binding is a change in ATP or pH level and the production of reactive oxygen species (e.g., $O_2-$). In still other preferred embodiments, while the present invention is not limited to any particular mechanism, nor to any understanding of the action of the agents being administered, it is contemplated that the generation of free radicals ultimately results in cell killing. In yet other embodiments, while the present invention is not limited to any particular mechanism, nor to any understanding of the action of the agents being administered, it is contemplated that the inhibiting mitochondrial ATP synthase complex using the compositions and methods of the present invention provides therapeutically useful inhibition of cell proliferation.

Accordingly, it is contemplated that preferred methods embodied in the present invention, provide therapeutic benefits to patients by providing compounds of the present invention that modulate (e.g., inhibiting or promoting) the activity of the mitochondrial ATP synthase complexes in affected cells or tissues via binding to the oligomycin sensitivity conferring protein (OSCP) portion of the mitochondrial ATP synthase complex. Importantly, by itself the OSCP has no biological activity.

Thus, in one broad sense, it is contemplated that preferred embodiments of the present invention are directed to the discovery that many diseases characterized by dysregulation of necrosis and/or apoptosis processes in a cell or tissue, or diseases characterized by aberrant cell growth and/or hyperproliferation, etc., can be treated by modulating the activity of the mitochondrial ATP synthase complex including, but not limited to, by binding to the oligomycin sensitivity conferring protein (OSCP) component thereof. The present invention is not intended to be limited, however, to the practice of the compositions and methods explicitly described herein. Indeed, those skilled in the art will appreciate that a number of additional compounds not specifically recited herein are suitable for use in the methods disclosed herein of modulating the activity of mitochondrial ATP synthase.

The present invention thus specifically contemplates that any number of suitable compounds presently known in the art, or developed later, can optionally find use in the methods of the present invention. For example, compounds including, but not limited to, oligomycin, ossamycin, cytovaricin, apoptolidin, bafilomyxcin, resveratrol, piceatannol, and dicyclohexylcarbodiimide (DCCD), and the like, find use in the methods of the present invention. The present invention is not intended, however, to be limited to the methods or compounds specified above. In one embodiment, that compounds potentially useful in the methods of the present invention may be selected from those suitable as described in the scientific literature. (See e.g., K. B. Wallace and A. A. Starkov, Annu. Rev. Pharmacol. Toxicol., 40:353-388 [2000]; A. R. Solomon et al., Proc. Nat. Acad. Sci. U.S.A., 97(26):14766-14771 [2000]).

In some embodiments, compounds potentially useful in methods of the present invention are screened against the National Cancer Institute's (NCI-60) cancer cell lines for efficacy. (See e.g., A. Monks et al., J. Natl. Cancer Inst., 83:757-766 [1991]; and K. D. Paull et al., J. Natl. Cancer Inst., 81:1088-1092 [1989]). Additional screens suitable screens (e.g., autoimmunity disease models, etc.) are within the skill in the art.

In one aspect, derivatives (e.g., pharmaceutically acceptable salts, analogs, stereoisomers, and the like) of the exemplary compounds or other suitable compounds are also contemplated as being useful in the methods of the present invention.

In other preferred embodiments, it is contemplated that the compositions of the present invention are used in conjunction with stenosis therapy to treat compromised (e.g., occluded) vessels. In further embodiments, it is contemplated that the compositions of the present invention are used in conjunction with stenosis therapy to treat compromised cardiac vessels.

Vessel stenosis is a condition that develops when a vessel (e.g., aortic valve) becomes narrowed. For example, aortic valve stenosis is a heart condition that develops when the valve between the lower left chamber (left ventricle) of the heart and the major blood vessel called the aorta becomes narrowed. This narrowing (e.g., stenosis) creates too small a space for the blood to flow to the body. Normally the left ventricle pumps oxygen-rich blood to the body through the aorta, which branches into a system of arteries throughout the body. When the heart pumps, the 3 flaps, or leaflets, of the aortic valve open one way to allow blood to flow from the ventricle into the aorta. Between heartbeats, the flaps close to form a tight seal so that blood does not leak backward through the valve. If the aortic valve is damaged, it may become narrowed (stenosed) and blood flow may be reduced to organs in the body, including the heart itself. The long-term outlook for people with aortic valve stenosis is poor once symptoms develop. People with untreated aortic valve stenosis who develop symptoms of heart failure usually have a life expectancy of 3 years or less.

Several types of treatment exist for treating compromised valves (e.g., balloon dilation, ablation, atherectomy or laser treatment). One type of treatment for compromised cardiac valves is angioplasty. Angioplasty involves inserting a balloon-tipped tube, or catheter, into a narrow or blocked artery in an attempt to open it. By inflating and deflating the balloon several times, physicians usually are able to widen the artery.

A common limitation of angioplasty or valve expansion procedures is restenosis. Restenosis is the reclosure of a peripheral or coronary artery following trauma to that artery caused by efforts to open a stenosed portion of the artery, such as, for example, by balloon dilation, ablation, atherectomy or laser treatment of the artery. For these angioplasty procedures, restenosis occurs at a rate of about 20-50% depending on the definition, vessel location, lesion length and a number of other morphological and clinical variables. Restenosis is believed to be a natural healing reaction to the injury of the arterial wall that is caused by angioplasty procedures. The healing reaction begins with the thrombotic mechanism at the site of the injury. The final result of the complex steps of the healing process can be intimal hyperplasia, the uncontrolled migration and proliferation of medial smooth muscle cells, combined with their extracellular matrix production, until the artery is again stenosed or occluded.

In an attempt to prevent restenosis, metallic intravascular stents have been permanently implanted in coronary or peripheral vessels. The stent is typically inserted by catheter into a vascular lumen told expanded into contact with the diseased portion of the arterial wall, thereby providing mechanical support for the lumen. However, it has been found that restenosis can still occur with such stents in place. Also, the stent itself can cause undesirable local thrombosis. To address the problem of thrombosis, persons receiving stents also receive extensive systemic treatment with anticoagulant and antiplatelet drugs.

To address the restenosis problem, it has been proposed to provide stents which are seeded with endothelial cells (Dichek, D. A. et al; Circulation 1989; 80: 1347-1353). In that experiment, sheep endothelial cells that had undergone retrovirus-mediated gene transfer for either bacterial beta-galactosidase or human tissue-type plasminogen activator were seeded onto stainless steel stents and grown until the stents were covered. The cells were therefore able to be delivered to the vascular wall where they could provide therapeutic proteins. Other methods of providing therapeutic substances to the vascular wall by means of stents have also been proposed (see, e.g., International Patent Applications WO 91/12779, and WO 90/13332; each herein incorporated by reference in their entirities). In those applications, it is suggested that antiplatelet agents, anticoagulant agents, antimicrobial agents, anti-inflammatory agents, antimetabolic agents and other drugs could be supplied in stents to reduce the incidence of restenosis. Further, other vasoreactive agents such as nitric oxide releasing agents could also be used.

An additional cause of restenosis is the over-proliferation of treated tissue. In preferred embodiments, it is contemplated that the anti-proliferative properties of the present invention inhibit restenosis. Drug-eluting stents are well known in the art (see, e.g., U.S. Pat. Nos. 5,697,967; 5,599,352; and 5,591,227; each of which are herein incorporated by reference). In preferred embodiments, the compositions of the present invention are eluted from drug-eluting stents in the treatment of compromised (e.g., occluded) vessels. In further embodiments, the compositions of the present invention are eluted from drug-eluting stents in the treatment of compromised cardiac vessels.

In additional applications, compositions and compounds of the present invention are used as anti-aging (e.g., lifespan extending) agents (see, e.g., Howitz, K T (2003) Nature 425: 191-196; herein incorporated by reference in its entirety).

Those skilled in the art of preparing pharmaceutical compounds and formulations will appreciate that when selecting optional compounds for use in the methods disclosed herein, that suitability considerations include, but are not limited to, the toxicity, safety, efficacy, availability, and cost of the particular compounds.

B. Autoimmune Disorder and Chronic Inflammatory Disorder Therapeutic Application Autoimmune disorders and chronic inflammatory disorders often result from dysfunctional cellular proliferation regulation and/or cellular apoptosis regulation. Mitochondria perform a key role in the control and execution of cellular apoptosis. The mitochondrial permeability transition pore (MPTP) is a pore that spans the inner and outer mitochondrial membrandes and functions in the regulation of proapoptotic particles. Transient MPTP opening results in the release of cytochrome c and the apoptosis inducing factor from the mitochondrial intermembrane space, resulting in cellular apoptosis.

The oligomycin sensitivity conferring protein (OSCP) is a subunit of the $F_0F_1$ mitochondrial ATP synthase/ATPase and functions in the coupling of a proton gradient across the $F_0$ sector of the enzyme in the mitochondrial membrane. In preferred embodiments, it is contemplated that compounds of the present invention bind the OSCP, increases superoxide and cytochrome c levels, increases cellular apoptosis, and inhibits cellular proliferation. The adenine nucleotide translocator (ANT) is a 30 kDa protein that spans the inner mitochondrial membrane and is central to the mitochondrial permeability transition pore (MPTP). Thiol oxidizing or alkylating agents are powerful activators of the MPTP that act by modifying one or more of three unpaired cysteines in the matrix side of the ANT. 4-(N-(S-glutathionylacetyl)amino) phenylarsenoxide, inhibits the ANT.

C. Treatment of Epidermal Hyperplasia

Epidermal hyperplasia (e.g., excessive keratinocyte proliferation) leading to a significant thickening of the epidermis in association with shedding of the thickened epidermis, is a feature of diseases such as psoriasis (see, e.g., Krueger G C, et al., (1984) J. Am. Acad. Dermatol. 11: 937-947; Fry L. (1988), Brit. J. Dermatol. 119:445-461; each herein incorporated by reference in their entireties) and also occurs under physiological conditions (e.g., during wound-healing).

Topical treatment of the skin with all-trans retinoic acid (RA) or its precursor, all-trans retinol (ROL) also results in epidermal hyperplasia (see, e.g., Varani J, et al., (2001) J. Invest. Dermatol, 117:1335-1341; herein incorporated by reference in its entirety). While the underlying etiologies are different, all of these hyperplasias have in common the activation of the epidermal growth factor (EGF) receptor in the proliferating keratinocytes (see, e.g., Varani J, et al., (2001) J. Invest. Dermatol 117:1335-1341; Baker B S, et al., (1992) Brit. J. Dermatol. 126:105-110; Gottlieb A B, et al., (1988) J. Exp. Med. 167:670-675; Elder J T, et al., (1989) Science 243:811-814; Piepkorn M, et al., (1998) J Invest Dermatol 111:715-721; Piepkorn M, et al., (2003) Arch Dermatol Res 27:27; Cook P W, et al., (1992) Cancer Res 52:3224-3227; each herein incorporated by reference in their entireties). Normal epidermal growth does not appear to be as dependent on EGF receptor function as hyperplastic growth (see, e.g., Varani J, et al., (2001) J. Invest. Dermatol 117:1335-1341; Varani J, et al., (1998) Pathobiology 66:253-259; each herein incorporated by reference in their entireties). Likewise, function of the dermis in intact skin does not depend on EGF receptor function (see, e.g., Varani J, et al., (2001) J. Invest. Dermatol 117:1335-1341; herein incorporated by reference in its entirety).

The central role of the EGF receptor in regulating hyperplastic epithelial growth makes the EGF receptor tyrosine kinase a target for antiproliferative agents. Likewise, the series of signaling molecules engaged downstream of this receptor are additional points at which keratinocyte growth can be interrupted. The mitogen activated protein kinase (MAPK) cascade is activated by the EGF receptor (see, e.g., Marques, S. A., et al., (2002) J Pharmacol Exp Ther 300, 1026-1035; herein incorporated by reference in its entirety). In hyperproliferative epidermis, but not in normal epidermis, extracellular signal-regulated kinases 1/2 (Erk 1/2) are activated in basal and suprabasal keratinocytes and contribute to epidermal hyperproliferation (see, e.g., Haase, I., et al., (2001) J Clin Invest 108, 527-536; Takahashi, H., et al., (2002) J Dermatol Sci 30, 94-99; each herein incorporated by reference in their entireties). In culture models, keratinocyte growth regulation through the EGF receptor results in increased MAPK activity. In keratinocytes, growth factor-stimulated MAPK activity is also dependent on integrin engagement and extracellular matrix molecules that bind integrins are capable of independently activating MAPKs and increasing keratinocyte proliferation (see, e.g., Haase, I., et al., (2001) J Clin Invest 108, 527-536; herein incorporated by reference in its entirety). The proliferation of other skin cells, including fibroblasts, is less dependent on Erk 1/2 activity, making Erk inhibition a potentially useful characteristic to evaluate lead compounds for potential utility against epidermal hyperplasia.

In preferred embodiments, it is contemplated that compounds of the present invention are useful for treating epidermal hyperplasias.

In preferred embodiments, it is contemplated that compounds of the present invention are useful in treating psoriasis. Psoriasis is common and chronic epidermal hyperplasia. Plaque psoriasis is the most common type of psoriasis and is characterized by red skin covered with silvery scales and inflammation. Patches of circular to oval shaped red plaques that itch or burn are typical of plaque psoriasis. The patches are usually found on the arms, legs, trunk, or scalp but may be found on any part of the skin. The most typical areas are the knees and elbows. Psoriasis is not contagious and can be inherited. Environmental factors, such as smoking, sun exposure, alcoholism, and HIV infection, may affect how often the psoriasis occurs and how long the flares up last.

Treatment of psoriasis includes topical steroids, coal tar, keratolytic agents, vitamin D-3 analogs, and topical retinoids. Topical steroids are agents used to reduce plaque formation. Topical steroid agents have anti-inflammatory effects and may cause profound and varied metabolic activities. In addition, topical steroid agents modify the body's immune response to diverse stimuli. Examples of topical steroids include, but are not limited to, triamcinolone acetonide (Artistocort, Kenalog) 0.1% cream, and betamethasone diprionate (Diprolene, Diprosone) 0.05% cream. Coal tar is an inexpensive treatment available over the counter in shampoos or lotions for use in widespread areas of involvement. Coal tar is particularly useful in hair-bearing areas. An example of coal tar is coal tar 2-10% (DHS Tar, Doctar, Theraplex T)-antipruitic. Keratolytic agents are used to remove scale, smooth the skin, and to treat hyperkeratosis. An example of a keratolytic agent is anthralin 0.1-1% (Dritho-creme, Anthra-Derm). Vitamin D-3 analogs are used in patients with lesions resistant to older therapy or with lesions on the face or exposed areas where thinning of the skin would pose cosmetic problems. An example of a vitamin D-3 analog is calcipotriene (Dovonex). Topical retinoids are agents that decrease the cohesiveness of follicular epithelial cells and stimulate mitotic activity, resulting in an increase in turnover of follicular epithelial cells. Examples of topical retinoids include, but are not limited to, tretinoin (Retin-A, Avita), and tazarotene (Tazorac).

Approximately 1-2% of people in the United States, or about 5.5 million, have plaque psoriasis. Up to 30% of people with plaque psoriasis also have psoriatic arthritis. Individuals with psoriatic arthritis have inflammation in their joints and may have other arthritis symptoms. Sometimes plaque psoriasis can evolve into more severe disease, such as pustular psoriasis or erythrodermic psoriasis. In pustular psoriasis, the red areas on the skin contain blisters with pus. In erythrodermic psoriasis, a wide area of red and scaling skin is typical, and it may be itchy and painful. The present invention is useful in treating additional types of psoriasis, including but not limited to, guttate psoriasis, nail psoriasis, inverse psoriasis, and scalp psoriasis.

VII. ATPase Inhibitors and Methods for Identifying Therapeutic Inhibitors

The present invention provides compounds that are contemplated to target the $F_1F_0$-ATPase. In addition, the present invention provides compounds that are contemplated to target the $F_1F_0$-ATPase as a treatment for autoimmune disorders, and in particular, compounds with low toxicity. The present invention further provides methods of identifying compounds that are contemplated to target the $F_1F_0$-ATPase. Additionally, the present invention provides therapeutic applications for compounds contemplated to target the $F_1F_0$-ATPase.

A majority of ATP within eukaryotic cells is synthesized by the mitochondrial $F_1F_0$-ATPase (see, e.g., C. T. Gregory et al., J. Immunol., 139:313-318 [1987]; J. P. Portanova et al., Mol. Immunol., 32:117-135 [1987]; M. J. Shlomchik et al., Nat. Rev. Immunol., 1:147-153 [2001]; each herein incorporated by reference in their entireties). Although the $F_1F_0$-ATPase synthesizes and hydrolyzes ATP, during normal physiologic conditions, the $F_1F_0$-ATPase only synthesizes ATP (see, e.g., Nagyvary J, et al., Biochem. Educ. 1999; 27:193-99; herein incorporated by reference in its entirety). The mitochondrial $F_1F_0$-ATPase is composed of three major domains: $F_0$, $F_1$ and the peripheral stator. $F_1$ is the portion of the enzyme that contains the catalytic sites and it is located in the matrix (see, e.g., Boyer, P D, Annu Rev Biochem. 1997; 66:717-49; herein incorporated by reference in its entirety). This domain is highly conserved and has the subunit composition $\alpha_3\beta_3\gamma\delta\epsilon$. The landmark X-ray structure of bovine $F_1$ revealed that $\alpha_3\beta_3$ forms a hexagonal cylinder with the $\gamma$ subunit in the center of the cylinder. $F_0$ is located within the inner mitochondrial membrane and contains a proton channel. Translocation of protons from the inner-membrane space into the matrix provides the energy to drive ATP synthesis. The peripheral stator is composed of several proteins that physically and functionally link $F_0$ with $F_1$. The stator transmits conformational changes from $F_0$ into in the catalytic domain that regulate ATP synthesis (see, e.g., Cross R L, Biochim Biophys Acta 2000; 1458:270-75; herein incorporated by reference in its entirety).

Mitochondrial $F_1F_0$-ATPase inhibitors are invaluable tools for mechanistic studies of the $F_1F_0$-ATPase (see, e.g., James A M, et al., J Biomed Sci 2002; 9:475-87; herein incorporated by reference in its entirety). Because $F_1F_0$-ATPase inhibitors are often cytotoxic, they have been explored as drugs for cancer and other hyperproliferative disorders. Macrolides (e.g., oligomycin and apoptolidin) are non-competitive inhibitors of the $F_1F_0$-ATPase (see, e.g., Salomon A R, et al., PNAS 2000; 97:14766-71; Salomon A R, et al., Chem Biol 2001; 8:71-80; herein incorporated by reference in its entirety). Macrolides bind to $F_0$ which blocks proton flow through the channel resulting in inhibition of the $F_1F_0$-ATPase. Macrolides are potent (e.g., the $IC_{50}$ for oligomycin=10 nM) and lead to large decreases in [ATP]. As such, macrolides have an unacceptably narrow therapeutic index and are highly toxic (e.g., the $LD_{50}$ for oligomycin in rodents is two daily doses at 0.5 mg/kg) (see, e.g., Kramar R, et al., Agents & Actions 1984, 15:660-63; herein incorporated by reference in its entirety). It is contemplated that inhibitors of $F_1F_0$-ATPase include the compounds of the present invention.

In cells that are actively respiring (known as state 3 respiration), inhibiting $F_1F_0$-ATPase blocks respiration and places the mitochondria in a resting state (known as state 4). In state 4, the MRC is reduced relative to state 3, which favors reduction of $O_2$ to $O_2^-$ at complex III (see, e.g., N. Zamzami et al., J. Exp. Med., 181:1661-1672 [1995]; herein incorporated by reference in its entirety). For example, treating cells with either oligomycin or, it is contemplated, compounds of the present invention, leads to a rise of intracellular $O_2^-$ as a consequence of inhibiting complex V. In the case of oligomycin, supplementing cells with ATP protects against death whereas antioxidants do not, indicating that cell death results from the drop in ATP (see, e.g., Zhang J G, et al., Arch Biochem Biophys 2001; 393:87-96; McConkey D J, et al., The ATP switch in apoptosis. In: Nieminen La, ed. Mitochondria in pathogenesis. New York: Plenum, 2001:265-77; each herein incorporated by reference in their entireties). Cell death induced by compounds of the present invention, it is contemplated, is blocked by antioxidants and is not affected by supplementing cells with ATP, suggesting that compounds of the present invention engage an ROS-dependent death response (see, e.g., N. B. Blatt, et al., J. Clin. Invest., 2002, 110, 1123; herein incorporated by reference in its entirety). As such, $F_1F_0$-ATPase inhibitors are either toxic (e.g., oligomycin) or, it is contemplated, therapeutic (e.g., compounds of the present invention).

The present invention provides a method of distinguishing toxic $F_1F_0$-ATPase inhibitors from therapeutic $F_1F_0$-ATPase inhibitors. $F_1F_0$-ATPase inhibitors with therapeutic potential (e.g., compounds of the present invention) present a novel mode of inhibition. Specifically, it is contemplated that $F_1F_0$-ATPase inhibitors with beneficial properties (e.g., compounds of the present invention) are uncompetitive inhibitors that only bind enzyme-substrate complexes at high substrate concentration and do not alter the $k_{cat}/K_m$ ratio. This knowledge forms the basis to identify and distinguish $F_1F_0$-ATPase inhibitors with therapeutic potential from toxic compounds.

The present invention provides compounds that are contemplated to target the $F_1F_0$-ATPase as an autoimmune disorder treatment. In particular, the present invention provides methods of identifying compounds that target the $F_1F_0$-ATPase while not altering the $k_{cat}/K_m$ ratio. Additionally, the present invention provides therapeutic applications for compounds targeting the $F_1F_0$-ATPase.

A. ATPase Inhibiting Compounds

The present invention provides compounds that are contemplated to inhibit the $F_1F_0$-ATPase. In some embodiments, it is contemplated that the compounds do not bind free $F_1F_0$-ATPase, but rather bind to an $F_1F_0$-ATPase-substrate complex. It is contemplated that the compounds show maximum activity at high substrate concentration and minimal activity (e.g., $F_1F_0$-ATPase inhibiting) at low substrate concentration. In preferred embodiments, it is contemplated that the compounds do not alter the $k_{cat}/K_m$ ratio of the $F_1F_0$-ATPase. It is contemplated that the properties of the $F_1F_0$-ATPase inhibitors of the present invention are in contrast with oligomycin, which is a $F_1F_0$-ATPase inhibitor that is acutely toxic and lethal. Oligomycin is a noncompetitive inhibitor, which binds to both free $F_1F_0$-ATPase and $F_1F_0$-ATPase-substrate complexes and alters the $k_{cat}/K_m$ ratio.

It is contemplated that he compounds of the present invention that inhibit $F_1F_0$-ATPase while not altering the $k_{cat}/K_m$ ratio, in some embodiments, have the structure described elsewhere herein. However, compounds of other structures that are identified as therapeutic inhibitors by the methods of the present invention are also encompassed by the present invention.

B. Identifying ATPase Inhibitors

The present invention provides methods of identifying (e.g., screening) compounds useful in treating autoimmune disorders. The present invention is not limited to a particular type compound. In preferred embodiments, compounds of the present invention include, but are not limited to, pharmaceutical compositions, small molecules, antibodies, large molecules, synthetic molecules, synthetic polypeptides, synthetic polynucleotides, synthetic nucleic acids, aptamers, polypeptides, nucleic acids, and polynucleotides. The present invention is not limited to a particular method of identifying compounds useful in treating autoimmune disorders. In preferred embodiments, compounds useful in treating autoimmune disorders are identified as possessing an ability to inhibit an $F_1F_0$-ATPase while not altering the $k_{cat}/K_m$ ratio.

C. Therapeutic Applications with $F_1F_0$-ATPase Inhibitors

The present invention provides methods for treating disorders (e.g., neurodegenerative diseases, Alzheimers, ischemia reprofusion injury, neuromotor disorders, non-Hodgkin's lymphoma, lymphocytic leukemia, cutaneous T cell leukemia, an autoimmune disorder, cancer, solid tumors, lymphomas, and leukemias). The present invention is not limited to a particular form of treatment. In preferred embodiments, treatment includes, but is not limited to, symptom amelioration, symptom prevention, disorder prevention, and disorder amelioration. The present invention provides methods of treating autoimmune disorders applicable within in vivo, in vitro, and/or ex vivo settings.

In some embodiments, the present invention treats autoimmune disorders through inhibiting of target cells. The present invention is not limited to a particular form of cell inhibition. In preferred embodiments, cell inhibition includes, but is not limited to, cell growth prevention, cell proliferation prevention, and cell death. In preferred embodiments, inhibition of a target cell is accomplished through contacting a target cell with a compound contemplated to inhibit the $F_1F_0$-ATPase. In further embodiments, target cell inhibition is accomplished through targeting of the $F_1F_0$-ATPase with a compound contemplated to inhibit the $F_1F_0$-ATPase. The present invention is not limited to a particular $F_1F_0$-ATPase inhibitor. In preferred embodiments, the $F_1F_0$-ATPase inhibitor is contemplated to possess an ability to inhibit an $F_1F_0$-ATPase while not altering the $k_{cat}/K_m$ ratio.

The present invention further provides methods for selectively inhibiting the pathology of target cells in a subject in need of therapy. The present invention is not limited to a particular method of inhibition target cell pathology. In preferred embodiments, it is contemplated that target cell pathology is inhibited through administration of an effective amount of a compound of the invention. The present invention is not limited to a particular compound. In preferred embodiments, it is contemplated that the compound is an $F_1F_0$-ATPase inhibitor. In further preferred embodiments, it is contemplated that the compound inhibits the $F_1F_0$-ATPase while not altering the $k_{cat}/K_m$ ratio.

EXAMPLES

Example 1

Detection of Cell Death

Ramos cells were exposed to the following compounds:

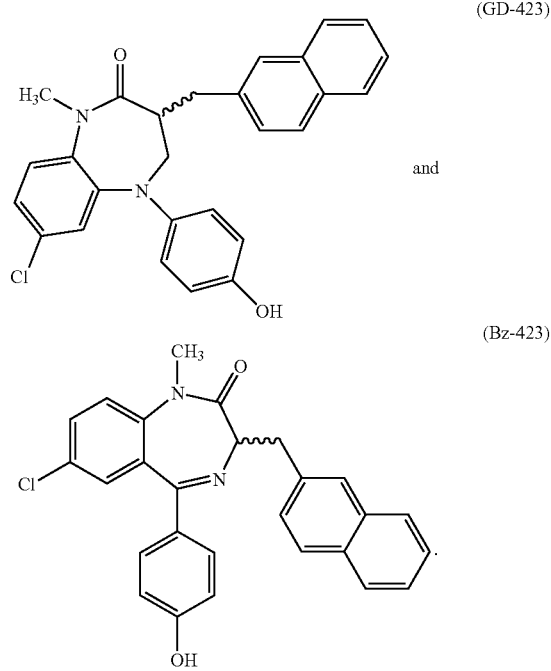

Each compound resulted in cellular death for the Ramos cells at 24 hours, 2% FBS (see, FIG. 1). Cell viability was assessed by staining with propidium iodide (PI, 1 µg/mL).

Ramos cells were exposed to the following compounds:

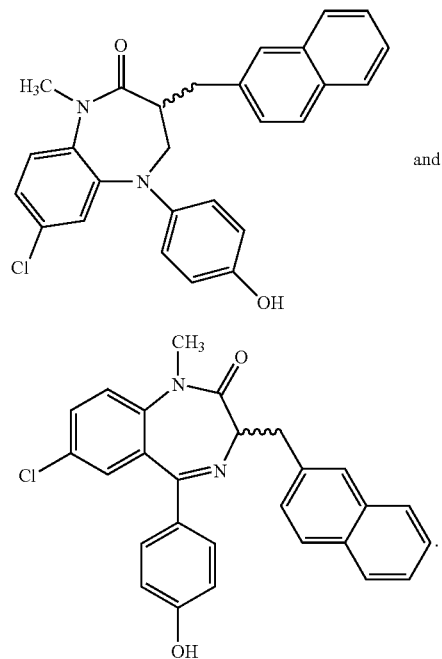

Figure 2:
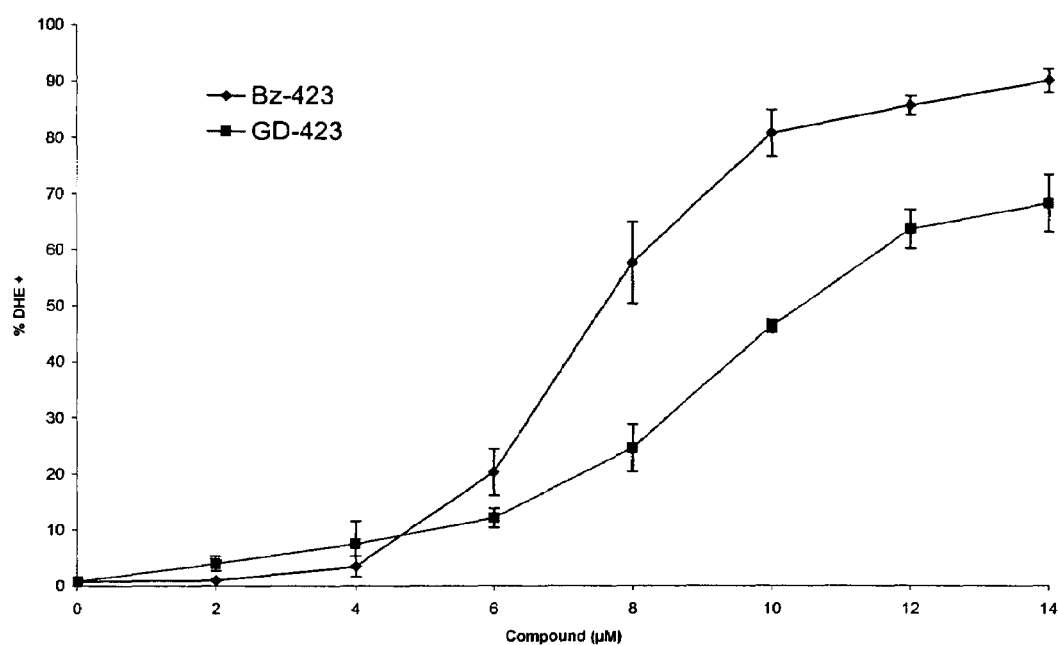
FIG. 2 shows data demonstrating that GD-423 causes cell death.

Each compound resulted in cellular death for the Ramos cells at 1 hour, 2% FBS (see, FIG. 2). To detect $O_2^-$, cells were incubated with dihydroethidium (DHE).

All publications and patents mentioned in the above specification are herein incorporated by reference. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A compound described by the following formula:

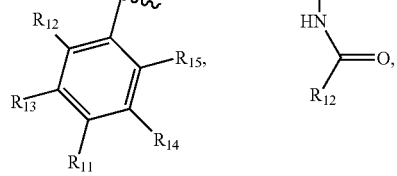

including both R and S enantiomeric forms and racemic mixtures;

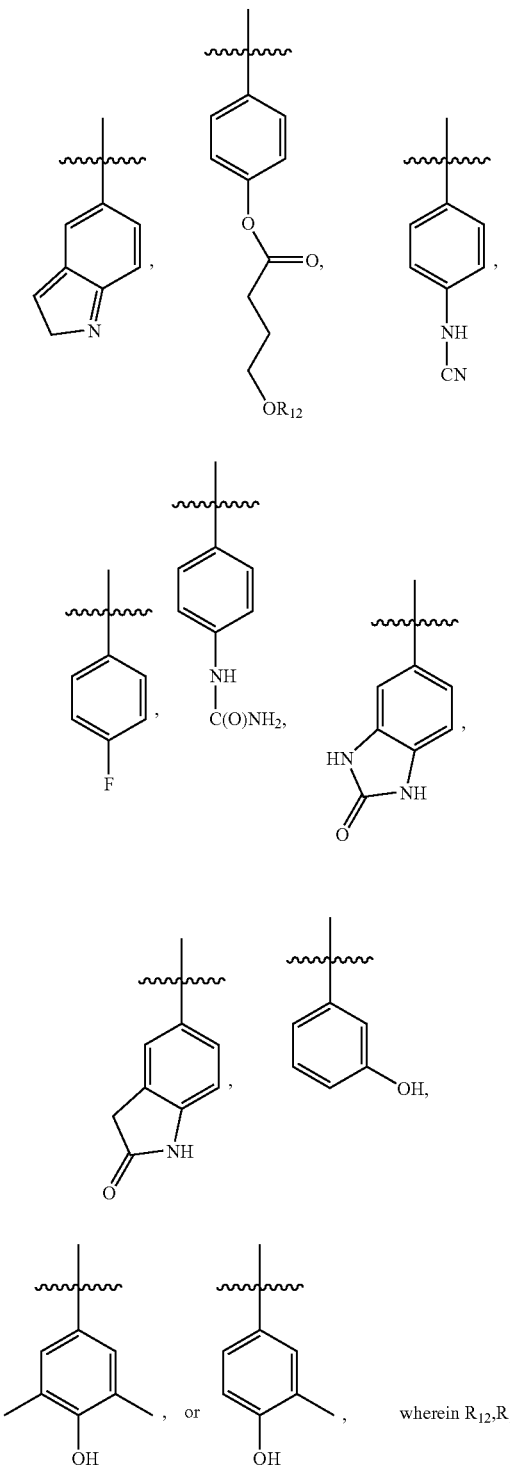

wherein $R_3$ is $R_{14}$ and $R_{15}$ are selected from the group consisting of hydrogen and $CH_3$; and $R_{11}$ is OH;

wherein $R_4$ is $CH_3$ or a linear or branched, saturated or unsaturated aliphatic chain having at least 2 carbons; and wherein $R_5$ is
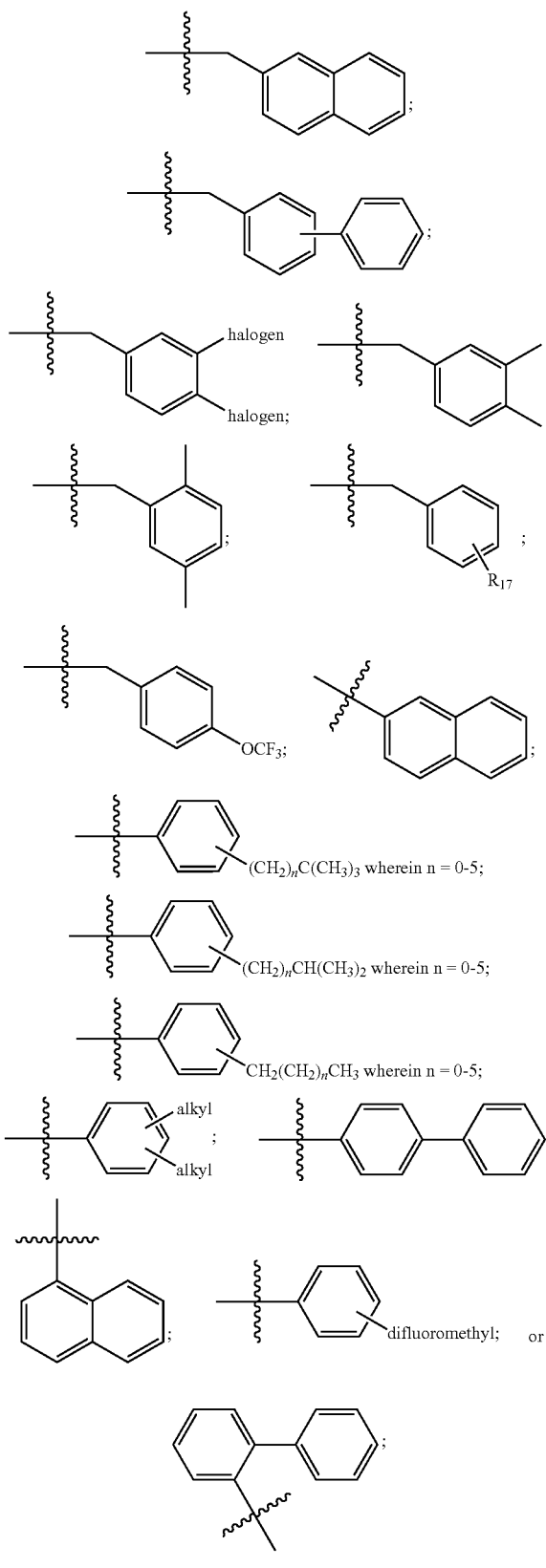
wherein $R_{17}$ is hydrogen, halogen, or $CH_3$.
2. The compound of claim 1, wherein $R_3$ is selected from the group consisting of:
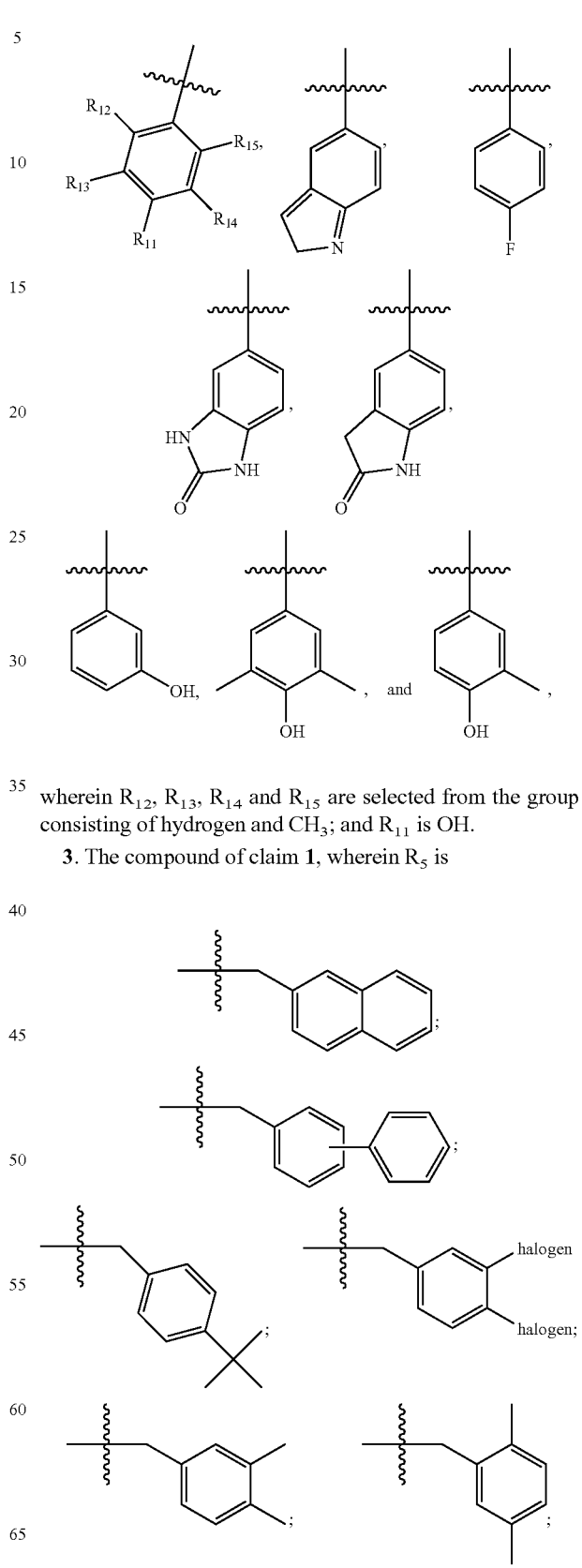
wherein $R_{12}$, $R_{13}$, $R_{14}$ and $R_{15}$ are selected from the group consisting of hydrogen and $CH_3$; and $R_{11}$ is OH.
3. The compound of claim 1, wherein $R_5$ is -continued

[chemical structures: 4-OCF3 benzyl; 2-naphthyl; phenyl-(CH2)nC(CH3)3 wherein n = 0-5; phenyl-(CH2)nCH(CH3)2 wherein n = 0-5; phenyl-CH2(CH2)nCH3 wherein n = 0-5; phenyl with two alkyl substituents; 4-biphenyl; 1-naphthyl; phenyl-difluoromethyl; or 2-biphenyl]

4. The compound of claim 1, wherein said compound is:

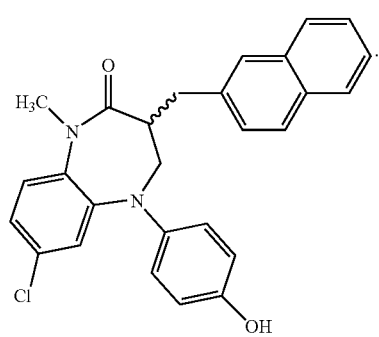

5. The compound of claim 1, wherein $R_3$ is

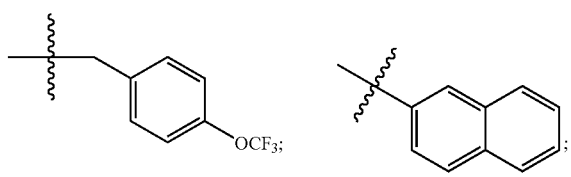

[structures with $R_{11}$, $R_{12}$, $R_{13}$, $R_{14}$, $R_{15}$; 3-hydroxyphenyl; 3,5-dimethyl-4-hydroxyphenyl; or 3-methyl-4-hydroxyphenyl].

6. The compound of claim 1, wherein $R_4$ is $CH_3$.

7. The compound of claim 1, wherein $R_5$ is

[structures: 2-naphthylmethyl; 3-phenylbenzyl; phenyl-$R_{17}$ benzyl; dihalobenzyl; dimethylbenzyl; dimethylbenzyl; or 4-OCF3 benzyl]; wherein $R_{17}$ is hydrogen, halogen, or $CH_3$.

8. The compound of claim 1, wherein $R_5$ is

[2-naphthylmethyl structure].

9. The compound of claim 5, wherein $R_5$ is

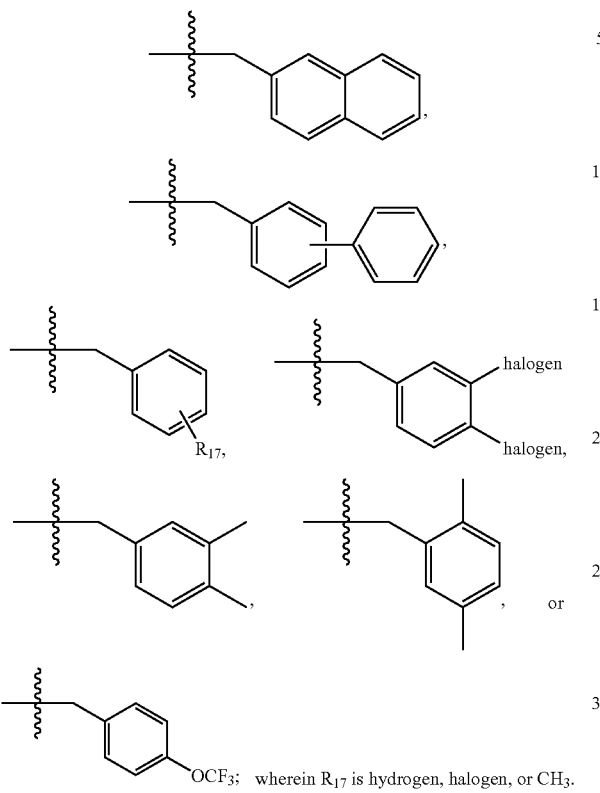

OCF$_3$; wherein $R_{17}$ is hydrogen, halogen, or CH$_3$.

10. The compound of claim 5, wherein $R_5$ is

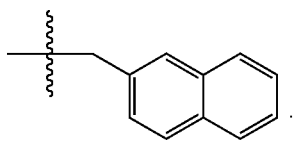

11. The compound of claim 5, wherein $R_4$ is CH$_3$, and $R_5$ is

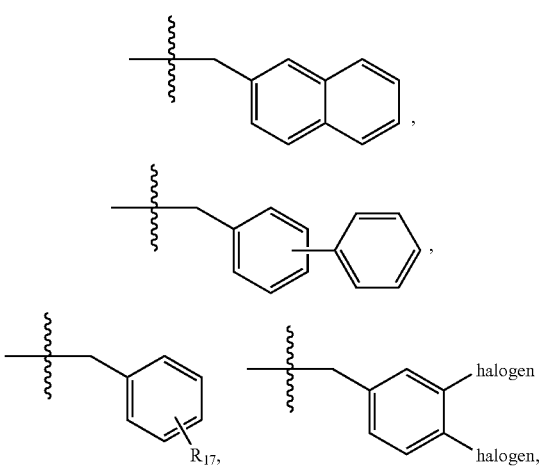

-continued

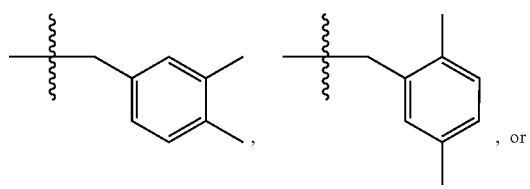

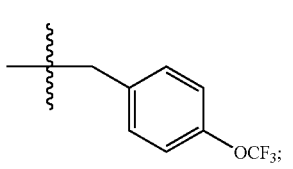

wherein $R_{17}$ is hydrogen, halogen, or CH$_3$.

12. The compound of claim 5, wherein $R_4$ is CH$_3$, and $R_5$ is

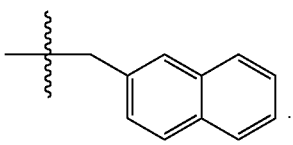

13. A pharmaceutical composition comprising a pharmaceutically acceptable carrier and a compound of claim 1 or a pharmaceutically acceptable salt thereof.

14. A compound described by the following formula:

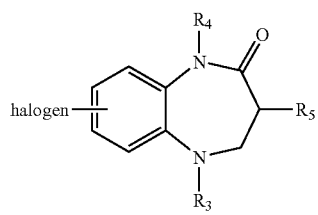

including both R and S enantiomeric forms and racemic mixtures;

wherein $R_3$ is

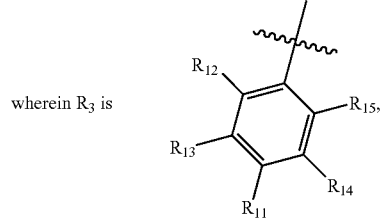

-continued

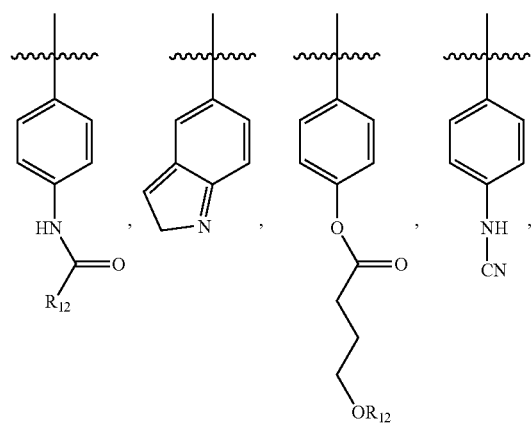

wherein $R_{12}$, $R_{13}$, $R_{14}$ and $R_{15}$ are selected from the group consisting of hydrogen and $CH_3$; and $R_{11}$ is OH;

wherein $R_4$ is

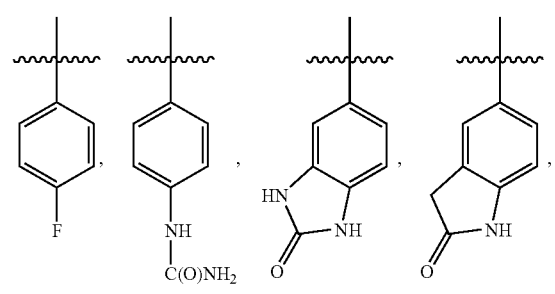

-continued

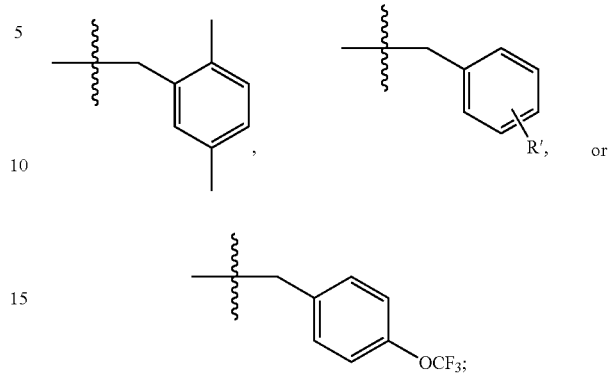

wherein R' is hydrogen, halogen, $CH_3$, or a linear or branched saturated or unsaturated aliphatic chain having at least 2 carbons; and wherein $R_5$ is $CH_3$ or a linear or branched, saturated or unsaturated aliphatic chain having at least 2 carbons.

15. The compound of claim 14, wherein $R_5$ is $CH_3$.

16. The compound of claim 14, wherein said compound is:

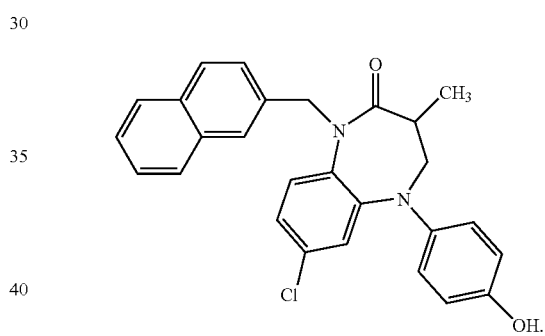

17. The compound of claim 15, wherein $R_3$ is

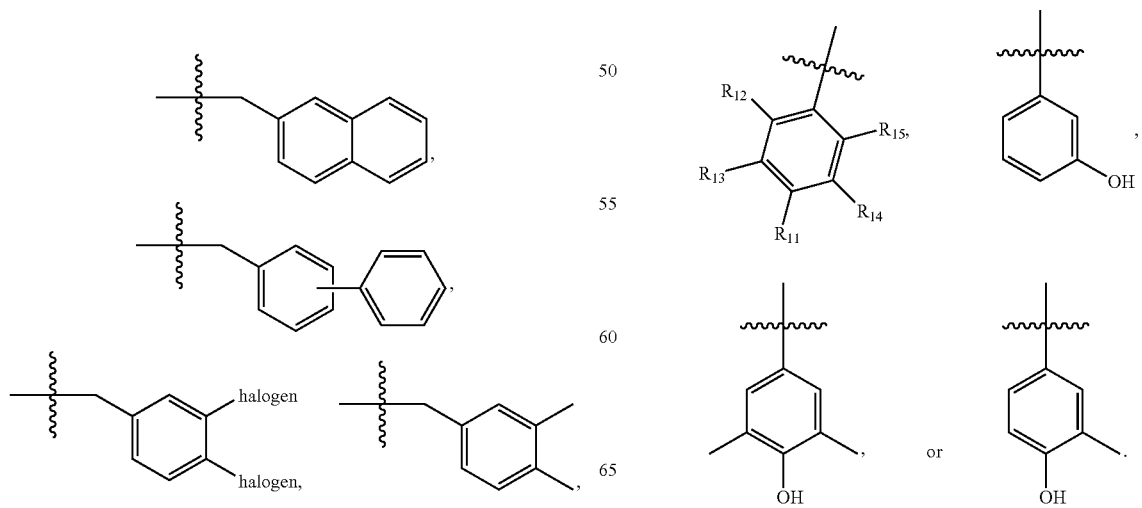

18. The compound of claim 17, wherein $R_4$ is
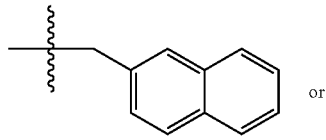 or 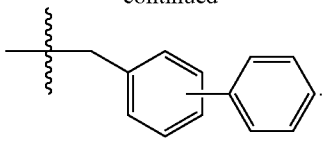.
19. A pharmaceutical composition comprising a pharmaceutically acceptable carrier and compound of claim 14 or a pharmaceutically acceptable salt thereof.
* * * * *